United States Patent
Carle et al.

(10) Patent No.: US 10,730,946 B2
(45) Date of Patent: *Aug. 4, 2020

(54) ANTIBODIES DIRECTED TO FC GAMMA RECEPTOR IIB AND FC EPSILON RECEPTOR

(71) Applicant: SuppreMol GmbH, Martinsried/München (DE)

(72) Inventors: Anna Carle, Munich (DE); Carolin Direnberger, Munich (DE); Peter Sondermann, Stockdorf (DE); Martina Mueller, Augsburg (DE); Nicole Rieth, Munich (DE); Thomas Pohl, Neuried (DE)

(73) Assignee: SUPPREMOL GMBH, Martinsreid/Munich (DE)

( * ) Notice: Subject to any disclaimer, the term of this patent is extended or adjusted under 35 U.S.C. 154(b) by 56 days.

This patent is subject to a terminal disclaimer.

(21) Appl. No.: 15/503,622

(22) PCT Filed: Aug. 13, 2015

(86) PCT No.: PCT/EP2015/068667
§ 371 (c)(1),
(2) Date: Feb. 13, 2017

(87) PCT Pub. No.: WO2016/023985
PCT Pub. Date: Feb. 18, 2016

(65) Prior Publication Data
US 2017/0226208 A1    Aug. 10, 2017

(30) Foreign Application Priority Data

Aug. 13, 2014 (EP) .................................... 14002825

(51) Int. Cl.
*C07K 16/28* (2006.01)
*A61K 39/00* (2006.01)

(52) U.S. Cl.
CPC ...... *C07K 16/283* (2013.01); *A61K 2039/505* (2013.01); *C07K 2317/24* (2013.01); *C07K 2317/31* (2013.01); *C07K 2317/34* (2013.01); *C07K 2317/41* (2013.01); *C07K 2317/52* (2013.01); *C07K 2317/55* (2013.01); *C07K 2317/56* (2013.01); *C07K 2317/565* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2009/0074771 A1    3/2009 Koenig et al.

FOREIGN PATENT DOCUMENTS

| EP | 2837637 A1 | | 2/2015 |
|---|---|---|---|
| WO | 2002/088317 A2 | | 11/2002 |
| WO | 2004/016750 A2 | | 2/2004 |
| WO | 2005/051999 A2 | | 6/2005 |
| WO | 2006/028956 | * | 3/2006 |
| WO | 2006/028956 A2 | | 3/2006 |
| WO | 2012/162068 A2 | | 11/2012 |
| WO | 2015/021089 A1 | | 2/2015 |
| WO | 2016/023985 A1 | | 2/2016 |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
International Search Report and Written Opinion dated Nov. 2, 2015 for International Application No. PCT/EP2015/068667 filed on Aug. 13, 2015.
Zhu et al., A novel human immunoglobulin Fcgamma-Fcepsilon bifunctional fusion protein inhibits FcepsilonRI-mediated degranulation. Nature Medicine, vol. 8, No. 5, pp. 518-521 (2002).
Tam et al., A bispecific antibody against human IgE and human FcgammaRII that inhibits antigen-induced histamine release by human mast cells and basophils. Allergy, vol. 59, No. 7, pp. 772-780 (2004).

* cited by examiner

*Primary Examiner* — Nelson B Moseley, II
(74) *Attorney, Agent, or Firm* — K&L Gates LLP; Louis C. Cullman; Hal Gibson

(57) ABSTRACT

Disclosed herein are recognition molecules that bind with a first binding domain to the Fc epsilon receptor (FcεR) and with a second binding domain to the Fc gamma receptor IIB (FcγRIIB), as well as uses for such recognition molecules.

21 Claims, 37 Drawing Sheets

Specification includes a Sequence Listing.

Figure 1

SPR analysis of humanized 8A6 WT and N297A variants, GB3 WT and ch8A6 WT

| | $k_{off}\ [s^{-1}]$ |
|---|---|
| hu8A6_wt | $9.5 \times 10^{-4}$ |
| hu8A6_N297A | $8.8 \times 10^{-4}$ |
| ch8A6_wt | $4.9 \times 10^{-4}$ |
| chGB3_N297A | $1 \times 10^{-2}$ |

Figure 1: Surface Plamon Resonance analysis of humanized 8A6 (hu8A6_VH10+VL6) according to SEQ. ID. No. 3 and 4 in either Wildtype or N297A format, ch8A6_WT (according to SEQ. ID. NO. 1 and 2) and chGB3_N297A.

Figure 2

Sequence of hu8A6_wt and hu8A6-N297A

The aminoacids of the variable regions are just numbered regardless to any numbering scheme. For a better understanding of the aminoacid changes in the Fc-domain the EU-numbering was chosen.

Heavy chain / humanized 8A6_wt (glycosylated)

VH domain (variant VH10)

```
1  QVQLVESGGG VVQPGRSLRL SCAASGFTFS DYYMAWVRQA PGKGLEWVAS ISYDGSNKYY
61 GDSVKGRFTI SRDNSKNTLY LQMNSLRAED TAVYYCARPG DYWGQGTLVT VSS (SEQ ID
NO. 3)
```

Fc-domain (glycosylated N297 / allotyp G1m17 containing K214; E356; M358; A431 / without C-terminal Lys; according to Eu-numbering)

```
118 ASTKGPSVFP LAPSSKSTSG GTAALGCLVK DYFPEPVTVS WNSGALTSGV HTFPAVLQSS
178 GLYSLSSVVT VPSSSLGTQT YICNVNHKPS NTKVDKKVEP KSCDKTHTCP PCPAPELLGG
238 PSVFLFPPKP KDTLMISRTP EVTCVVVDVS HEDPEVKFNW YVDGVEVHNA KTKPREEQYN
298 STYRVVSVLT VLHQDWLNGK EYKCKVSNKA LPAPIEKTIS KAKGQPREPQ VYTLPPSREE
358 MTKNQVSLTC LVKGFYPSDI AVEWESNGQP ENNYKTTPPV LDSDGSFFLY SKLTVDKSRW
418 QQGNVFSCSV MHEALHNHYT QKSLSLSPG- (SEQ ID NO. 6)
```

Heavy chain / humanized 8A6_N297A (deglycosylated)

VH domain see above

Fc-domain (N297A variant / allotype G1m17 containing K214; E356; M358; A431 / without C-terminal Lys; according to Eu-numbering)

```
118 ASTKGPSVFP LAPSSKSTSG GTAALGCLVK DYFPEPVTVS WNSGALTSGV HTFPAVLQSS
178 GLYSLSSVVT VPSSSLGTQT YICNVNHKPS NTKVDKKVEP KSCDKTHTCP PCPAPELLGG
238 PSVFLFPPKP KDTLMISRTP EVTCVVVDVS HEDPEVKFNW YVDGVEVHNA KTKPREEQYA
298 STYRVVSVLT VLHQDWLNGK EYKCKVSNKA LPAPIEKTIS KAKGQPREPQ VYTLPPSREE
358 MTKNQVSLTC LVKGFYPSDI AVEWESNGQP ENNYKTTPPV LDSDGSFFLY SKLTVDKSRW
418 QQGNVFSCSV MHEALHNHYT QKSLSLSPG- (SEQ ID NO. 28)
```

Figure 2: Sequences of hu8A6_wt and hu8A6_N297A variants showing position of N to A amino acid modification in N297A format

Figure 3: Non-blocking characteristic of ch8A6_N297A. Raji cells were incubated with a set amount of aggregated human IgG and varying amounts of ch8A6_N297A, chGB3_N297A or blocking antibodies 2B6 or mab1875 (R&D). The antibodies according to the invention are non-blocking.

Figure 4: Binding from 15 μg/ml to 0.005 μg/ml of Protein A purified antibody (hu8A6_VL + hu8A6_VH and ch8A6_N297A to native FcγRIIB expressed on Raji cells. Humanized 8A6 variants bind with high avidity to FcγRIIB expressed on Raji cells.

Figure 5: Binding of 15 μg/ml of Protein A purified antibody (hu8A6_VH + hu8A6_VL and ch8A6_N297A) and ch8A6_N297A to native FcγRIIA expressed on K562 cells. Antibodies according to the invention do not bind to FcγRIIA on K-562.

Figure 6

ITIM-Phosphorylation increased by ch8A6 in PBMC from healthy donor

Figure 6 a:
ITIM-Phosphorylation Assay. PBMC from healthy donor were isolated using Ficoll seperation and subsequently left untreated or incubated for 25 minutes with an antibody mix containing anti-IgM (anti-human, mouse) and anti-mouse IgG (rabbit). Subsequently the cells were either treated 20 minutes with 5µg/mL ch8A6_N297A or buffer as control (w/o). Cells were harvested after incubation and lysed according to protocol. Lysates were subjected to WB-analysis. ß-Actin = loading control.

Figure 6 b:
Control experiment for ITIM-Phosphorylation. Daudi cells were left untreated or treated for 25 minutes with an isotype control antibody, polyclonal anti-human anti-IgM (polycl. anti-hIgM), monoclonal anti human IgM (anti-hIgM), anti-hIgM + 5µg/mL ch8A6_N297A, anti-mouse IgG from rabbit (amouseIgG), amouseIgG+5µg/mL ch8A6, mix of anti-hIgM and amouseIgG (Ab mix) or Ab mix + 5µg/mL ch8A6_N297A). ß-Actin = loading control.

Figure 6c:
8A6 (wt) as well as hu8A6 showed strong phosphorylation of Fcgamma RIIB without the need of preceding coligation of BCR and FcgRIIB. After crosslinking of the receptors by the antibody mix, 8A6 (wt) and hu8A6 were - as expected - able to induce ITIM phosphorylation

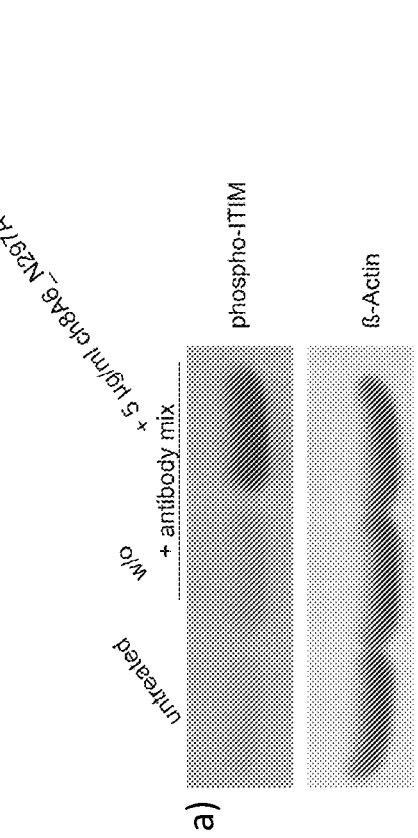

a)

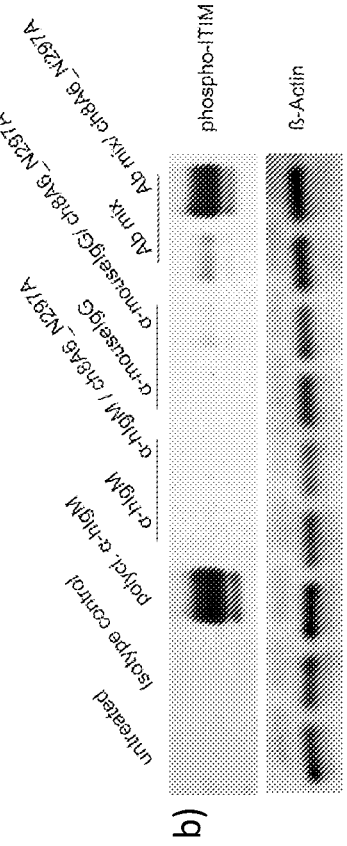

b)

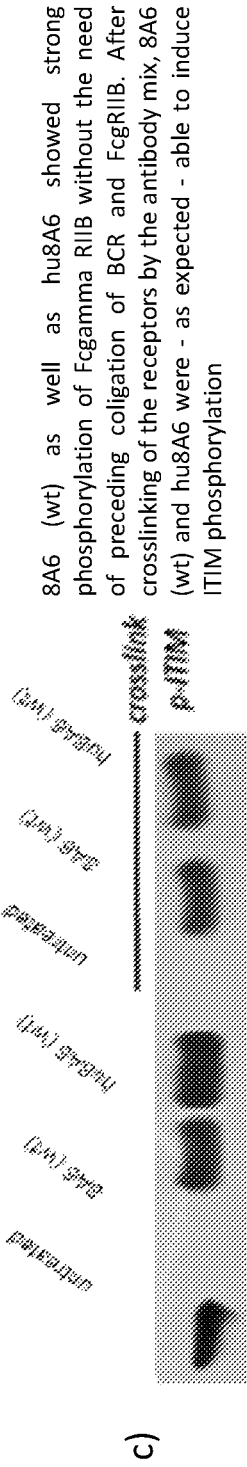

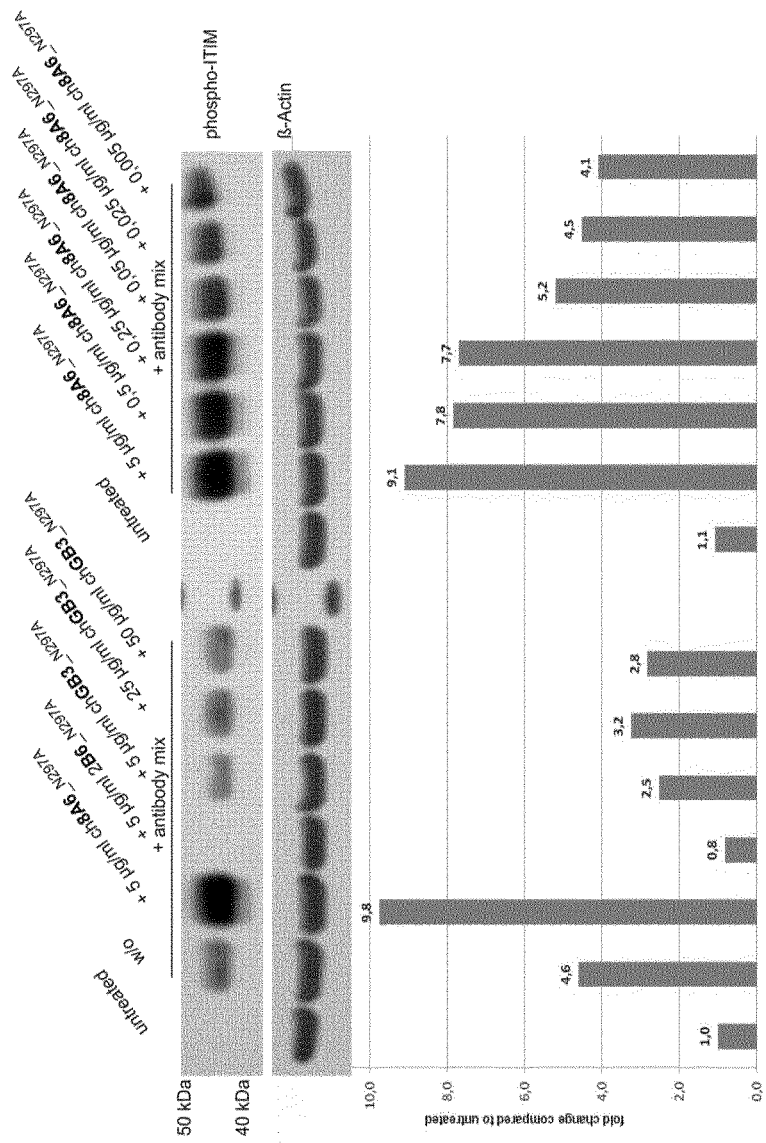

Figure 7:
ITIM-Phosphorylation Assay. Daudi cells left were either left untreated or incubated for 25 minutes with an antibody mix containing anti-IgM (anti-human, mouse) and anti-mouse IgG (rabbit). Subsequently the cells were either treated 20 minutes with varying amounts of chGB3_N297A or ch8A6_N297A or buffer as control (w/o). Cells were harvested after incubation and lysed according to protocol. Lysates were subjected to WB-analysis. ß-Actin = loading control.

Figure 8: Comparison of the effect of the humanized variant hu8A6_N297A and ch8A6_N297A on ITIM phosphorylation in primary PBMCs. After crosslinking of BCR and FcgRIIB by the antibody mix, the different antibodies were added at 5 µg/ml and Western Blot analysis for ITIM phosphorylation was conducted. ß-Actin = loading control.

Figure 9

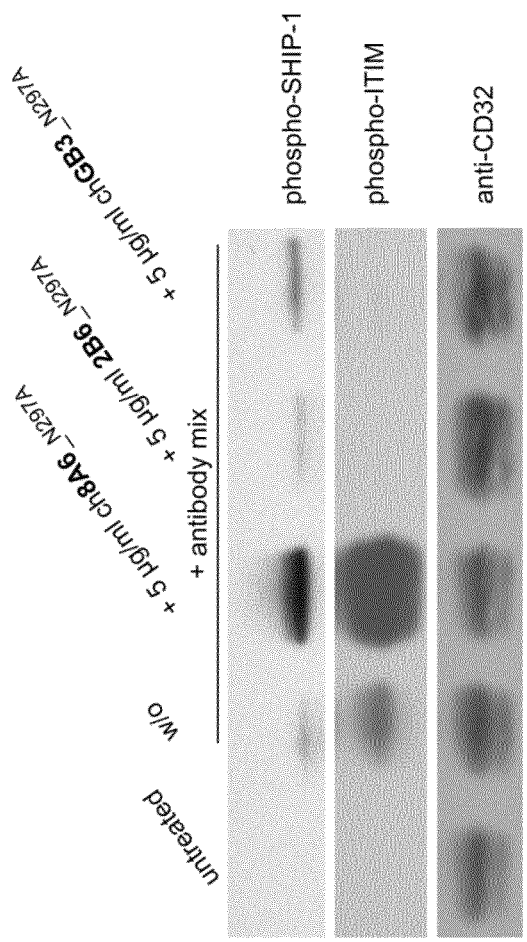

Figure 9: Co-Immunoprecipitation of phosphorylated SHIP-1 with FcγRIIB ITIM. After stimulation of Daudi cells with the antibody mix and either ch8A6_N297A, blocking anti-FcγRIIB antibody 2B6 or chGB3_N297A (5μg/mL), FcγRIIB was precipitated from cell lysates and Western Blot analysis was performed for the phosphatase SHIP-1. anti-CD32 using pan anti-CD32 antibody (AF1330) = loading control.

Figure 10

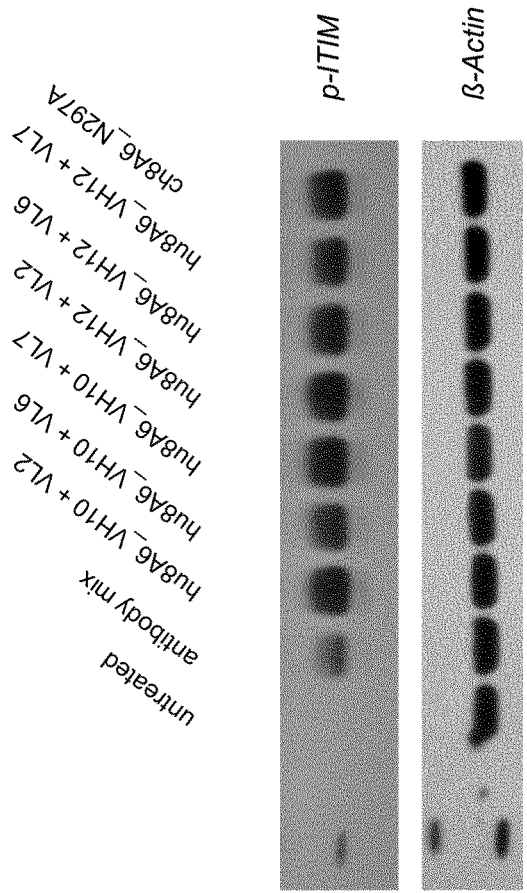

Figure 10:
ITIM-Phosphorylation Assay. Daudi cells were left incubated for 25 minutes with buffer (untreated) or a mix (antibody mix) containing anti-IgM (anti-human, mouse) and anti-mouse IgG (rabbit). Subsequently the cells were either treated 20 minutes with 0.25µg/mL of ch8A6_N297A or humanized 8A6 variants hu8A6_VH10+VL2/ VH10+VL7/VH10+VL6/ VH12+VL2/VH12+VL7/VH12+VL6/VH12+VL7. Cells were harvested after incubation and lysed according to protocol. Lysates were subjected to WB-analysis. ß-Actin = loading control.

Figure 11

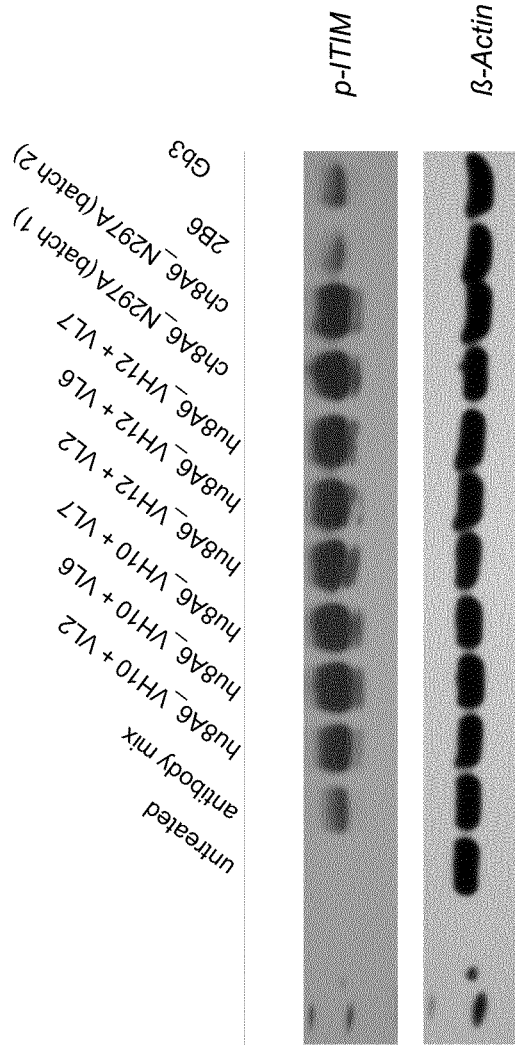

Figure 11:
ITIM-Phosphorylation Assay. Daudi cells were left incubated for 25 minutes with buffer (untreated) or a mix (antibody mix) containing anti-IgM (anti-human, mouse) and anti-mouse IgG (rabbit). Subsequently the cells were either treated 20 minutes with 0.25µg/mL of ch8A6_N297A, humanized 8A6 variants hu8A6_VH10+VL2/VH10+VL6/ VH10+VL7/VH12+VL2/VH12+VL6/VH12+VL7, blocking 2B6 or chGB3_N297A. Cells were harvested after incubation and lysed according to protocol. Lysates were subjected to WB-analysis. ß-Actin = loading control.

Figure 12: Experimental setup for SLE-PBL mouse model. PBL from human SLE patients are transfered into immuno-compromised mice. PBL cells are engrafted and mice are subsequently treated with control (PBS) or anti-FcγRIIb ch8A6_N297A antibody according to the invention.

Total human IgG level [μg/mL] in mice grafted with PBL from human donors suffering from SLE. Depicted are mice treated with control (#2, PBS) or chimeric 8A6 = ch8A6_N297A (#3 and #4, anti-FcγRIIB antibody, N297A-Format). No significant difference in total human IgG between PBS or anti-FcγRIIB.

Reduction of disease specific human anti-DNA IgG in ch8A6_N297A treated mice starting week 4 post SLE-PBL transfer/grafting. Depicted are anti-DNA IgG titers in two different mice, #3 and #4 (treated with ch8A6_N297A), #2 shows PBS control

SEQUENCE LISTING

```
<160> NUMBER OF SEQ ID NOS: 38

<210> SEQ ID NO 1
<211> LENGTH: 113
<212> TYPE: PRT
<213> ORGANISM: Rattus norvegicus
<220> FEATURE:
<221> NAME/KEY: MISC_FEATURE
<222> LOCATION: (1)..(113)
<223> OTHER INFORMATION: VH r8A6

<400> SEQUENCE: 1

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Ser Asp Tyr
                20                  25                  30

Tyr Met Ala Trp Val Arg Gln Ala Pro Lys Lys Gly Leu Glu Trp Val
            35                  40                  45

Ala Ser Ile Ser Ser Asp Gly Ser Asn Thr Tyr Tyr Gly Asp Ser Val
```

```
Lys Gly Arg Phe Thr Ile Ser Arg Asp Asn Thr Arg Ser Asn Leu Tyr
 65                  70                  75                  80

Leu Gln Met Asn Ser Leu Arg Ser Glu Asp Thr Ala Thr Tyr Tyr Cys
                 85                  90                  95

Ala Arg Pro Gly Asp Tyr Trp Gly Gln Gly Val Met Val Thr Val Ser
            100                 105                 110

Ser

<210> SEQ ID NO 2
<211> LENGTH: 108
<212> TYPE: PRT
<213> ORGANISM: Rattus norvegicus
<220> FEATURE:
<221> NAME/KEY: MISC_FEATURE
<223> OTHER INFORMATION: VL r8A6
<220> FEATURE:
<221> NAME/KEY: MISC_FEATURE
<222> LOCATION: (1)..(108)
<223> OTHER INFORMATION: VL r8A6

<400> SEQUENCE: 2

Asn Ile Val Met Thr Gln Ser Pro Thr Ser Met Phe Ile Ser Val Gly
 1               5                  10                  15

Asp Arg Val Thr Met Asn Cys Lys Ala Ser Gln Asn Val Gly Thr Tyr
                20                  25                  30

Val Asp Trp Phe Gln Gln Lys Thr Gly Gln Ser Pro Thr Leu Leu Ile
            35                  40                  45

Phe Gly Ala Ser Asn Arg Tyr Thr Gly Val Pro Asp Arg Phe Thr Gly
     50                  55                  60

Ser Gly Ser Gly Thr Asp Phe Thr Leu Ser Ile Ser Asn Met Gln Ala
 65                  70                  75                  80

Glu Asp Leu Ala Val Tyr Tyr Cys Leu Gln Tyr Asn Tyr His Pro Tyr
                 85                  90                  95

Thr Phe Gly Pro Gly Thr Thr Leu Glu Leu Lys Arg
            100                 105

<210> SEQ ID NO 3
<211> LENGTH: 113
<212> TYPE: PRT
<213> ORGANISM: Artificial
<220> FEATURE:
<223> OTHER INFORMATION: humanized antibody
<220> FEATURE:
<221> NAME/KEY: MISC_FEATURE
<222> LOCATION: (1)..(113)
<223> OTHER INFORMATION: VH hu8A6

<400> SEQUENCE: 3

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asp Tyr
                20                  25                  30

Tyr Met Ala Trp Val Arg Gln Ala Pro Gly Lys Gly Leu Glu Trp Val
            35                  40                  45

Ala Ser Ile Ser Tyr Asp Gly Ser Asn Lys Tyr Tyr Gly Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                        85                  90                  95

Ala Arg Pro Gly Asp Tyr Trp Gly Gln Gly Thr Leu Val Thr Val Ser
                    100                 105                 110

Ser

<210> SEQ ID NO 4
<211> LENGTH: 108
<212> TYPE: PRT
<213> ORGANISM: Artificial
<220> FEATURE:
<223> OTHER INFORMATION: humanized antibody
<220> FEATURE:
<221> NAME/KEY: MISC_FEATURE
<222> LOCATION: (1)..(108)
<223> OTHER INFORMATION: VL hu8A6

<400> SEQUENCE: 4

Gln Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Tyr
                20                  25                  30

Val Asp Trp Tyr Gln Gln Lys Pro Gly Gln Ala Pro Arg Leu Leu Ile
            35                  40                  45

Tyr Gly Ala Ser Thr Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Leu Gln Tyr Asn Asn His Pro Tyr
                85                  90                  95

Thr Phe Gly Gln Gly Thr Lys Leu Glu Ile Lys Arg
                100                 105

<210> SEQ ID NO 5
<211> LENGTH: 181
<212> TYPE: PRT
<213> ORGANISM: Homo sapiens
<220> FEATURE:
<221> NAME/KEY: MISC_FEATURE
<222> LOCATION: (1)..(181)
<223> OTHER INFORMATION: human FcγRIIB

<400> SEQUENCE: 5

Met Gly Thr Pro Ala Ala Pro Pro Lys Ala Val Leu Lys Leu Glu Pro
1               5                   10                  15

Gln Trp Ile Asn Val Leu Gln Glu Asp Ser Val Thr Leu Thr Cys Arg
                20                  25                  30

Gly Thr His Ser Pro Glu Ser Asp Ser Ile Gln Trp Phe His Asn Gly
            35                  40                  45

Asn Leu Ile Pro Thr His Thr Gln Pro Ser Tyr Arg Phe Lys Ala Asn
    50                  55                  60

Asn Asn Asp Ser Gly Glu Tyr Thr Cys Gln Thr Gly Gln Thr Ser Leu
65                  70                  75                  80

Ser Asp Pro Val His Leu Thr Val Leu Ser Glu Trp Leu Val Leu Gln
                85                  90                  95

Thr Pro His Leu Glu Phe Gln Glu Gly Glu Thr Ile Val Leu Arg Cys
                100                 105                 110

His Ser Trp Lys Asp Lys Pro Leu Val Lys Val Thr Phe Phe Gln Asn
            115                 120                 125

Gly Lys Ser Lys Lys Phe Ser Arg Ser Asp Pro Asn Phe Ser Ile Pro
```

```
            130                 135                 140
Gln Ala Asn His Ser His Ser Gly Asp Tyr His Cys Thr Gly Asn Ile
145                 150                 155                 160

Gly Tyr Thr Leu Tyr Ser Ser Lys Pro Val Thr Ile Thr Val Gln Ala
                165                 170                 175

Pro Ser Ser Ser Pro
            180

<210> SEQ ID NO 6
<211> LENGTH: 329
<212> TYPE: PRT
<213> ORGANISM: Artificial
<220> FEATURE:
<223> OTHER INFORMATION: humanized antibody
<220> FEATURE:
<221> NAME/KEY: MISC_FEATURE
<222> LOCATION: (1)..(329)
<223> OTHER INFORMATION: CH hu8A6_wt

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 7
<211> LENGTH: 106
<212> TYPE: PRT
<213> ORGANISM: Artificial
<220> FEATURE:
<223> OTHER INFORMATION: humanized antibody
<220> FEATURE:
<221> NAME/KEY: MISC_FEATURE
<222> LOCATION: (1)..(106)
<223> OTHER INFORMATION: CL hu8A6_wt

<400> SEQUENCE: 7

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 8
<211> LENGTH: 339
<212> TYPE: DNA
<213> ORGANISM: Artificial
<220> FEATURE:
<223> OTHER INFORMATION: humanized antibody
<220> FEATURE:
<221> NAME/KEY: misc_feature
<222> LOCATION: (1)..(339)
<223> OTHER INFORMATION: VH hu8A6

<400> SEQUENCE: 8
caggtgcagc tggtggagtc tgggggaggc gtggtccagc ctggggaggtc cctgagactc     60 tcctgtgcag cctctggatt caccttcagt gactattaca tggcctgggt ccgccaggct    120
ccaggcaagg ggctggagtg ggtggcatcc atatcatacg atggaagcaa taagtactac    180
ggagactccg tgaagggccg attcaccatc tccagagaca attccaagaa cacgctgtat    240
ctgcaaatga acagcctgag agctgaggac acggctgtgt attactgtgc gagaccggga    300
gactactggg gccaaggaac cctggtcacc gtcagctca                            339

<210> SEQ ID NO 9
<211> LENGTH: 324
<212> TYPE: DNA
<213> ORGANISM: Artificial
<220> FEATURE:
<223> OTHER INFORMATION: humanized antibody
<220> FEATURE:
<221> NAME/KEY: misc_feature
```

```
<222> LOCATION: (1)..(324)
<223> OTHER INFORMATION: VL hu8A6

<400> SEQUENCE: 9
cagatagtga tgacgcagtc tccagccacc ctgtctgtgt ctccagggga aagagccacc      60
ctctcctgca gggccagtca gtccgttggc tcctatgtcg actggtacca gcagaaacct    120
ggccaggctc ccaggctcct catctatggt gcatccacca ggtacactgg tatcccagcc    180
aggttcagtg gcagtgggtc tgggacagag ttcactctca ccatcagcag cctgcagtct    240
gaagattttg cagtttatta ctgtctgcag tataacaacc atccttacac ttttggccag    300
gggaccaagc tggagatcaa acgt                                            324

<210> SEQ ID NO 10
<211> LENGTH: 990
<212> TYPE: DNA
<213> ORGANISM: Artificial
<220> FEATURE:
<223> OTHER INFORMATION: humanized antibody
<220> FEATURE:
<221> NAME/KEY: misc_feature
<222> LOCATION: (1)..(990)
<223> OTHER INFORMATION: CH hu8A6_wt

<400> SEQUENCE: 10
gcctccacca agggcccatc ggtcttcccc ctggcaccct cctccaagag cacctctggg      60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa ggttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggttaa                                      990

<210> SEQ ID NO 11
<211> LENGTH: 321
<212> TYPE: DNA
<213> ORGANISM: Artificial
<220> FEATURE:
<223> OTHER INFORMATION: humanized antibody
<220> FEATURE:
<221> NAME/KEY: misc_feature
<222> LOCATION: (1)..(321)
<223> OTHER INFORMATION: CL hu8A6_wt

<400> SEQUENCE: 11
```

```
acgtggctg caccatcggt cttcatcttc cgccatctg atgagcagtt gaaatctgga       60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgtta g                                              321
```

```
<210> SEQ ID NO 12
<211> LENGTH: 125
<212> TYPE: PRT
<213> ORGANISM: Homo sapiens
<220> FEATURE:
<221> NAME/KEY: MISC_FEATURE
<222> LOCATION: (1)..(125)
<223> OTHER INFORMATION: hu soluble FCyRIIA

<400> SEQUENCE: 12

Arg Phe Lys Ala Asn Asn Asn Asp Ser Gly Glu Tyr Thr Cys Gln Thr
1               5                   10                  15

Gly Gln Thr Ser Leu Ser Asp Pro Val His Leu Thr Val Leu Ser Glu
            20                  25                  30

Trp Leu Val Leu Gln Thr Pro His Leu Glu Phe Gln Glu Gly Glu Thr
        35                  40                  45

Ile Met Leu Arg Cys His Ser Trp Lys Asp Lys Pro Leu Val Lys Val
    50                  55                  60

Thr Phe Phe Gln Asn Gly Lys Ser Gln Lys Phe Ser Arg Leu Asp Pro
65                  70                  75                  80

Thr Phe Ser Ile Pro Gln Ala Asn His Ser His Ser Gly Asp Tyr His
                85                  90                  95

Cys Thr Gly Asn Ile Gly Tyr Thr Leu Phe Ser Ser Lys Pro Val Thr
            100                 105                 110

Ile Thr Val Gln Val Pro Ser Met Gly Ser Ser Ser Pro
        115                 120                 125
```

```
<210> SEQ ID NO 13
<211> LENGTH: 179
<212> TYPE: PRT
<213> ORGANISM: Homo sapiens
<220> FEATURE:
<221> NAME/KEY: MISC_FEATURE
<222> LOCATION: (1)..(179)
<223> OTHER INFORMATION: soluble mutated human FCyRIIA

<400> SEQUENCE: 13

Met Ala Pro Pro Lys Ala Val Leu Lys Leu Glu Pro Pro Trp Ile Asn
1               5                   10                  15

Val Leu Gln Glu Asp Ser Val Thr Leu Thr Cys Gln Gly Ala Arg Ser
            20                  25                  30

Pro Glu Ser Asp Ser Ile Gln Trp Phe His Asn Gly Asn Leu Ile Pro
        35                  40                  45

Thr His Thr Gln Pro Ser Tyr Arg Phe Lys Ala Asn Asn Asn Asp Ser
    50                  55                  60

Gly Glu Tyr Thr Cys Gln Thr Gly Gln Thr Ser Leu Ser Asp Pro Val
65                  70                  75                  80

His Leu Thr Val Leu Ser Glu Trp Leu Val Leu Gln Thr Pro His Leu
                85                  90                  95

Glu Phe Gln Glu Gly Glu Thr Ile Met Leu Arg Cys His Ser Trp Lys
```

-continued

```
                    100                 105                 110
Asp Lys Pro Leu Val Lys Val Thr Phe Phe Gln Asn Gly Lys Ser Lys
            115                 120                 125

Lys Phe Ser Arg Ser Asp Pro Asn Phe Ser Ile Pro Gln Ala Asn His
            130                 135                 140

Ser His Ser Gly Asp Tyr His Cys Thr Gly Asn Ile Gly Tyr Thr Leu
145                 150                 155                 160

Phe Ser Ser Lys Pro Val Thr Ile Thr Val Gln Val Pro Ser Met Gly
                165                 170                 175

Ser Ser Pro

<210> SEQ ID NO 14
<211> LENGTH: 5
<212> TYPE: PRT
<213> ORGANISM: artificial
<220> FEATURE:
<223> OTHER INFORMATION: heavy chain CDR1 from rat antibody 8A6

<400> SEQUENCE: 14

Asp Tyr Tyr Met Ala
1               5

<210> SEQ ID NO 15
<211> LENGTH: 17
<212> TYPE: PRT
<213> ORGANISM: artificial
<220> FEATURE:
<223> OTHER INFORMATION: heavy chain CDR2 from rat antibody 8A6

<400> SEQUENCE: 15

Ser Ile Ser Ser Asp Gly Ser Asn Thr Tyr Tyr Gly Asp Ser Val Lys
1               5                   10                  15

Gly

<210> SEQ ID NO 16
<211> LENGTH: 6
<212> TYPE: PRT
<213> ORGANISM: artificial
<220> FEATURE:
<223> OTHER INFORMATION: heavy chain CDR3 from rat antibody 8A6

<400> SEQUENCE: 16

Ala Arg Pro Gly Asp Tyr
1               5

<210> SEQ ID NO 17
<211> LENGTH: 11
<212> TYPE: PRT
<213> ORGANISM: artificial
<220> FEATURE:
<223> OTHER INFORMATION: light chain CDR1 from rat antibody 8A6

<400> SEQUENCE: 17

Lys Ala Ser Gln Asn Val Gly Thr Tyr Val Asp
1               5                   10

<210> SEQ ID NO 18
<211> LENGTH: 7
<212> TYPE: PRT
<213> ORGANISM: artificial
<220> FEATURE:
<223> OTHER INFORMATION: light chain CDR2 from rat antibody 8A6

<400> SEQUENCE: 18
```

Gly Ala Ser Asn Arg Tyr Thr
1               5

<210> SEQ ID NO 19
<211> LENGTH: 9
<212> TYPE: PRT
<213> ORGANISM: artificial
<220> FEATURE:
<223> OTHER INFORMATION: light chain CDR3 from rat antibody 8A6

<400> SEQUENCE: 19

Leu Gln Tyr Asn Tyr His Pro Tyr Thr
1               5

<210> SEQ ID NO 20
<211> LENGTH: 5
<212> TYPE: PRT
<213> ORGANISM: artificial
<220> FEATURE:
<223> OTHER INFORMATION: heavy chain CDR1 from humanized antibody 8A6

<400> SEQUENCE: 20

Asp Tyr Tyr Met Ala
1               5

<210> SEQ ID NO 21
<211> LENGTH: 17
<212> TYPE: PRT
<213> ORGANISM: artificial
<220> FEATURE:
<223> OTHER INFORMATION: heavy chain CDR2 from humanized antibody 8A6

<400> SEQUENCE: 21

Ser Ile Ser Tyr Asp Gly Ser Asn Lys Tyr Tyr Gly Asp Ser Val Lys
1               5                   10                  15

Gly

<210> SEQ ID NO 22
<211> LENGTH: 6
<212> TYPE: PRT
<213> ORGANISM: artificial
<220> FEATURE:
<223> OTHER INFORMATION: heavy chain CDR3 from humanized antibody 8A6

<400> SEQUENCE: 22

Ala Arg Pro Gly Asp Tyr
1               5

<210> SEQ ID NO 23
<211> LENGTH: 11
<212> TYPE: PRT
<213> ORGANISM: artificial
<220> FEATURE:
<223> OTHER INFORMATION: light chain CDR1 from humanized antibody 8A6

<400> SEQUENCE: 23

Arg Ala Ser Gln Ser Val Gly Ser Tyr Val Asp
1               5                   10

<210> SEQ ID NO 24
<211> LENGTH: 7
<212> TYPE: PRT
<213> ORGANISM: artificial
<220> FEATURE:
<223> OTHER INFORMATION: light chain CDR2 from humanized antibody 8A6

```
<400> SEQUENCE: 24

Gly Ala Ser Thr Arg Tyr Thr
1               5

<210> SEQ ID NO 25
<211> LENGTH: 9
<212> TYPE: PRT
<213> ORGANISM: artificial
<220> FEATURE:
<223> OTHER INFORMATION: light chain CDR3 from humanized antibody 8A6

<400> SEQUENCE: 25

Leu Gln Tyr Asn Asn His Pro Tyr Thr
1               5

<210> SEQ ID NO 26
<211> LENGTH: 104
<212> TYPE: PRT
<213> ORGANISM: artificial
<220> FEATURE:
<223> OTHER INFORMATION: variable region of the heavy chain of antibody
      GB3

<400> SEQUENCE: 26

Val Gln Leu Gln Gln Ser Gly Pro Glu Leu Val Lys Pro Gly Ala Ser
1               5                   10                  15

Val Lys Ile Ser Cys Lys Ala Ser Gly Tyr Thr Phe Thr Asp Tyr Tyr
            20                  25                  30

Ile Tyr Trp Val Lys Gln Trp Pro Gly Gln Gly Leu Glu Trp Ile Gly
        35                  40                  45

Trp Ile Phe Pro Gly Thr Gly Asn Thr Tyr Tyr Asn Glu Asn Phe Lys
    50                  55                  60

Asp Lys Ala Thr Leu Thr Ile Asp Arg Ser Ser Ser Thr Ala Tyr Met
65                  70                  75                  80

Leu Leu Gly Ser Leu Thr Ser Glu Asp Ser Ala Val Tyr Phe Cys Tyr
                85                  90                  95

Gly Pro Phe Ala Tyr Trp Gly Gln
            100

<210> SEQ ID NO 27
<211> LENGTH: 104
<212> TYPE: PRT
<213> ORGANISM: artificial
<220> FEATURE:
<223> OTHER INFORMATION: variable region of the light chain of the
      antbody GB3

<400> SEQUENCE: 27

Arg Ile Gln Leu Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Thr Ser Ala Leu Asp Ser Gly Val Pro Lys Arg Phe Ser Gly
    50                  55                  60

Ser Gly Ser Gly Ser Asn Tyr Ser Leu Thr Ile Ser Ser Leu Glu Ser
65                  70                  75                  80

Glu Asp Phe Ala Asp Tyr Tyr Cys Leu Gln Tyr Ala Asn Tyr Pro Tyr
                85                  90                  95
```

```
Thr Phe Gly Gly Gly Thr Lys Leu
                100

<210> SEQ ID NO 28
<211> LENGTH: 329
<212> TYPE: PRT
<213> ORGANISM: artificial
<220> FEATURE:
<223> OTHER INFORMATION: IgG heavy chain constant region with N to A
      change at position 297 when regarding pos. 1 as pos. 118

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 29
```

```
<211> LENGTH: 5
<212> TYPE: PRT
<213> ORGANISM: artificial
<220> FEATURE:
<223> OTHER INFORMATION: CDR1 from heavy chain variable region
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid

<400> SEQUENCE: 29

Xaa Xaa Xaa Met Ala
1               5

<210> SEQ ID NO 30
<211> LENGTH: 17
<212> TYPE: PRT
<213> ORGANISM: artificial
<220> FEATURE:
<223> OTHER INFORMATION: CDR2 from heavy chain variable region
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (8)..(8)
<223> OTHER INFORMATION: Xaa can be any amino acid
<220> FEATURE:
<221> NAME/KEY: misc
<222> LOCATION: (9)..(9)
<223> OTHER INFORMATION: Xaa can K or T
<220> FEATURE:
<221> NAME/KEY: misc
<222> LOCATION: (10)..(10)
<223> OTHER INFORMATION: Xaa can be any amino acid
<220> FEATURE:
<221> NAME/KEY: misc
<222> LOCATION: (11)..(11)
<223> OTHER INFORMATION: Xaa can be any amino acid
<220> FEATURE:
<221> NAME/KEY: misc
<222> LOCATION: (16)..(16)
<223> OTHER INFORMATION: Xaa can be any amino acid
<220> FEATURE:
<221> NAME/KEY: misc
<222> LOCATION: (17)..(17)
<223> OTHER INFORMATION: Xaa can be any amino acid
<220> FEATURE:
<221> NAME/KEY: misc
<222> LOCATION: (17)..(17)
<223> OTHER INFORMATION: Xaa can be any amini acid

<400> SEQUENCE: 30

Ser Xaa Ser Tyr Asp Gly Ser Xaa Xaa Xaa Xaa Gly Asp Ser Val Xaa
1               5                   10                  15
```

Xaa

```
<210> SEQ ID NO 31
<211> LENGTH: 6
<212> TYPE: PRT
<213> ORGANISM: artificial
<220> FEATURE:
<223> OTHER INFORMATION: CDR3 from heavy chain variable region
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (5)..(5)
<223> OTHER INFORMATION: Xaa can be any amino acid
<220> FEATURE:
<221> NAME/KEY: misc
<222> LOCATION: (6)..(6)
<223> OTHER INFORMATION: Xaa can be any amino acid
<220> FEATURE:
<221> NAME/KEY: misc
<222> LOCATION: (6)..(6)
<223> OTHER INFORMATION: Xaa can be any amino acid

<400> SEQUENCE: 31

Ala Arg Xaa Gly Xaa Xaa
1               5

<210> SEQ ID NO 32
<211> LENGTH: 11
<212> TYPE: PRT
<213> ORGANISM: artificial
<220> FEATURE:
<223> OTHER INFORMATION: CDR1 from light chain variable region
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (4)..(4)
<223> OTHER INFORMATION: Xaa can be any amino acid
<220> FEATURE:
<221> NAME/KEY: misc
<222> LOCATION: (5)..(5)
<223> OTHER INFORMATION: Xaa can be any amino acid
<220> FEATURE:
<221> NAME/KEY: misc
<222> LOCATION: (7)..(7)
<223> OTHER INFORMATION: Xaa can be any amino acid
<220> FEATURE:
<221> NAME/KEY: misc
<222> LOCATION: (8)..(8)
<223> OTHER INFORMATION: Xaa can be S or T
<220> FEATURE:
<221> NAME/KEY: misc
<222> LOCATION: (9)..(9)
<223> OTHER INFORMATION: Xaa can be any amino acid

<400> SEQUENCE: 32

Xaa Xaa Xaa Xaa Xaa Val Xaa Xaa Xaa Val Asp
```

<210> SEQ ID NO 33
<211> LENGTH: 7
<212> TYPE: PRT
<213> ORGANISM: artificial
<220> FEATURE:
<223> OTHER INFORMATION: CDR2 from light chain variable region
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (4)..(4)
<223> OTHER INFORMATION: Xaa can be T or N

<400> SEQUENCE: 33

Gly Xaa Xaa Xaa Arg Tyr Thr
1               5

<210> SEQ ID NO 34
<211> LENGTH: 9
<212> TYPE: PRT
<213> ORGANISM: artificial
<220> FEATURE:
<223> OTHER INFORMATION: CDR3 from light chain variable region
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (1)..(1)
<223> OTHER INFORMATION: Xaa can be any amino acid
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (4)..(4)
<223> OTHER INFORMATION: Xaa can be any amino acid
<220> FEATURE:
<221> NAME/KEY: misc
<222> LOCATION: (7)..(7)
<223> OTHER INFORMATION: Xaa can be any amino acid
<220> FEATURE:
<221> NAME/KEY: misc
<222> LOCATION: (8)..(8)
<223> OTHER INFORMATION: Xaa can be any amino acid
<220> FEATURE:
<221> NAME/KEY: misc
<222> LOCATION: (9)..(9)
<223> OTHER INFORMATION: Xaa can be any amino acid
<220> FEATURE:
<221> NAME/KEY: misc
<222> LOCATION: (9)..(9)
<223> OTHER INFORMATION: Xaa can be any amino acid

<400> SEQUENCE: 34

Xaa Xaa Xaa Xaa Asn His Xaa Xaa Xaa
1               5

<210> SEQ ID NO 35
<211> LENGTH: 433

```
<212> TYPE: PRT
<213> ORGANISM: artificial
<220> FEATURE:
<223> OTHER INFORMATION: human IgE constant region

<400> SEQUENCE: 35
```

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 |

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr Phe Ser Val Ser Ser Arg
            100                 105                 110

Asp Phe Thr Pro Pro Thr Val Lys Ile Leu Gln Ser Ser Cys Asp Gly
            115                 120                 125

Gly Gly His Phe Pro Pro Thr Ile Gln Leu Leu Cys Leu Val Ser Gly
        130                 135                 140

Tyr Thr Pro Gly Thr Ile Asn Ile Thr Trp Leu Glu Asp Gly Gln Val
145                 150                 155                 160

Met Asp Val Asp Leu Ser Thr Ala Ser Thr Thr Gln Glu Gly Glu Leu
                165                 170                 175

Ala Ser Thr Gln Ser Glu Leu Thr Leu Ser Gln Lys His Trp Leu Ser
            180                 185                 190

Asp Arg Thr Tyr Thr Cys Gln Val Thr Tyr Gln Gly His Thr Phe Glu
            195                 200                 205

Asp Ser Thr Lys Lys Cys Ala Asp Ser Asn Pro Arg Gly Val Ser Ala
            210                 215                 220

Tyr Leu Ser Arg Pro Ser Pro Phe Asp Leu Phe Ile Arg Lys Ser Pro
225                 230                 235                 240

Thr Ile Thr Cys Leu Val Val Asp Leu Ala Pro Ser Lys Gly Thr Val
                245                 250                 255

Asn Leu Thr Trp Ser Arg Ala Ser Gly Lys Pro Val Asn His Ser Thr
            260                 265                 270

Arg Lys Glu Glu Lys Gln Arg Asn Gly Thr Leu Thr Val Thr Ser Thr
            275                 280                 285

Leu Pro Val Gly Thr Arg Asp Trp Ile Glu Gly Glu Thr Tyr Gln Cys
            290                 295                 300

Arg Val Thr His Pro His Leu Pro Arg Ala Leu Met Arg Ser Thr Thr
305                 310                 315                 320

Lys Thr Ser Gly Pro Arg Ala Ala Pro Glu Val Tyr Ala Phe Ala Thr
            325                 330                 335

Pro Glu Trp Pro Gly Ser Arg Asp Lys Arg Thr Leu Ala Cys Leu Ile
            340                 345                 350

Gln Asn Phe Met Pro Glu Asp Ile Ser Val Gln Trp Leu His Asn Glu
            355                 360                 365

Val Gln Leu Pro Asp Ala Arg His Ser Thr Thr Gln Pro Arg Lys Thr
            370                 375                 380

```
Lys Gly Ser Gly Phe Phe Val Phe Ser Arg Leu Glu Val Thr Arg Ala
385                 390                 395                 400

Glu Trp Glu Gln Lys Asp Glu Phe Ile Cys Arg Ala Val His Glu Ala
            405                 410                 415

Ala Ser Pro Ser Gln Thr Val Gln Arg Ala Val Ser Val Asn Pro Gly
            420                 425                 430

Lys

<210> SEQ ID NO 36
<211> LENGTH: 332
<212> TYPE: PRT
<213> ORGANISM: artificial
<220> FEATURE:
<223> OTHER INFORMATION: constant IgE domains 3 and 4

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Val Ser Ala Tyr Leu Ser Arg Pro
        115                 120                 125

Ser Pro Phe Asp Leu Phe Ile Arg Lys Ser Pro Thr Ile Thr Cys Leu
    130                 135                 140

Val Val Asp Leu Ala Pro Ser Lys Gly Thr Val Asn Leu Thr Trp Ser
145                 150                 155                 160

Arg Ala Ser Gly Lys Pro Val Asn His Ser Thr Arg Lys Glu Glu Lys
                165                 170                 175

Gln Arg Asn Gly Thr Leu Thr Val Thr Ser Thr Leu Pro Val Gly Thr
            180                 185                 190

Arg Asp Trp Ile Glu Gly Glu Thr Tyr Gln Cys Arg Val Thr His Pro
        195                 200                 205

His Leu Pro Arg Ala Leu Met Arg Ser Thr Thr Lys Thr Ser Gly Pro
    210                 215                 220

Arg Ala Ala Pro Glu Val Tyr Ala Phe Ala Thr Pro Glu Trp Pro Gly
225                 230                 235                 240

Ser Arg Asp Lys Arg Thr Leu Ala Cys Leu Ile Gln Asn Phe Met Pro
                245                 250                 255

Glu Asp Ile Ser Val Gln Trp Leu His Asn Glu Val Gln Leu Pro Asp
            260                 265                 270

Ala Arg His Ser Thr Thr Gln Pro Arg Lys Thr Lys Gly Ser Gly Phe
        275                 280                 285

Phe Val Phe Ser Arg Leu Glu Val Thr Arg Ala Glu Trp Glu Gln Lys
    290                 295                 300

Asp Glu Phe Ile Cys Arg Ala Val His Glu Ala Ala Ser Pro Ser Gln
```

```
305                 310                 315                 320
Thr Val Gln Arg Ala Val Ser Val Asn Pro Gly Lys
                325                 330

<210> SEQ ID NO 37
<211> LENGTH: 600
<212> TYPE: DNA
<213> ORGANISM: artificial
<220> FEATURE:
<223> OTHER INFORMATION: Plasmid DNA Sequence of soluble Fc epsilon RI

<400> SEQUENCE: 37
atgggtgaca  atgacatcca  ctttgccttt  ctctccacag  gtgtccagtc  cgtccctcag    60
aaacctaagg  tctccttgaa  ccctccatgg  aatagaatat  ttaaaggaga  gaatgtgact   120
cttacatgta  atgggaacaa  tttctttgaa  gtcagttcca  ccaaatggtt  ccacaatggc   180
agcctttcag  aagagacaaa  ttcaagtttg  aatattgtga  atgccaaatt  tgaagacagt   240
ggagaataca  aatgtcagca  ccaacaagtt  aatgagagtg  aacctgtgta  cctggaagtc   300
ttcagtgact  ggctgctcct  tcaggcctct  gctgaggtgg  tgatggaggg  ccagcccctc   360
ttcctcaggt  gccatggttg  gaggaactgg  gatgtgtaca  aggtgatcta  ttataaggat   420
ggtgaagctc  tcaagtactg  gtatgagaac  cacaacatct  ccattacaaa  tgccacagtt   480
gaagacagtg  gaacctacta  ctgtacgggc  aaagtgtggc  agctggacta  tgagtctgag   540
cccctcaaca  ttactgtaat  aaaagctccg  cgtgagaagc  accatcacca  ccatcactga   600

<210> SEQ ID NO 38
<211> LENGTH: 3
<212> TYPE: PRT
<213> ORGANISM: artificial
<220> FEATURE:
<223> OTHER INFORMATION: fMLF peptide
<220> FEATURE:
<221> NAME/KEY: MOD_RES
<222> LOCATION: (1)..(1)
<223> OTHER INFORMATION: FORMYLATION

<400> SEQUENCE: 38

Met Leu Phe
1
```

ANTIBODIES DIRECTED TO FC GAMMA RECEPTOR IIB AND FC EPSILON RECEPTOR

An antibody binds to an antigen and neutralizes it by preventing it from binding to its endogenous target (e.g. receptor or ligand) or by inducing effector responses that lead to antigen removal. To efficiently remove and/or destroy antigens foreign to the body, an antibody should exhibit both high affinity for its antigen and efficient effector functions. Antibodies having multispecificities (such as, for example, bispecific antibodies) are useful for mediating complementary or synergistic responses of multiple antigens.

Antibody effector functions are mediated by an antibody Fc region. Effector functions are divided into two categories: (1) effector functions that operate after the binding of antibody to an antigen (these functions involve the participation of the complement cascade or Fc receptor (FcR)-bearing cells); and (2) effector functions that operate independently of antigen binding (these functions confer persistence of antibody in the circulation and its ability to be transferred across cellular barriers by transcytosis). Because Fc receptors mediate antibody effector function by binding to the Fc region of the receptor's cognate antibody, FcRs are defined by their specificity for immunoglobulin isotypes: Fc receptors specific for IgG antibodies are referred to as FcγR; Fc receptors for IgE antibodies are FcεR; Fc receptors for IgA antibodies are FcαR, and so on.

Three subclasses of FcγR have been identified: FcγRI (CD64), FcγRII (CD32), and FcγRIII (CD16). FcγRIIB is characterized by the presence of an ITIM motif (consensus sequence: V/I-X-Y-X$_2$-V/L, Isakov (1997), Immunol Res. 16, 85-100) in the cytoplasmatic domain, which is phosphorylated by the kinase Lyn upon binding of Ig-aggregates or ICs and co-ligation with ITAM-bearing activatory Fcγ receptors. The phosphorylated ITIM attracts the SH2-domain of the inositol polyphosphate 5'-phosphatase (SHIP), which in turn hydrolyzes phosphoinositol messengers released as a consequence of ITAM-containing FcγR-mediated tyrosine kinase activation, consequently preventing influx of intracellular $Ca^{2+}$. Cross-linking of FcγRIIB inhibits the activating response to FcγR ligation which in turn inhibits B cell activation, proliferation and antibody secretion.

Fc epsilon receptors (FcεRs) are found on the surface of mast cells and basophils, as well as on eosinophils, monocytes, macrophages and platelets in humans. There are two types of Fcε receptors, FcεRI (type I Fcε receptor), the high-affinity IgE receptor and FcεRII (type II Fcε receptor), also known as CD23, the low-affinity IgE receptor. IgE can upregulate the expression of both types of Fcε receptors.

Immunoglobulin E (IgE) is a class of antibody (or immunoglobulin (Ig) "isotype") that has been found only in mammals. IgE exists as monomers consisting of two heavy chains (ε chain) and two light chains, with the ε chain containing 4 Ig-like constant domains (Cε1-Cε4). IgE also plays an essential role in type I hypersensitivity (Gould H et al. (2003), Annu. Rev. Immunol. 21: 579-628), which manifests various allergic diseases, such as allergic asthma, most types of sinusitis, allergic rhinitis, food allergy, and some types of chronic urticaria and atopic dermatitis. IgE also plays a pivotal role in allergic conditions, such as anaphylactic reactions to certain drugs, bee stings, and antigen preparations used in specific desensitization immunotherapy.

IgE primes the IgE-mediated allergic response by binding to the FcεRs found on the surface of mast cells and basophils. Binding of antigens to IgE already bound by the FcεRI on mast cells leads to cross-linking of the bound IgE and the aggregation of the underlying FcεRI, leading to the degranulation and the release of mediators from the cells. Basophils, upon the cross-linking of their surface IgE by antigens, release type 2 cytokines like interleukin-4 (IL-4) and interleukin-13 (IL-13) and other inflammatory mediators. The low-affinity receptor (FcεRII) is always expressed on B cells, but its expression can be induced on the surfaces of macrophages, eosinophils, platelets, and some T cells by IL-4.

Mast cells and basophils are important immune regulatory cells and central effector cells in IgE-dependent allergic reactions and in many other acute or chronic inflammatory processes. These cell types have both receptors for IgG and IgE. Activation of the high-affinity receptor for IgE (Fc epsilon RI) on allergic effector cells such as mast cells and basophils induces a multitude of positive signals via immunoreceptor tyrosine-based activation motifs (ITAMs), which leads to the rapid manifestation of allergic inflammatory reactions. As a counterbalance, the coaggregation of the IgG receptor Fc gamma RIIB mediates inhibitory signals via immunoreceptor tyrosine-based inhibition motifs (ITIMs).

Advances in the positive and negative regulation of Fc receptor expression and signaling have shed light on the role of Fc receptors in the immune system, indicating them to be bifunctional, inhibitory and activating structures. Based on these findings, new therapeutic strategies have been developed, such as the use of chimeric fusion proteins, which concomitantly activate Fc epsilon RI and Fc gamma RIIB. These new approaches take advantage of the bivalent character of Fc receptors and pave the way for innovative strategies to modulate allergic immune reactions. An example of such a chimeric fusion protein is disclosed in WO 2002/088317.

However, despite the fact that in the prior art even more such chimeric fusion proteins are known, see also WO 2006/028956, it is nevertheless highly desirable to provide improved chimeric fusion proteins which exert at least two functions—one binding to the Fc epsilon receptor and the second binding to the Fc gamma receptor IIB, thereby coaggregating both receptors.

The present disclosure satisfies this demand by the provision of the recognition molecules described herein below, characterized in the claims and illustrated by the appended Examples and Figures.

Knowing that aggregation of IgE receptor with the IgG receptor (FcγRIIb) on basophils or mast cells inhibits allergen-induced cell degranulation (Daeron (1997), Int. Arch. Allergy Immunol. 113, 138-141), the present inventors provide recognition molecules which, so to say, do not only cross-link or co-aggregate these two receptors with the aim of inhibiting IgE mediated activation of mast cells and basophils, but also enhance the negative regulatory function of Fc gamma RIIB with the aim of improving the treatment of diseases associated with basophils and/or mast cells, such as allergic diseases. As described herein above, activation of the high-affinity receptor for IgE (Fc epsilon RI) on allergic effector cells such as mast cells and basophils leads to the rapid manifestation of allergic inflammatory reactions. As a counterbalance, the co-aggregation of the IgG receptor Fc gamma RIIB mediates inhibitory signals via immunoreceptor tyrosine-based inhibition motifs (ITIMs). The present inventors thus assumed, without being bound by theory, that enhancing/strengthening the known ITIM phosphorylation of Fc gamma RIIB effected by co-aggregation of Fc gamma RIIB and Fc epsilon receptor (see Zhu et al. (2002), Nat. Med. 8(5), 518-521) could be beneficial in counterbalancing or even overcoming the activatory function of the Fc epsilon receptor upon binding of IgE which leads to the release of preformed mediators and synthesis of later acting leukotrienes and chemokines, which all contribute to e.g. allergic disease.

Having this aim in mind, much to their surprise, the present inventors observed that recognition molecules, in particular antibodies, provided by the present disclosure markedly increase ITIM phosphorylation of FcγRIIB and, thus, presumably enhance the inhibitory signal that is already achieved by coaggregating Fc gamma RIIB and Fc epsilon receptor such that it ideally overcomes the activatory signal triggered by activation of the Fc epsilon receptor upon binding of IgE. Thus, recognition molecules, in particular antibodies disclosed herein provide two advantageous functions—they cross-link Fc gamma RIIB and Fc epsilon R which leads to ITIM phosphorylation and thus inhibition of Fc epsilon R signaling, and they enhance as such ITIM phosphorylation of Fc gamma RIIB through their binding to said receptor which once more inhibits Fc epsilon Receptor signaling in basophils and mast cells. There is thus a two-fold effect exerted by recognition molecules, in particular antibodies of the present disclosure on the inhibitory role of Fc gamma RUB mediated signaling in cells that massively contribute to disease associated with mast cells and/or basophils. To take advantage of this Fc gamma RIIB-mediated inhibitory signaling in basophils and mast cells, the present inventors provide the recognition molecules, in particular antibodies, of the present disclosure which in comparison to e.g. antibodies directed against Fc gamma RIIB known in the prior art surprisingly show a much stronger effect on ITIM phosphorylation which could not have been expected. Such stronger effect is advantageous, since it aids in the inhibitory signaling in mast cells and/or basophils so as to inhibit IgE-mediated activation of mast cells and basophils which both play a major role in the onset and manifestation of, e.g. allergic diseases.

As can be seen from FIG. 30, an anti-Fc gamma IIB receptor-IgE antibody disclosed herein is indeed able to reduce the number of activated eosinophils after their activation by pollen (55.1%) to a level that corresponds to untreated eosinophils (10.6% cf. 9.5% of untreated eosinophils). This shows the potency of such an antibody in the negative regulation of cells involved in, e.g., allergic diseases, once these cells have been activated by an allergen via binding of IgE to the allergen and with its Fc domain to the Fc epsilon receptor. Eosinophils along with mast cells and/or basophils are involved in allergic diseases. Accordingly, the inventors' assumption that enhancing/strengthening the known ITIM phosphorylation of Fc gamma RIIB effected by co-aggregation of Fc gamma RIIB and Fc epsilon receptor (see Zhu et al. (2002), Nat. Med. 8(5), 518-521) could be beneficial in counterbalancing or even overcoming the activatory function of the Fc epsilon receptor upon binding of IgE seems indeed to be promising in fighting against, e.g., allergic diseases.

From prior art recognition molecules that bind to Fc gamma RIIB, in particular recognition molecules such as antibodies disclosed herein, the advantageous properties of the polypeptides could neither have been expected nor foreseen, let alone would there have been a reasonable expectation of success to provide them, in particular the CDRs or variable heavy and/or light chain of antibodies as characterized herein. In addition to this improved property, the recognition molecules described herein also have advantageously a high specificity for human FcγRIIB and/or are non-blocking, i.e., that their binding to the Fc receptor via their variable region(s) does not interfere with the binding of immune complexes (ICs) or aggregated IgG to the cells.

Advantageously, a recognition molecule, such as an antibody disclosed herein, binds in "cis" to a cell expressing an Fc epsilon receptor (FcεR) and a Fc gamma receptor IIB (FcγRIIB), i.e., said recognition molecule binds to FcεR and FcγRIIB on the same cell, wherein such cell expresses FcεR and FcγRIIB. This property of a recognition molecule can be readily tested in accordance with the basophil activation test described in Example 5, with the exception that no antigen is added to heparinized whole blood. Briefly, heparinized whole blood is contacted with a recognition molecule disclosed herein. Subsequently, the whole blood is incubated with a detection antibody binding the molecule CD63 on basophil cells in the whole blood, wherein the detection antibody is characterized by a detectable label, e.g. a fluorescence label, and the number of cells expressing CD63 above a threshold level is measured by means of e.g. FACS technique (fluorescence activated cell sorting). A threshold level may be determined on the basis of heparinized whole blood which was not contacted with said recognition molecule (which corresponds to a control). If cells do not express CD63 above threshold level, the recognition molecule binds preferentially in cis, while CD63 expression above threshold level is indicative that a recognition molecule binds to cells in trans, i.e., a recognition molecule binds to FcεR on a first cell and to FcγRIIB on a second cell or to FcγRIIB on a first cell and to FcεR on a second cell. However, as said, in the context of the present disclosure, cis-binding recognition molecules are preferred.

Accordingly, the present disclosure provides recognition molecules that bind with a first binding domain to the Fc epsilon receptor (FcεR) and with a second binding domain to the Fc gamma receptor IIB (FcγRIIB).

Recognition molecules of the present disclosure are deemed to compete with the body's own pathogenic IgE antibodies for binding to the Fc epsilon receptor RI (FcεRI) via their Fc part and simultaneously co-crosslink FcεRI with FcγRIIB. This mode of action is deemed to prevent mediator release from mast cells and/or basophils independent from the allergen specificity of the bound IgE. This mechanism has been characterized by the present inventors, for example, by using FcεRI-expressing basophils from atopic donors (i.e. donors having a predisposition towards the development of hypersensitive immune reactions in response to allergens). The allergen-challenged basophils of the aforementioned atopic donors treated with a recognition molecule disclosed herein exhibited a significantly reduced activation compared to the control as is demonstrated in the appended Examples.

A "recognition molecule" when used herein is a polypeptide which comprises one or more binding domains with a first binding domain that binds to Fc epsilon receptor (FcεR) and with a second binding domain that binds to the Fc gamma receptor IIB (FcγRIIB). A recognition molecule provides the scaffold for said one or more binding domains so that said binding domains can bind/interact with a given target structure/antigen/epitope. For example such a scaffold could be provided by protein A, in particular the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain, or thioredoxin (Skerra, Curr. Opin. Biotechnol. 18, 295-304 (2005); Hosse et al., Protein Sci. 15, 14-27 (2006); Nicaise et al., Protein Sci. 13, 1882-1891 (2004); Nygren and Uhlen, Curr. Opin. Struc. Biol. 7, 463-469 (1997)). A preferred recognition molecule is an antibody.

The binding domains of the recognition molecule of the present invention may be linked via a linker. The linker may be a peptide linker. The linker may comprise (or consist of) 1, 2, 3, 4, 5, 6, 7, 8, 9, 10, 11, 12, 13, 14, 15, 16, 17, 18, 19, 20 or more amino acids. Preferred examples of peptide linkers are $(G_4S)_n$, with n being an interval in the range of 1 to 5; $(AP)_2$; $(AP)_4$; $(AP)_{5-7}$.

The term "binding domain" characterizes in connection with the present disclosure a domain which is capable of specifically binding to/interacting with a given target epitope or a given target site on its target molecules FcεR and FcγRIIB, respectively. Binding domains can be derived from a binding domain donor such as for example from an antibody or from any of the above-mentioned scaffolds.

The term "binding domain" when used herein encompasses that a binding domain can actively bind a target or can passively be bound, e.g., by a receptor. Accordingly, a binding domain in the sense of the present disclosed molecules can be a ligand of a receptor, such as a Fc receptor.

A preferred binding domain of a recognition molecule is at least a portion of a Fab domain. A "Fab domain" when used herein encompasses (a) heavy and/or light chain variable region(s) or CDRs and/or (a) framework region(s) from the heavy and/or light chain variable region. Thus, it is preferred that (a) variable region(s) such as a heavy and/or light chain variable region, or CDRs and/or (a) framework region(s) of the heavy and/or light chain variable region are comprised by a binding domain as described herein. Thus a recognition molecule preferably comprises as a first and second binding domain a Fab domain, preferably (a) variable region(s) such as a heavy and/or light chain variable region, or CDRs and/or (a) framework region(s) of the heavy and/or light chain variable region.

Another referred binding domain of a recognition molecule is the constant region (or domain) (Fc domain) of an IgG or IgE antibody or portion thereof. A "portion" of a Fc domain when used herein is preferably of such a length that it is bound by its cognate Fc receptor such as the Fc epsilon receptor or Fc gamma IIB receptor.

Thus, a preferred recognition molecule preferably comprises as a first and second binding domain the Fc domain of an IgG or IgE antibody or portion thereof, which portion is bound by the Fc gamma IIB receptor or Fc epsilon receptor, respectively.

Also preferred is that a recognition molecule of the present disclosure comprises as a first binding domain a Fab domain, preferably a variable region such as a heavy and/or light chain variable region, or CDRs and/or framework regions of the heavy and/or light chain variable region which binds to the Fc epsilon receptor and as a second binding domain a Fc domain of IgG or portion thereof which is bound by the Fc gamma IIB receptor.

More preferred is that a recognition molecule of the present disclosure comprises as a first binding domain a Fc domain of IgE or portion thereof which is bound by the Fc epsilon receptor and as a second binding domain a Fab domain, preferably a variable region such as a heavy and/or light chain variable region, or CDRs and/or framework regions of the heavy and/or light chain variable region which binds to the Fc gamma IIB receptor.

The term "epitope" refers to a site on an antigen to which a binding domain specifically binds. An "epitope" is antigenic and thus the term epitope is sometimes also referred to herein as "antigenic structure" or "antigenic determinant". Thus, the binding domain is an "antigen-interaction-site". Said binding/interaction is also understood to define a "specific recognition". A preferred epitope in the sense of the present invention is located within the Fc epsilon receptor and the Fc gamma IIB receptor, respectively. Preferably, such an epitope is located in the extracellular portion of any of these two Fc receptors.

"Epitopes" can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3, or at least 4, and more usually, at least 5, or at least 6, or at least 7, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the binding domain). Typically a conformational epitope comprises an increased number of amino acids relative to a linear epitope. With regard to recognition of conformational epitopes, the binding domain recognizes a three-dimensional structure of the antigen, preferably a peptide or protein or fragment thereof. For example, when a protein molecule folds to form a three-dimensional structure, certain amino acids and/or the polypeptide backbone forming the conformational epitope become juxtaposed enabling the antibody to recognize a three-dimensional epitope only present in the three-dimensional structure. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

A binding domain of a recognition molecule, in particular an antibody of the present invention advantageously specifically binds to FcεR and FcγRIIB, respectively. The terms "(capable of) binding to", "specifically recognizing", "directed to" and "reacting with" mean in accordance with this invention that a binding domain is capable of specifically interacting with one or more, such as at least two, at least three, or at least four amino acids of an epitope.

The term "Fc gamma receptor IIB" is used herein interchangeably with "FcgRIIB" or "Fc gamma receptor IIB" or "Fcγ receptor IIB" or "FcγRIIB" and comprises both membranous FcγRIIB and soluble FcγRIIB (i.e. the extracellular part of a Fcγ IIB receptor). Said term also includes variants of FcγRIIB such as FcγRIIB1 and FcγRIIB2 which differ from each other in a 19 amino acid sequence insertion in the cytoplasmic domain of FcγRIIB1. Another variant encompassed by said term is FcγRIIB3 which is identical to FcγRIIB2, but lacks information for the putative signal peptidase cleavage site.

Sometimes, FcγRIIB is also referred to herein as "CD32B". Thus this term as well as the other terms used to designate Fc gamma receptor IIB as described above, can be interchangeably used with the term "CD32B". Fc gamma receptor IIB belongs to the immunoglobulin superfamily of proteins and is found on many hematopoietic lineages. As its name indicates, Fc receptor IIB recognizes and binds to the Fc (fragment, crystallizable) part of antibodies, i.e. the fragment that corresponds to the two C-terminal domains of both heavy chains of the antibody and typically interacts with effector molecules and cells. A preferred FcγRIIB is shown in SEQ ID NO. 5. A preferred soluble FcγRIIB is shown in SEQ ID NO. 12.

"Soluble FcγRIIB" is also referred to as "sFcγRIIB". As used herein, the term "soluble Fcγ receptor IIB" and analogous terms refer to the extracellular part of the Fcγ receptor IIB. Such part can be dissolved in a liquid. In general, soluble forms of any FcγR class, isoform or allele can be identified by a preceding "s", e.g., sCD32 or sFcγRII refers to the soluble Fc gamma RH receptor. Typically, in contrast to membranous (i.e., membrane-bound) FcγR, soluble FcγR do not comprise a transmembrane region or an intracytoplasmatic tail.

Preferably, an FcγRIIB disclosed is of human origin or a human FcγRIIB. The term "of human origin" is to be construed in its broadest sense. In general, it means that a FcγR (or a region or fragment thereof) resembles or is similar to a human FcγR (i.e., the protein found in the human body) in terms of amino acid sequence and/or structure.

Alternatively, the FcγRIIB "of human origin" can be a recombinant FcγRIIB that is obtained by expression of a recombinant nucleic acid in a host cell, e.g. as described by Sondermann and Jacob (1999), Biol. Chem. 380(6), 717-721. Briefly, a gene of interest is obtained from an organism and introduced into a vector, e.g. a plasmid or a virus, which is then used to transfer the gene into a host cell which expresses the recombinant gene and produces a recombinant protein product. The person skilled in the art will readily know which host cell to select in order to obtain a FcγRIIB that is e.g. suitable for the preparation of a pharmaceutical composition. For example, in some embodiments, an unglycosylated FcγRIIB may be desired. The person skilled in the art may then select a prokaryotic host cell for expression of the FcγRIIB that is devoid of the enzyme machinery necessary for protein glycosylation. In one embodiment the FcγRIIB can be expressed in prokaryotes and subsequently purified and refolded according to the description of WO 00/32767.

In another embodiment FcγRIIB can be also be produced in eukaryotic expression systems. Suitable systems include eukaryotes with a specialized apparatus for the production of extracellular proteins, e.g., B cells. Other possible eukaryotic expression systems include, but are not limited to, CHO or HEK cells. Said soluble FcγRIIB is therefore recombinant, soluble and glycosylated FcγRIIB.

FcγRIIB as referred to herein further encompasses FcγRIIB that, in comparison to wild type FcγR, has been modified or altered with regard to the amino acid sequence, and include, e.g., additional glycosylation sites or the like. However, non-glycosylated forms of FcγRIIB are also envisioned and are a useful embodiment of FcγRIIBs.

For the purposes of the present disclosure, FcεR includes both FcεRI and FcεRII. Also used herein are terms such "Fc epsilon R" or "Fc epsilon receptor" which all designate a receptor that binds a constant region or portion thereof of IgE. All these terms can thus be used interchangeably.

A preferred first and second binding domain of the recognition molecule of the present disclosure is derived from an antibody, preferably said first and/or second binding domain is a portion of an antibody, such as Fab domain(s), heavy and/or light chain variable region(s), or CDRs and/or frameworks from the heavy and/or light chain variable region of an antibody.

It is alternatively preferred that a binding domain in the sense of the presently disclosed recognition molecules may be a constant region (constant domain) or at least a portion thereof that is bound by a Fc receptor, such as the Fc epsilon receptor or Fc gamma receptor IIB. Thus, it is a preferred embodiment that both the first and second binding domain may be a constant region or at least a portion thereof of an antibody, such as the Fc region of an IgG or Fc region of IgE that is bound by a Fc receptor, such as the Fc epsilon receptor or Fc gamma receptor. Accordingly, the first binding domain may preferably be the Fc region of IgE or a portion thereof that is bound by the Fc epsilon receptor. The second binding domain may preferably be the Fc region of IgG or a portion thereof that is bound by the Fc gamma RII receptor.

Alternatively, the first binding domain may preferably be at least a portion of an antibody that binds to the Fc epsilon receptor and the second binding domain may be at least a portion of an IgG constant region or portion thereof that is bound by the Fc gamma IIB receptor. Such a molecule is a useful recognition molecule and is to be regarded as an antibody disclosed herein, i.e., it has variable domains and a constant region, such as an IgG Fc region.

Likewise, the first domain may preferably be at least a portion of an IgE constant region or portion thereof that is bound by the Fc epsilon receptor and the second domain may be at last a portion of an antibody that binds to the Fc gamma IIB receptor. Such a molecule is a useful recognition molecule and is in one embodiment an antibody disclosed herein, i.e., it has variable domains and a constant region, such as an IgE Fc region.

In case, the second binding domain (binding to Fc gamma IIB receptor) of a recognition molecule as described herein is a portion of a Fab domain, it is preferred that it comprises in its heavy chain variable region H-CDR1, H-CDR2 and H-CDR3 as shown in SEQ ID NOs. 29, 30 and 31 and in its light chain variable region L-CDR1, L-CDR2 and L-CDR3 shown in SEQ ID NOs. 32, 33 and 34, wherein a recognition molecule, preferably an antibody having a second binding domain as defined before, increases ITIM phosphorylation of FcγRIIB of Daudi cells about 4 to 10-fold in comparison to Daudi cells not treated with said recognition molecule.

It is apparent from FIG. 7 that prior art antibodies GB3 (see WO 2005/051999) and 2B6 (see WO 2004/016750) are not able to increase ITIM phosphorylation of FcγRIIB as can be increased by a recognition molecule, preferably an antibody disclosed herein, such as 8A6—either as chimeric or humanized 8A6 antibody. The ability or inability, respectively, to increase ITIM phosphorylation of FcγRIIB seems thus to be dependent on the CDRs, particularly on some key amino acid residues which are present in 8A6, but not in GB3 and/or 2B6, respectively. Hence, amino acids that are only present in CDRs of 8A6 at positions that correspond to the respective positions within a CDR of 2B6 or GB3 may be regarded as "key residues".

Visual comparison of the CDRs from 2B6, GB3 and 8A6 for key residues reveals that in H-CDR1 the amino acid sequence shown in SEQ ID NO. 29, in H-CDR2 the amino acid sequence shown in SEQ ID NO. 30, in H-CDR3 the amino acid sequence shown in SEQ ID NO. 31, in L-CDR1 the amino acid sequence shown in SEQ ID NO. 32, in L-CDR2 the amino acid sequence shown in SEQ ID NO. 33 and in L-CDR3 the amino acid sequence shown in SEQ ID NO. 34 is beneficially present.

The differences between the amino acid sequences of the CDRs of 8A6, GB3 and 2B6 can also be expressed as degree identity (in %-identity) that is allowed in the CDRs of an antibody disclosed herein when using the CDRs of 8A6 as reference sequences. Accordingly, an H-CDR1 of a second binding domain of the present invention is preferably characterized as being 60% or more, such as 70%, 80% or 90% identical to the H-CDR1 as shown in SEQ ID NO. 20.

In certain embodiments, an H-CDR2 of a second binding domain disclosed herein is characterized as being 36% or more, such as 40%, 50%, 60%, 70%, 80%, or 90% identical to the H-CDR2 as shown in SEQ ID NO. 21.

In certain embodiments, an H-CDR3 of a second binding domain of disclosed herein is characterized as being 50% or more, such as 60%, 70%, 80%, or 90% identical to the H-CDR3 as shown in SEQ ID NO. 22.

In certain embodiments, an L-CDR1 of a second binding domain disclosed herein is characterized as being 64% or more, such as 70%, 80%, or 90% identical to the L-CDR1 as shown in SEQ ID NO. 23.

In certain embodiments, an L-CDR2 of a second binding domain of disclosed herein is characterized as being 29% or more, such as 30%, 40%, 50%, 60%, 70%, 80%, or 90% identical to the L-CDR2 as shown in SEQ ID NO. 24.

In certain embodiments, an L-CDR3 of a second binding domain disclosed herein is characterized as being 78% or more, such as 80%, or 90% identical to the L-CDR3 as shown in SEQ ID NO. 25.

Accordingly, the present disclosure provides in certain embodiments a recognition molecule having a second binding domain (binding to Fc gamma IIB receptor) which comprises in its heavy chain variable region an H-CDR1 sequence which is 60% or more identical to the H-CDR1 sequence shown in SEQ ID NO. 20, an H-CDR2 sequence which is 36% or more identical to the H-CDR2 sequence shown in SEQ ID NO. 21, an H-CDR3 sequence which is 50% or more identical to the H-CDR3 sequence shown in SEQ ID NO. 22, a L-CDR1 sequence which is 64% or more identical to the L-CDR1 sequence shown in SEQ ID NO. 23, a L-CDR2 sequence which is 29% or more identical to the L-CDR2 sequence shown in SEQ ID NO. 24, and a L-CDR3 sequence which is 78% or more identical to the L-CDR3 sequence shown in SEQ ID NO. 25.

In some embodiments, a recognition molecule, such as an antibody, still comprises in the heavy and light chain variable region CDRs of its second binding domain the "key residues" as defined in SEQ ID NOs. 29, 30, 31 (H-CDRs) and as defined in SEQ ID NOs. 32, 33 and 34 (L-CDRs).

A recognition molecule with such a second binding domain increases ITIM phosphorylation of FcγRIIB of Daudi cells about 4 to 10-fold in comparison to Daudi cells not treated with said recognition molecule.

As used herein, the term "% identity" refers to the percentage of identical amino acid residues at the corresponding position within the sequence when comparing two amino acid sequences with an optimal sequence alignment as exemplified by the ClustalW or X techniques as available from www.clustal.org, or equivalent techniques. For example, in case of CDR alignments, each of the CDRs (from the heavy and light chain variable region, respectively) shown in SEQ ID NOs. 20-25 serves as reference sequence for a CDR sequence of interest of a heavy or light chain variable region, respectively, e.g. H-CDR1 of SEQ ID NO. 20 is aligned with an H-CDR1 of interest. Accordingly, both sequences (reference sequence and sequence of interest) are aligned, identical amino acid residues between both sequences are identified and the total number of identical amino acids is divided by the total number of amino acids (amino acid length) of SEQ ID NO. 20, 21, 22, 23, 24, or 25, respectively, dependent on whether H-CDR1, H-CDR2, H-CDR3, L-CDR1, L-CDR2, or L-CDR3 are aligned. The result of this division is a percent value, i.e. percent identity value/degree.

The same procedure for comparing two variable regions with respect to their degree identity is applied, mutatis mutandis.

The H-CDR1 sequences shown in SEQ ID NOs. 14 and 20 are exemplary species sequences of the H-CDR1 shown in SEQ ID NO. 29.

The H-CDR2 sequences shown in SEQ ID NOs. 15 and 21 are exemplary species sequences of the H-CDR2 shown in SEQ ID NO. 30.

The H-CDR3 sequences shown in SEQ ID NOs. 16 and 22 are exemplary species sequences of the H-CDR3 shown in SEQ ID NO. 31.

The L-CDR1 sequences shown in SEQ ID NOs. 17 and 23 are exemplary species sequences of the L-CDR1 shown in SEQ ID NO. 32.

The L-CDR2 sequences shown in SEQ ID NOs. 18 and 24 are exemplary species sequences of the L-CDR2 shown in SEQ ID NO. 33.

The L-CDR3 sequences shown in SEQ ID NOs. 19 and 25 are exemplary species sequences of the L-CDR3 shown in SEQ ID NO. 34.

Accordingly, provided herein is a recognition molecule with a second binding domain (binding to Fc gamma IIB receptor) which
  (a) comprises in its heavy chain variable region H-CDR1, H-CDR2 and H-CDR3 as shown in SEQ ID NOs. 14, 15 and 16 and in its light chain variable region L-CDR1, L-CDR2 and L-CDR3 shown in SEQ ID NOs. 17, 18 and 19; or
  (b) comprises in its heavy chain variable region H-CDR1, H-CDR2 and H-CDR3 as shown in SEQ ID NOs. 20, 21 and 22 and in its light chain variable region L-CDR1, L-CDR2 and L-CDR3 shown in SEQ ID NOs. 23, 24 and 25,
  wherein said recognition molecule preferably increases ITIM phosphorylation of FcγRIIB of Daudi cells about 4 to 10-fold in comparison to Daudi cells not treated with said recognition molecule.

A recognition molecule (binding to Fc gamma IIB receptor) with a second binding domain comprising in its heavy chain variable region H-CDR1, H-CDR2 and H-CDR3 as shown in SEQ ID NOs. 14, 15 and 16 and in its light chain variable region L-CDR1, L-CDR2 and L-CDR3 shown in SEQ ID NOs. 17, 18 and 19, or having in its heavy chain variable region H-CDR1, H-CDR2 and H-CDR3 as shown in SEQ ID NOs. 20, 21 and 22 and in its light chain variable region L-CDR1, L-CDR2 and L-CDR3 shown in SEQ ID NOs. 23, 24 and 25 is an exemplary recognition molecule. Such an exemplary recognition molecule preferably increases ITIM phosphorylation of FcγRIIB of Daudi cells about 4 to 10-fold in comparison to Daudi cells not treated with said recognition molecule.

In one embodiment, the recognition molecule (binding to Fc gamma IIB receptor) has a second binding domain that contains at least (i) a heavy chain variable region comprising an amino acid sequence having at least 80% identity to amino acid sequence SEQ ID NO. 1 and (ii) a light chain variable region comprising an amino acid sequence having at least 65% identity to amino acid sequence SEQ ID NO. 2.

Furthermore, the recognition molecule (binding to Fc gamma IIB receptor) can have a second binding domain that contains at least one of (i) a heavy chain variable region comprising an amino acid sequence having at least 90% identity to amino acid sequence SEQ ID NO. 3 and (ii) a light chain variable region comprising an amino acid sequence having at least 90% identity to amino acid sequence SEQ ID NO. 4.

Such recognition molecules increase ITIM phosphorylation of FcγRIIB of Daudi cells about 4 to 10-fold in comparison to Daudi cells not treated with said recognition molecule.

As described above, an exemplary recognition molecule is an antibody. A preferred antibody is one which binds with a first binding domain, which is at least a portion of a Fab domain, to the Fc epsilon receptor, i.e., an anti-FcεR antibody, preferably of the IgG-type, and with a second binding domain, which is a constant region of IgG or a portion thereof that is bound by the Fc gamma MB receptor to a Fc gamma MB receptor.

Another exemplary antibody binds with a first binding domain which is at least a portion of a Fab domain to the Fc epsilon receptor and with the second binding domain which is at least a portion of a Fab domain to the Fc gamma IIB receptor, i.e., a bifunctional or bispecific anti-FcεR antibody×anti-FcγRIIB antibody. In certain embodiments, the antibody does not bind to the Fc gamma receptor IIA (FcγRIIA).

Also envisioned is an antibody which comprises a Fc domain of IgE or a portion thereof as first binding domain and a Fc domain of IgG or portion thereof as second binding domain.

Another exemplary antibody is one which binds with a first binding domain, which is a constant region of IgE or a portion thereof that is bound by a Fc epsilon receptor to a Fc epsilon receptor, and with a second binding domain, which is at least a portion of a Fab domain, to the Fc gamma IIB receptor, i.e., an anti-FcγRIIB antibody, preferably of the IgG-type. In certain embodiments, the antibody does not bind to the Fc gamma receptor MA (FcγRIIA)

An "antibody" when used herein is a protein comprising one or more polypeptides (comprising one or more binding domains, preferably antigen binding domains) substantially or partially encoded by immunoglobulin genes or fragments of immunoglobulin genes. The term "immunoglobulin" (Ig) is used interchangeably with "antibody" herein. The recognized immunoglobulin genes include the kappa, lambda, alpha, gamma, delta, epsilon, and mu constant region genes, as well as myriad immunoglobulin variable region genes. In particular, an "antibody" when used herein, is typically a tetrameric glycosylated protein composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2, with IgG or IgE being preferred in certain embodiments of the present disclosure. An IgM antibody consists of 5 of the basic heterotetramer unit along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each light chain includes an N-terminal variable (V) domain (VL) and a constant (C) domain (CL). Each heavy chain includes an N-terminal V domain (VH), three or four C domains (CHs), and a hinge region.

The constant domains are not involved directly in binding an antibody to an antigen, but can exhibit various effector functions, such as participation of the antibody dependent cellular cytotoxicity (ADCC). If an antibody should exert ADCC, it is preferably of the IgG1 subtype, while the IgG4 subtype would not have the capability to exert ADCC. The constant domain of a recognition molecule, such as an antibody, can be of each subtype as described herein, with the IgG or IgE subtype preferred, more preferably of the IgE subtype.

When used herein, the term "antibody" does not only refer to an immunoglobulin (or intact antibody), but also refers to a fragment thereof, and encompasses any polypeptide comprising an antigen-binding fragment or an antigen-binding domain such as Fab, F(ab'), F(ab')$_2$, Fv, scFv, Fd, disulfide-linked Fvs (sdFv), and other antibody fragments that retain antigen-binding function as described herein. Typically, such fragments would comprise an antigen-binding domain and have the same properties as the antibodies described herein.

The term "antibody" also includes, but is not limited to, monoclonal, monospecific, poly- or multi-specific antibodies such as bispecific antibodies, humanized, camelized, human, single-chain, chimeric, synthetic, recombinant, hybrid, mutated, grafted, and in vitro generated antibodies, with chimeric or humanized antibodies being preferred. The term "humanized antibody" is commonly defined for an antibody in which the specificity encoding CDRs of HC and LC have been transferred to an appropriate human variable frameworks ("CDR grafting"). The term "antibody" also includes scFvs, single chain antibodies, diabodies or tetrabodies, domain antibodies (dAbs), and nanobodies. In terms of the present invention, the term "antibody" shall also comprise bi-, tri- or multimeric or bi-, tri- or multifunctional antibodies having several antigen binding sites, preferably at least one of them is a FcγRIIB-specific binding site.

Furthermore, the term "antibody" as employed herein also relates to derivatives of the antibodies (including fragments) described herein. A "derivative" of an antibody comprises an amino acid sequence which has been altered by the introduction of amino acid residue substitutions, deletions or additions. Additionally, a derivative encompasses antibodies which have been modified by a covalent attachment of a molecule of any type to the antibody or protein. Examples of such molecules include sugars, PEG, hydroxyl-, ethoxy-, carboxy- or amine-groups but are not limited to these. In effect the covalent modifications of the antibodies lead to the glycosylation, pegylation, acetylation, phosphorylation, amidation, without being limited to these.

The antibody is preferably an "isolated" antibody. "Isolated" when used to describe antibodies disclosed herein, means an antibody that has been identified, separated and/or recovered from a component of its production environment. Preferably, the isolated antibody is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody will be prepared by at least one purification step.

As used herein, the term "specifically binds" refers to recognition molecules, preferably antibodies, or fragments or derivatives thereof, that specifically bind to FcγRIIB or a fragment thereof and do not specifically bind to other Fc receptors. The recognition molecule, preferably the antibodies, or fragments or derivatives thereof, a bind to FcγRIIB through the second binding domain, e.g., through the variable domain of the antibody. However, these recognition molecules, such as antibodies, may also be bound by the Fc gamma RIIB, e.g., through their Fc domain.

The pairing of a VH and VL together forms a single antigen-binding site. The CH domain most proximal to VH is designated as CH1. Each L chain is linked to an H chain by one covalent disulfide bond, while the two H chains are linked to each other by one or more disulfide bonds depending on the H chain isotype. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR 1, CDR2, and CDR3. Accordingly, CDR constituents on the heavy chain are referred to as H1 or H-CDR1, H2 or H-CDR2 and H3 or H-CDR3, while CDR constituents on the light chain are referred to as L1 or L-CDR1, L2 or L-CDR2, and L3 or L-CDR3.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in hypervariable sub-domains of each of the heavy and light chain variable regions. These hypervariable sub-domains are called "complementarity determining regions" (CDRs), of which three make up the binding character of a light chain variable region (L1-CDRL1, L2-CDR and L3-CDR) and three make up the binding character of a heavy chain variable region (H1-CDR, H2-CDR and H3-CDR). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., loc. cit.; Chothia et al., J. Mol. Biol, 1987, 196: 901; and MacCallum et al, J. Mol. Biol, 1996, 262: 732). However, the numbering in accordance with the so-called Kabat system is preferred.

Exemplary variable regions of the second domain (binding to the Fc gamma IIB receptor) of a recognition molecule, such as an antibody, are shown in SEQ ID Nos. 1, 2, 3, and 4.

The term "framework region" refers to the art-recognized portions of an antibody variable region that exist between the more divergent (i.e., hypervariable) CDRs. Such framework regions are typically referred to as frameworks 1 through 4 (FR1, FR2, FR3, and FR4) and provide a scaffold for the presentation of the six CDRs (three from the heavy chain and three from the light chain) in three dimensional space, to form an antigen-binding surface.

Recognition molecules (binding to the Fc gamma IIB receptor), such as antibodies (including fragments and derivatives thereof), advantageously increase ITIM phosphorylation of FcγRIIB of Daudi cells about 1.5, 2, 3, or more-fold, such as about 4-fold or more, about 5-fold or more, about 6-fold or more, about 7-fold or more, about 8-fold or more, about 9-fold or more, or about 10-fold (i.e., even nearly 10-fold) in comparison to Daudi cells not treated with said recognition molecule. For that comparison, the antibody, is, used in an amount within the range of 5 µg/ml to 50 µg/ml, such as 10, 15, 20, or 25 µg/ml.

From the results shown in FIGS. 6, 7 and 8, it is apparent that either the chimeric 8A6 (ch8A6) antibody (comprising rat variable regions and a human constant region) or the humanized 8A6 antibody (hu8A6) markedly increase ITIM phosphorylation in comparison to the prior art antibody GB3. Bearing in mind that the CDRs between the chimeric and humanized 8A6 antibodies are nearly identical, while their framework regions (FRs) are different, and the potency of both antibodies to increase ITIM phosphorylation of FcγRIIBs is nearly the same (see FIG. 8), it is reasonable to conclude that the CDRs are causative for an advantageous property of the antibodies disclosed herein to markedly increase ITIM phosphorylation, for example, in comparison to the prior art antibody GB3.

The skilled person is readily in a position to graft the CDRs as described herein for the second binding domain of a recognition molecule into an appropriate framework or, vice versa, graft framework regions into a second binding domain of a recognition molecule, such as an antibody having the CDRs as described herein such that the thus-resulting recognition molecule, such as an antibody, has the advantageous properties, in particular the property of increasing ITIM phosphorylation of CD32B as described herein.

As mentioned, recognition molecules, such as the antibodies disclosed herein, have the property to increase ITIM phosphorylation of FcγRIIB (CD32B) of Daudi cells in comparison to the prior art antibody GB3 described in WO 2005/051999, which is characterized as having the variable region of the heavy chain shown in SEQ ID NO: 7 of WO 2005/051999 (see SEQ ID NO. 26) and the variable region of the light chain shown in SEQ ID NO: 5 of WO 2005/051999 (see SEQ ID NO. 27).

The increase in ITIM phosphorylation of FcγRIIB (CD32B) of Daudi cells effected by a recognition molecule, such as an antibody, is about 4-fold or more, about 5-fold or more, about 6-fold or more, about 7-fold or more, about 8-fold or more, about 9-fold or more, or about 10-fold (i.e., even nearly 10-fold) in comparison to Daudi cells not treated with said recognition molecule.

ITIM phosphorylation of CD32B (Fc gamma IIB receptor) of Daudi cells is preferably determined as follows:

$3 \times 10^5$ Daudi cells suspended in RPMI 1640 medium supplemented with 1% FBS (fetal bovine serum) are either left untreated (control) or incubated for 25 minutes at 37° C., 5% $CO_2$ with an antibody mix containing mouse anti-human IgM (α-hIgM) and rabbit anti-mouse IgG (α-mIgG) wherein the antibody mix comprises 2 µg/ml α-hIgM (mAB, clone UHB) and 20 µg/ml α-mIgG. Subsequently the cells are either treated 20 minutes at 37° C., 5% $CO_2$ with a recognition molecule, such an antibody disclosed herein, or with a molecule of interest as defined herein below, such as the GB3 antibody of WO 2005/051999, respectively, both a recognition molecule and a molecule of interest are preferably applied at equal concentration, and optionally with buffer as control (w/o). Cells are harvested after incubation at 4° C., lysed and subjected to Western Blot-analysis, whereby phosphorylation is detected by an anti-phosphotyrosine antibody (anti-CD32B (phospho Y292) antibody). The Western Blot is optionally probed with an antibody detecting e.g., β-actin which serves as loading control for Western Blot-analysis. As an alternative to Daudi cells, PBMCs or Raji cells can be used. Accordingly, in all embodiments which apply Daudi cells when determining ITIM phosphorylation Daudi cells can be replaced by Raji cells or PBMCs.

The phosphotyrosine antibody is preferably coupled to a signal generating group. A signal generating group refers to a composition detectable by spectroscopic, photochemical, biochemical, immunochemical, or chemical means. For example, useful labels include radiolabels such as $^{32}P$, $^{35}S$, or $^{125}I$; fluorescent dyes (for example, Cy-3, Cy-5); chromophores, electron-dense reagents; enzymes that generate a detectable signal (e.g., as commonly used in an ELISA); or spin labels. The label or detectable moiety has or generates a measurable signal, such as a radioactive, chromogenic, or fluorescent signal, that can be used to quantify the amount of bound detectable moiety in a sample.

The signal generating group can be covalently or non-covalently bound to the phosphotyrosine antibody. A signal can be determined by way of the signal provided by the signal generating group of a phosphotyrosine antibody. The signal can be any signal which is detectable by, for example, spectroscopic, photochemical, biochemical, immunochemical, or chemical means.

An increase in ITIM phosphorylation is determined by comparing (i) the signal generated from the signal generating group of the phosphotyrosine antibody bound to the ITIM motif of CD32B of cells that were untreated ("reference value") to (ii) the signal generated from the signal generating group of the phosphotyrosine antibody bound to the ITIM motif of CD32B of cells that were treated with a recognition molecule, such as an antibody disclosed herein, whereby if signal (ii) is higher than signal (i) an increase in ITIM phosphorylation of CD32B was effected by a recognition molecule, disclosed herein. For that comparison, a recognition molecule is used in an amount within the range of about 5 μg/ml to about 50 μg/ml, such as 10, 15, 20, or 25 μg/ml. For example, when comparing the prior art antibody GB3 or any other molecule such as an antibody binding to CD32B (collectively called "molecule of interest"), such as one that binds the epitope on CD32B as described herein, and/or that is non-blocking as described herein with a recognition molecule, in order to determine the ability of a molecule of interest and a recognition molecule, to increase ITIM phosphorylation of CD32B, ITIM phosphorylation is determined as described above for the molecule of interest and a recognition molecule. Namely, a value for the comparison of a molecule of interest with untreated cells and a value for the comparison of a recognition molecule with untreated cells is obtained. These values can be compared to each other in order to determine whether a recognition molecule has the ability to increase ITIM phosphorylation to a higher extent, such as 4 to 10-fold (including 4, 5, 6, 7, 8, 9, 10) than a molecule of interest. For that comparison, a molecule of interest and a recognition molecule are used in an amount within the range of 5 μg/ml to 50 μg/ml, such as 10, 15, 20, or 25 μg/ml.

As regards the heavy chain variable region of a second binding domain (binding to Fc gamma IIB receptor) of a recognition molecule disclosed herein, in certain embodiments the heavy chain variable region comprises the amino acid sequence shown in SEQ ID NO. 3, with at least one of the mutations selected from the group consisting of amino acid Q at position 1 being replaced by E, amino acid V at position 11 being replaced by L, amino acid G at position 42 being replaced by K, amino acid S at position 50 being replaced by V, amino acid Y at position 53 being replaced by S, amino acid K at position 58 being replaced by T, amino acid G at position 61 being replaced by A, amino acid S at position 75 being replaced by T, amino acid K at position 76 being replaced by R, amino acid N at position 77 being replaced by S, and amino acid T at position 78 being replaced by N. Such an antibody is characterized as comprising an IgE constant domain as first binding domain.

In case the second binding domain of a recognition molecule is a constant domain of IgG or portion thereof that is bound by the Fc gamma IIB receptor, a recognition molecule is characterized as comprising the heavy chain constant region the amino acid sequence shown in SEQ ID NO. 6 and/or the light chain constant region the amino acid sequence shown in SEQ ID NO. 7.

In an antibody disclosed herein, the constant region of the heavy chain contains an alanine residue at position 297 (N297A) according to the EU protein numbering as described by Edelman et al. 1969 (corresponds to the numbering of the sequence which is represented by SEQ ID NO.6 as shown in FIG. 2). Antibodies with a heavy chain containing an alanine (Ala, A) residue at position 297 (N297A) are designated herein with the suffix "_N297A", while antibodies having an asparagine (Asn, N) residue at said position are "wildtype" and are thus designated herein with the suffix "(wt)". As can be seen in FIG. 2, the variable region of the heavy chain of the humanized antibody 8A6 wild type ends with an amino acid residue "S" at position 113 according to the EU protein numbering. The constant region of said antibody starts at position 118. The resulting apparent gap of 4 amino acid residues is caused by the switch to the EU protein numbering system for the constant region and does not mean that any amino acid residues are missing.

Such constant domains which have an alanine residue at position 297 of the amino acid sequence represented by SEQ ID NO.6 do have a reduced or no antibody dependent cellular cytotoxicity due to a reduced or non-existent binding of the Fc part of the antibody to Fc receptors. The amino acid sequence of such a N297A constant region is shown in SEQ ID NO. 28. Accordingly, recognition molecules disclosed herein may contain as constant region the amino acid sequence shown in SEQ ID NO. 28. Such antibodies lack glycosylation at position 297 according to the EU protein numbering. Thus, disclosed herein are antibodies that lack glycosylation at position 297 according to the EU protein numbering of the heavy chain constant region, and also encompass antibodies that are glycosylated at position 297 according to the EU protein numbering of the heavy chain constant region.

In some embodiments, the constant domain (Fc-domain) of a recognition molecule, such as an antibody disclosed herein, has the allotype G1m17 containing the amino-acids K (Lys) at position 214, E (Glu) at position 356, M (Met) at position 358 and A (Ala) at position 431, lacking a C-terminal K (Lys) (Beck et al., 2010).

In case the second binding domain of a recognition molecule is a constant domain of IgG or portion thereof that is bound by the Fc gamma IIB receptor, the constant light domain is of the Km3 allotype may comprise amino-acids A (Ala) at position 153 and V (Val) at position 191.

As used herein, the term "allotype" refers to the human allotype of the antibodies disclosed herein. Allotypes are allelic/genetic variants within the constant-region sequences of particular isotypes. The allotypes are inherited in an allelic manner. Different members of a species will therefore differ from one another with respect to which particular alleles of a given isotype they inherited from their parents. Km1 and Km2 are allotypes of humans kappa chains; G1m(4) and G1m(17) are allotypes of human gamma-1 chains.

In case the second binding domain of a recognition molecule is a constant domain of IgG or portion thereof that is bound by the Fc gamma IIB receptor, a recognition molecule may comprise the heavy chain constant region the amino acid sequence shown in SEQ ID NO. 6 and the light chain constant region the amino acid sequence shown in SEQ ID NO. 7. Such a recognition molecule is characterized by a first binding domain being an IgE constant domain or portion thereof that is bound by the Fc epsilon receptor.

As regards the light chain variable region of a second binding domain (binding to Fc gamma IIB receptor) of a recognition molecule, in some embodiments it comprises the amino acid sequence shown in SEQ ID NO. 4, with at least one of the mutations selected from the group consisting of amino acid Q at position 1 being replaced by N, amino acid S at position 28 being replaced by N, amino acid S at position 31 being replaced by T, amino acid V at position 33 being replaced by L, amino acid D at position 34 being replaced by A, amino acid Y at position 49 being replaced by F, amino acid T at position 53 being replaced by N, amino acid Y at position 55 being replaced by A, amino acid L at position 89 being replaced by Q, and amino acid N at position 93 being replaced by Y. Such an antibody is characterized as comprising the heavy chain constant region the amino acid sequence shown in SEQ ID NO. 6 and/or the light chain constant region the amino acid sequence shown in SEQ ID NO. 7. Such a recognition molecule is further characterized by a first binding domain being an IgE constant domain or portion thereof that is bound by the Fc epsilon receptor.

A recognition molecule (binding to Fc gamma IIB receptor), such as an antibody, comprises the heavy chain variable region shown in SEQ ID NO. 1 or 3 and/or the light chain variable region shown in SEQ ID NO. 2 or 4. Accordingly, a recognition molecule may comprise the heavy chain variable region shown in SEQ ID NO. 1 and the light chain variable region shown in SEQ ID NO. 2 or it comprises the heavy chain variable region shown in SEQ ID NO. 3 and the light chain variable region shown in SEQ ID NO. 4.

An recognition molecule (binding to Fc gamma IIB receptor), such as an antibody disclosed herein, specifically binds to an epitope within amino acids No. 20-40 of human FcγRIIB according to SEQ ID NO. 5.

In some embodiments, the recognition molecule specifically binds to an epitope comprising the motif GTHSPES in SEQ ID NO. 5. This amino acid motif has been shown to be a very specific epitope of FcγRIIB. Recognition molecules, such as antibodies which bind specifically to this epitope, do not bind to human FcγRIIA. Binding of a recognition molecule, such as an antibody, to this epitope via its variable region(s) does preferably not interfere with binding of Fc parts of antibodies to the receptor and does not block the normal physiological function of the receptor.

In some embodiments, the recognition molecule (binding to Fc gamma IIB receptor), such as an antibody, binds in vitro human FcγRIIb with an affinity having an off-rate constant of at least $4.9 \times 10^{-4}$ s$^{-1}$. An off-rate constant ($k_{off}$) can be measured by surface plasmon resonance experiments. Especially, antibody binding to sFcγRIIB can be analysed by surface plasmon resonance using a BIAcore T200 biosensor (GE Healthcare/Biacore).

As used herein, the term "affinity" refers to the binding strength between the variable regions of one heavy and one light chain of an antibody or fragment or derivative thereof and their antigen (e.g. the FcγRIIB receptor) and is measured in vitro. Affinity determines the strength of the interaction between an epitope and an antibody's antigen binding site. Affinity can be calculated using the following formula:

$$KA=[AB-AG]/[AB]*[AG]=k_{on}/k_{off}$$

wherein:
KA=affinity constant
[AB]=molar concentration of unoccupied binding sites on the antibody
[AG]=molar concentration of unoccupied binding sites on the antigen
[AB−AG]=molar concentration of the antibody-antigen complex As used herein, the term "avidity" refers to the measurement of the overall strength of an antibody-antigen complex, which in effect depends on the parameters (1) affinity of the antibody for the epitope, (2) valency of the antibody and antigen and (3) the structural arrangement of the interacting parts.

It is envisaged that a recognition molecule, which is preferably an antibody, can be glycosylated or deglycosylated.

In case the first binding domain of a recognition molecule disclosed herein is a constant domain of IgE or portion thereof that is bound by the Fc epsilon receptor, it can have the amino acid sequence of SEQ ID NO:35 or 36 or portion thereof.

A preferred portion of a Fc IgE domain comprises domain Cε3 and/or domain Cε4 (see FIG. 15 and SEQ ID NO. 36). These domains are homologous with IgG-Cγ2 and Cγ3. In an IgG antibody the hinge-region is responsible for the required flexibility of the molecule and forming the dimer via disulfide bridges. This hinge-region does not exist in the IgE antibody. Instead of that the extra domain Cε2 adopts this function.

Other exemplary portions of a Fc IgE domain comprise the Cε2, Cε3 and/or Cε4 domain (see FIG. 15 and SEQ ID NOs. 35).

Another variation regards the different amount of N-glycosylation-sites in the Fcε-domain. Several glycosylation sites are described for the IgE molecule: N265, N371, N383 and N394. It is envisaged that one or more of these sites remain as-is or are mutated such that they can no longer be glycosylated.

In addition, in some embodiments, a recognition molecule, such as an antibody, comprises as a first binding domain a Fc domain of IgE and can bind in vitro to human FcεRI with an affinity having at least $1.2 \times 10^{-7}$ Kd (M).

Also provided herein are nucleic acid sequences encoding the recognition molecule described herein. As used herein, the terms "nucleic acids" or "nucleotide sequences" refer to DNA molecules (e.g. cDNA or genomic DNA), RNA (mRNA), combinations thereof or hybrid molecules comprised of DNA and RNA. The nucleic acids can be double- or single-stranded and may contain double- and single-stranded fragments at the same time. Most preferred are double-stranded DNA molecules.

Accordingly, a nucleic acid sequence which codes for a disclosed recognition molecule comprises nucleotides which encode at least those parts of the antibody which confer the specific binding properties of the antibody.

In some embodiments, disclosed nucleic acid sequences encode the variable regions, such as at least the CDRs as described herein.

Exemplary nucleic acid sequences are represented by SEQ ID NOs. 8-11. A person skilled in the art would be aware that these nucleotide sequences can vary depending on the employed methods of expression and systems used therefor.

Further provided herein is a nucleic acid vector comprising at least one of the nucleic acid sequences as described herein that encode a recognition molecule disclosed herein. The vector preferably comprises a promoter under the control of which the above nucleic acid sequences are placed. The vector can be prokaryotic or an eukaryotic expression vector, where the recombinant nucleic acid is either expressed alone or in fusion to other peptides or proteins.

Also disclosed herein is a host cell which is transfected with the vector mentioned above. The host cell can be any cell, a prokaryotic cell or a eukaryotic cell and can be used to produce at least parts of an antibody or fragment or derivative thereof.

Also provided is a method for the production of a recognition molecule, comprising culturing a host cell as described herein under conditions which allow expression of the nucleic acid sequence comprised by the nucleic acid vector and recovering the thus produced recognition molecule.

The recognition molecules disclosed herein can advantageously be used in a pharmaceutical composition. Such pharmaceutical composition can be applied for the treatment or prophylaxis of diseases associated with basophils, preferably allergic disease.

Accordingly, also provided are methods of treatment or prophylaxis of diseases associated with basophils, preferably allergic diseases, said method comprising administering a therapeutically effective amount of a recognition molecule disclosed herein to a subject in need thereof.

"Allergic disease" or "allergy" refers to certain diseases in which immune responses to environmental antigens cause tissue inflammation and organ dysfunction. An allergen is any antigen that causes allergy. As such, it can be either the antigenic molecule itself or its source, such as pollen grain, animal dander, insect venom, or food product. IgE plays a central role in allergic disorders. IgE high affinity receptors (FcεRI) are located on mast cells and basophils, which serve as antigenic targets stimulating the further release of inflammatory mediators producing many of the manifestations of allergic disease.

The term "allergic disease" also encompasses IgE-mediated inflammation. "IgE-mediated inflammation" occurs when antigen binds to the IgE antibodies that occupy the FcεRI receptor on mast cells. Within minutes, this binding causes the mast cell to degranulate, releasing certain preformed mediators. Subsequently, the degranulated cell begins to synthesize and release additional mediators de novo. The result is a two-phase response: an initial immediate effect on blood vessels, smooth muscle, and glandular secretion (immediate hypersensitivity), followed by a few hours later by cellular infiltration of the involved site. IgE-mediated inflammation is the mechanism underlying atopic allergy (such as hay fever, asthma and atopic dermatitis), systemic anaphylactic reactions and allergic urticaria (hives). It may normally play a role as a first line of immunologic defense, since it causes rapid vasodilation, facilitating entry of circulating soluble factors and cells to the site of antigen contact. Many of the most destructive attributes of allergic disease are due to the actions of the chemoattracted leukocytes.

In another aspect, the present disclosure relates to a pharmaceutical composition comprising as an active ingredient a recognition molecule. Said pharmaceutical composition may comprise at least one pharmaceutically acceptable carrier or adjuvant or excipient. Recognition molecules may be provided in pharmaceutically acceptable compositions as known in the art or as listed in a generally recognized pharmacopeia for use in animals, and more particular in humans.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. The compositions can be formulated as neutral or salt forms.

Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The above-mentioned pharmaceutical composition can be used for the treatment or prophylaxis or diagnosis of any disease or disorder, preferably of diseases associated with basophils, preferably allergic disease.

The dosage amounts and frequencies of administration are encompassed by the terms therapeutically effective and prophylactically effective. The dosage and frequency of administration further will typically vary according to factors specific for each patient depending on the specific therapeutic or prophylactic agents administered, the type of disease, the route of administration, as well as age, body weight, response, and the past medical history of the patient. Suitable regimens can be selected by one skilled in the art. As used herein, the term "therapeutically effective amount" refers to an amount of the therapeutic active component or agent which is sufficient to treat or ameliorate a disease or disorder, to delay the onset of a disease or which provides any therapeutic benefit in the treatment or management of a disease.

For antibodies being exemplary recognition molecules encompassed herein, the dosage administered to a patient is typically 0.0001 mg/kg to 100 mg/kg of the patient's body weight. Exemplary administered dosage are about 0.1 to about 30 mg/kg, about 0.1 mg/kg to about 25 mg/kg, about 0.5 mg/kg to about 25 mg/kg, about 1 mg/kg to about 100 mg/kg, about 1 mg/kg to about 75 mg/kg, about 1 mg/kg to about 50 mg/kg, about 5 mg/kg to about 50 mg/kg, about 5 mg/kg to about 40 mg/kg, about 5 mg/kg to about 30 mg/kg, about 5 mg/kg, about 10 mg/kg, about 12 mg/kg, about 14 mg/kg, about 15 mg/kg, about 17 mg/kg, about 20 mg/kg, or about 25 mg/kg. It is well known that human antibodies have a longer half-life within the human body than antibodies from other species. Therefore, the dosage and frequency of administration of antibodies, or fragments or derivatives thereof, may be reduced as compared to normally used dosages of antibodies from other species.

Treatment of a subject with a therapeutically or prophylactically effective amount of antibodies, or fragment or derivative thereof, can include a single treatment or, preferably, can include a series of treatments. In certain embodiments, a subject can be treated with antibodies, or fragments or derivatives thereof, in a range of doses disclosed above, one time per week for between about 1 to about 10 weeks, between about 2 to about 8 weeks, more preferably between about 3 to about 7 weeks. The most advantageous form and manner of application can be chosen to best benefit the patient to be treated.

Methods of administering an antibody, or fragment or derivative thereof, include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent.

As used herein, the term "treating" and "treatment" refers to administering to a subject a therapeutically effective amount of a pharmaceutical composition. A "therapeutically effective amount" refers to an amount of the pharmaceutical composition or the antibody which is sufficient to treat or ameliorate a disease or disorder, to delay the onset of a disease or to provide any therapeutic benefit in the treatment or management of a disease.

As used herein, the term "prophylaxis" refers to the use of an agent for the prevention of the onset of a disease or disorder. A "prophylactic effective amount" defines an amount of the active component or pharmaceutical agent sufficient to prevent the onset or recurrence of a disease.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs.

Moreover, the disclosed antibodies can be used for diagnostic purposes to detect, diagnose, or monitor diseases, or disorders, in particular autoimmune diseases. Antibodies or fragments or derivatives thereof, can be used to assay FcγRIIB levels in a biological sample using classical immunohistological methods as described herein or as known to those of skill in the art (e.g., see Jalkanen et al., 1985, J. Cell. Biol. 101: 976-985; Jalkanen et al., 1987, J. Cell. Biol. 105: 3087-3096). Other antibody-based methods useful for detecting protein gene expression include immunoassays, such as the enzyme linked immunosorbent assay (ELISA) and the radioimmunoassay (RIA).

Therefore, the present disclosure further relates to a diagnostic composition comprising a recognition molecule, preferably an antibody disclosed herein.

SEQUENCES

SEQ ID NO. 1: Amino acid sequence of the heavy chain variable region of the rat antibody 8A6

SEQ ID NO. 2: Amino acid sequence of the light chain variable region of the rat antibody 8A6

SEQ ID NO. 3: Amino acid sequence of the heavy chain variable region of the humanized antibody hu8A6

SEQ ID NO. 4: Amino acid sequence of the light chain variable region of the humanized antibody hu8A6

SEQ ID NO. 5: Amino acid sequence of human FcγRIIB

SEQ ID NO. 6: Amino acid sequence of the heavy chain constant region of the humanized antibody hu8A6_wt SEQ ID NO. 7: Amino acid sequence of the light chain constant region of the humanized antibody hu8A6_wt SEQ ID NO. 8: Nucleic acid sequence encoding the heavy chain variable region of the humanized antibody hu8A6

SEQ ID NO. 9: Nucleic acid sequence encoding the light chain variable region of the humanized antibody hu8A6

SEQ ID NO. 10: Nucleic acid sequence encoding the heavy chain constant region of the humanized antibody hu8A6_wt SEQ ID NO. 11: Nucleic acid sequence encoding the light chain constant region of the humanized antibody hu8A6_wt SEQ ID NO. 12: Amino acid sequence of human soluble FcγRIIA (sFcγRIIA)

SEQ ID NO. 13: Amino acid sequence of mutated human soluble FcγRIIA (sFcγRIIAmut)

SEQ ID NO. 14: Amino acid sequence of CDR1 of the heavy chain variable region of the rat antibody 8A6

SEQ ID NO. 15: Amino acid sequence of CDR2 of the heavy chain variable region of the rat antibody 8A6

SEQ ID NO. 16: Amino acid sequence of CDR3 of the heavy chain variable region of the rat antibody 8A6

SEQ ID NO. 17: Amino acid sequence of CDR1 of the light chain variable region of the rat antibody 8A6

SEQ ID NO. 18: Amino acid sequence of CDR2 of the light chain variable region of the rat antibody 8A6

SEQ ID NO. 19: Amino acid sequence of CDR3 of the light chain variable region of the rat antibody 8A6

SEQ ID NO. 20: Amino acid sequence of CDR1 of the heavy chain variable region of the humanized antibody hu8A6

SEQ ID NO. 21: Amino acid sequence of CDR2 of the heavy chain variable region of the humanized antibody hu8A6

SEQ ID NO. 22: Amino acid sequence of CDR3 of the heavy chain variable region of the humanized antibody hu8A6

SEQ ID NO. 23: Amino acid sequence of CDR1 of the light chain variable region of the humanized antibody hu8A6

SEQ ID NO. 24: Amino acid sequence of CDR2 of the light chain variable region of the humanized antibody hu8A6

SEQ ID NO. 25: Amino acid sequence of CDR3 of the light chain variable region of the humanized antibody hu8A6

SEQ ID NO. 26: Amino acid sequence of the heavy chain variable region of antibody GB3 (see also SEQ ID NO. 7 of WO 2005/051999)

SEQ ID NO. 27 Amino acid sequence of the light chain variable region of antibody GB3 (see also SEQ ID NO. 5 of WO 2005/051999)

SEQ ID NO. 28 Amino acid sequence of a heavy chain constant region containing at position 297 a N to A substitution (assuming that position 1 of the sequence as shown in the sequence listing is position 118)

SEQ ID NO. 29 Amino acid sequence of CDR1 of the heavy chain variable region which comprises key amino acid residues from chimeric and humanized antibody 8A6

SEQ ID NO. 30 Amino acid sequence of CDR2 of the heavy chain variable region which comprises key amino acid residues from chimeric and humanized antibody 8A6

SEQ ID NO. 31 Amino acid sequence of CDR3 of the heavy chain variable region which comprises key amino acid residues from chimeric and humanized antibody 8A6
SEQ ID NO. 32 Amino acid sequence of CDR1 of the light chain variable region which comprises key amino acid residues from chimeric and humanized antibody 8A6
SEQ ID NO. 33 Amino acid sequence of CDR2 of the light chain variable region which comprises key amino acid residues from chimeric and humanized antibody 8A6
SEQ ID NO. 34 Amino acid sequence of CDR3 of the light chain variable region which comprises key amino acid residues from chimeric and humanized antibody 8A6
SEQ ID NO. 35 Amino acid sequence of the Fc domain of IgE containing domains 2, 3 and 4
SEQ ID NO. 36 Amino acid sequence of the Fc domain of IgE containing domains 3 and 4
SEQ ID NO. 37: Plasmid DNA Sequence of sFcεRIα
SEQ ID NO. 38: Amino acid sequence of peptide formyl Methionine-Leucine-Phenylalanine

BRIEF DESCRIPTION OF THE DRAWINGS

FIG. 1: Surface Plasmon Resonance analysis of humanized 8A6 according to SEQ. ID. No. 3 and 4 in either wildtype or N297A format, ch8A6_N297A (according to SEQ. ID. NO. 14 and 15 and chGB3_N297A.

FIG. 2: Sequences of hu8A6_wt and hu8A6_N297A depicting position of N to A amino acid exchange in N297A format.

FIG. 6a: ITIM-Phosphorylation increased by chimeric 8A6 (ch8A6_N297A) in PBMC from healthy donor. PBMC from healthy donor were isolated using Ficoll separation and subsequently left untreated or incubated for 25 minutes with an antibody mix containing anti-IgM (anti-human, mouse) and anti-mouse IgG (rabbit). Subsequently the cells were either treated 20 minutes with 5 μg/mL ch8A6_N297A or buffer as control (w/o). Cells were harvested after incubation and lysed according to protocol. Lysates were subjected to WB-analysis. β-Actin=loading control.

FIG. 6b: Control experiment for ITIM-Phosphorylation. Daudi cells were left untreated or treated for 25 minutes with an isotype control antibody, polyclonal anti-human anti-IgM (polycl. anti-hIgM), monoclonal anti human IgM (anti-hIgM), anti-hIgM+5 μg/mL ch8A6_N297A, anti-mouse IgG from rabbit (α-mouseIgG), α-mouse IgG+5 μg/mL ch8A6_N297A, mix of anti-hIgM and α-mouseIgG (Ab mix) or Ab mix+5 μg/mL ch8A6_N297A). β-Actin=loading control.

FIG. 6c: Antibodies of the present invention enhance ITIM phosphorylation with and without crosslinking/colligation of BCR and Fcgamma RIIB (FcγRIIB) in primary PBMCs.

FIG. 7: Comparison of ch8A6_N297A with antibody from the state of the art (chGB3_N297A). Human Daudi cells were incubated for 25 minutes with an antibody mix containing anti-IgM (anti-human, mouse) and anti-mouse IgG (rabbit) or left untreated. Subsequently the cells were either treated 20 minutes with varying amounts of chGB3_N297A or ch8A6_N297A or buffer as control (w/o). Cells were harvested after incubation and lysed according to protocol. Lysates were subjected to WB-analysis. β-Actin=loading control.

FIG. 9: Co-Immunoprecipitation of phosphorylated SHIP-1 with FcγRIIB ITIM. After stimulation of Daudi cells with the antibody mix and either ch8A6_N297A, blocking anti-FcγRIIB antibody 2B6 or chGB3_N297A (5 μg/mL), FcγRIIB was precipitated from cell lysates and Western Blot analysis was performed for the phosphatase SHIP-1. Anti-CD32 using pan anti-CD32 antibody (AF1330)=loading control.

FIG. 10: Comparison of humanized 8A6 variants (hu8A6-VH10+VL2/VH10+VL6/VH10+VL7/VH12+VL2/VH12+VL6/VH12+VL7) to ch8A6_N297A. Daudi cells were left incubated for 25 minutes with buffer (untreated) or a mix (antibody mix) containing anti-IgM (anti-human, mouse) and anti-mouse IgG (rabbit). Subsequently the cells were either treated 20 minutes with 0.25 μg/mL of ch8A6_N297A or humanized 8A6 variants (hu8A6-VH10+VL2/VH10+VL6/VH10+VL7/VH12+VL2/VH12+VL6/VH12+VL7). Cells were harvested after incubation and lysed according to protocol. Lysates were subjected to WB-analysis. 13-Actin=loading control.

FIG. 11: Comparison of humanized 8A6 variants (hu8A6-VH10+VL2/VH10+VL6/VH 10+VL7/VH12+VL2/VH12+VL6/VH12+VL7) to ch8A6_N297A, blocking anti-FcγRIIB and chGB3_N297A. Daudi cells were left incubated for 25 minutes with buffer (untreated) or a mix (antibody mix) containing anti-IgM (anti-human, mouse) and anti-mouse IgG (rabbit). Subsequently the cells were either treated 20 minutes with 0.25 μg/mL of ch8A6_N297A, humanized 8A6 variants (hu8A6-VH10+VL2/VH10+VL6/VH10+VL7/VH12+VL2/VH12+VL6/VH12+VL7), blocking anti-FcγRIIB antibody 2B6 or chGB3_N297A. Cells were harvested after incubation, lysed according to protocol and analyzed in a Western Blot assay. Lysates were subjected to WB-analysis. β-Actin=loading control.

EXAMPLES—GENERATION OF ANTI-FC GAMMA IIB RECEPTOR ANTIBODIES

Figure 3:
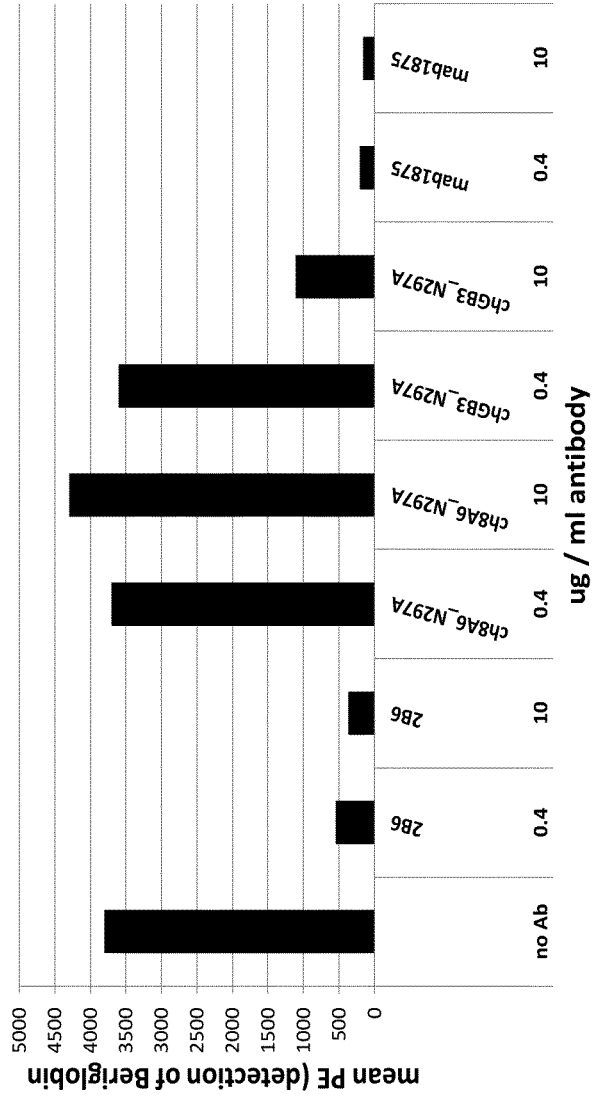
FIG. 3: Non-blocking characteristic of ch8A6_N297A. Raji cells were incubated with a set amount of aggregated human IgG and varying amounts of ch8A6_N297A, chGB3_N297A or blocking antibodies 2B6 or R&D Ab. The antibodies are non-blocking.

Example 1. Preparation of the Monoclonal Antibody 8A6

The monoclonal antibody clone 8A6 was produced by immunizing Long-Evans rats with recombinant soluble human FcγRIIB receptor. Hybridoma cell lines from rat spleen cells were produced and screened for antibodies that specifically bind to human FcγRIIB with greater affinity than to FcγRIIA. Secondly the antibodies produced by the aforementioned hybridomas were screened for non-blocking characteristics, i.e. these antibodies still allow binding of IgG or ICs to membrane-bound FcγRIIB, using techniques known in the art.

50 μg of the purified recombinant soluble human FcγRIIB (sFcγRIIB, SEQ ID NO. 5) were injected intraperitoneally (i.p.) and subcutaneously (s.c.) into LOU/C rats using incomplete Freund's adjuvant supplemented with 5 nmol CpG 2006 (TIB MOLBIOL, Berlin, Germany). After a six weeks interval a final boost with 50 μg sFcγRIIB and CpG 2006 was given i.p. and s.c. three days before fusion. Fusion of the myeloma cell line with the rat immune spleen cells was performed according to standard procedures. Hybridoma supernatants were tested in a solid-phase immunoassay with sFcγRIIB or the irrelevant sFcγRIIA (SEQ ID NO. 12) protein coated to ELISA plates. MAbs from tissue culture supernatant bound to the proteins were detected with HRP conjugated mAbs against the rat IgG isotypes (TIB173 anti-IgG2a, TIB174 anti-IgG2b, TIB170 anti-IgG1 all from ATCC, R-2c anti-IgG2c homemade), thus avoiding mAbs of IgM class. The mAb 8A6 (rat IgG2a) recognized FcγRIIB and did not bind to FcγRIIA using the antigen-specific ELISA assay. A FACS based assay was used to screen the antibodies for specific binding of the native antigen). Additionally the antibodies were screened for non-blocking characteristics, i.e. these antibodies still allow binding of IgG or immune complexes to membrane-bound FcγRIIB.

To produce sufficient amount of antibody for characterization of the chimeric and humanized constructs, FreeStyle™ CHO-S cells were transiently transfected.

The day before transfection cells were seeded at $0.5\times10^6$ cells/ml. Cells were centrifuged and resuspended in medium to obtain a final cell concentration of $20\times10^6$ cells/ml. For each transfection 3 ml of the cell suspension was transferred to a 6-well plate. The plasmid DNA for transfection was isolated using the HiSpeed Plasmid Maxi Kit (Qiagen) according to the manufacturer's instructions and eluted in endotoxin-free $H_2O$.

For each transfection 75 μg plasmid DNA encoding for the light chain and 75 μg plasmid DNA encoding for the heavy chain were added to the cell suspension and mixed gently. Afterwards PEI (Polyplus) was added and mixed gently. The cells were incubated for 3 h at 37° C. and 5% $CO_2$ under continuous shaking (100 rpm). The cell suspension was filled up with medium to a final volume of 15 ml to achieve a final cell concentration of $4\times10^6$ cells/ml and transferred into a 125 ml flask. The cells were incubated at 37° C. and 5% $CO_2$ under continuous shaking (100 rpm) and after 6 d the supernatant was harvested by centrifuging it 2 times (4000 rpm, 5 min). The supernatant was filtered through 0.2 μm filter and antibody titer was determined (see below).

The antibody-titer determination was conducted via two different HPLC methods, Reverse-phase (RP) HPLC and Protein A-HPLC. The RP-HPLC analysis was conducted with an Agilent 1200 Series HPLC system. Data were analyzed with the software "Chem Station for LC Systems" Rev. B.04.02. The solvent components were: isopropanol (HPLC Grade; Roth), acetonitrile (HPLC Gradient Grade; Roth), $H_2O$ (0.2 µm filtered) and tetrafluoracetate (TFA) (for peptide synthesis; Sigma). Solvent A: $H_2O$, 0.1% TFA; Solvent B: 60% isopropanol, 30% acetonitrile, 9.9% $H_2O$, and 0.1% TFA. A Phenomenex Jupiter column (#525166-6) with porosity of 300 Å and separation material with a particle diameter of 5 µm was used. Bound antibody was eluted with a linear gradient from 30% to 43% solvent B within 10 min. Detection occurred at $\lambda=210$ nm with a UV/VIS detector.

The Protein A-HPLC analysis was conducted with an Agilent 1200 Series HPLC system. Data were analyzed with the software "Chemstation" version Rev. B.04.02. The following solvents were used, solvent A: 0.05M Tris/HCl, 0.1M Glycine, 0.15M NaCl, pH 8.0; solvent B: 0.05M Tris/HCl, 0.1M Glycine, 0.15M NaCl, pH 3.0. For analysis, an Upchurch 2×20 mm analytical guard column was packed with 120 µl of Applied Biosystems Poros® 20A perfusion chromatography media (Life technologies). Bound antibody was eluted with 100% solvent B. In case purified antibody was collected, fractions were neutralized with 56 mM Tris pH 8.0.

The expressed antibodies were purified with a 1 ml HiTrap™ rProtein A FF column (GE Healthcare) via fast protein liquid chromatography (Äkta Explorer). The running buffer contained 10 mM Tris-HCl pH 8.0, 150 mM NaCl, the elution buffer was composed of 100 mM glycine, 150 mM NaCl, pH 2.7. Eluted antibodies were neutralized with 60 mM Tris-HCl pH 8.0, concentrated, sterile filtered and stored at −80° C.

Example 2. Antibody Screening and Characterization of 8A6

Screening of hybridoma supernatants is performed using techniques as known in the state of the art, e.g. ELISA-binding assay, Biacore assay or FACS-binding analysis. To test antigen specific binding of chimeric 8A6 or the humanized variants, ELISA plates (Nunc-Immuno Plate, F96 Maxisorp) were coated with 1 µg/ml sFcγRIIB, sFcγRIIA (SEQ ID NO. 12) or sFcγRIIAmut (SEQ ID NO. 13) in PBS (100 µl/well) overnight at 4° C. After 3 washing steps in 0.01% Tween in PBS, blocking with 2% BSA in PBS (300 µl/well) was conducted for 2 hours at room temperature. After 3 washing steps, serial dilutions of the purified antibody or supernatant were applied (100 µl/well) and incubated for 1 hour at room temperature. Purified antibodies were diluted in PBS, 2% BSA. Supernatants were supplemented with 10 times PBS and 20% BSA to obtain a final concentration of 2% BSA in PBS. As positive control for FcγRIIA the goat-anti-human FcγRIIA (R&D Systems, AF1875) was used. After 3 washing steps in 0.01% Tween in PBS, the respective secondary antibody donkey-anti-goat-HRP (F(ab')$_2$, Jackson-Immuno-Research) or goat-anti-human-HRP (F(ab')$_2$, Dianova) was incubated for 1 hour at room temperature (100 µl/well). Wells were washed 6 times in 0.01% Tween in PBS. Substrate (OPD containing 0.03% $H_2O_2$) was added (100 µl/well) and the reaction was stopped with 4 M $H_2SO_4$ (50 µl/well). Afterwards the absorbance was measured in a spectrometer at 492 nm.

Analysis of the specific binding to the native antigen of the chimeric 8A6 or humanized variants were conducted via cell binding on Raji (ATCC® CCL-86™) and K-562 cells (ATCC® CCL-243™).

Cells were pelletized by centrifugation (400 g, 5 min) and washed in FACS-buffer (Hanks balanced salt solution, 1% FCS, 0.01% NaN$_3$). After an additional centrifugation step, cells were resuspended in FACS-buffer to obtain a final cell concentration of 2×10$^6$ cells/ml and 50 µl of the cell suspension was aliquoted in a 96-well U-bottom plate. Serial dilutions of the humanized variants and ch8A6 were prepared in FACS-buffer.

To verify the expression of FcγRIIA on K-562 cells the mouse-anti-human CD32 antibody (Stem Cell Technologies Inc., Clone VI.3) was diluted in FACS-buffer. 50 µl of the diluted antibodies was added to the cells and incubated for 30 min at 4° C. Cells were washed 2 times in FACS-buffer. Afterwards, 50 µl goat-anti-human IgG-PE conjugated (F(ab')$_2$, Dianova) or goat-anti-mouse IgG-PE conjugated (F(ab')$_2$, Dianova) secondary antibody was diluted in FACS-buffer, added to the cells and incubated for 30 min at 4° C. After 2 washing steps in FACS-buffer, cells were resuspended in 300 µl FACS-buffer and measured in BD FACSCanto™ II (Software: BD FACSDiva™).

To determine whether FcγRIIB antibodies still allow binding of IgG or immune complexes to membrane-bound FcγRIIB a FACS based assay was conducted. Cells were pelletized by centrifugation (400 g, 5 min) and washed in FACS-buffer (Hanks balanced salt solution, 1% FCS, 0.01% NaN$_3$). After an additional centrifugation step, cells were resuspended in FACS-buffer to obtain a final cell concentration of 2×10$^6$ cells/ml. Serial dilutions of the antibodies (ch8A6_N297A, chGB3_N297A, R&D Ab mab1875) were prepared in FACS-buffer. 25 µl of the diluted antibodies were mixed in a 96-well U-bottom plate with 25 µl Alexa488-labeled aggregated Beriglobin (2.5 µl/well). Aggregated human IgG was isolated by size-exclusion chromatography on a Superdex-200 (16/60) from a commercially available pooled IgG product (Beriglobin).

50 µl of the cell suspension was added to the antibody-Beriglobin mixture and incubated for 1 hour at 4° C. Cells were washed 2 times in FACS-buffer. Afterwards, 50 µl goat-anti-human IgG-PE conjugated (F(ab')$_2$, Dianova) or anti-rat-PE secondary antibody was diluted in FACS-buffer, added to the cells and incubated for 30 min at 4° C. After 2 washing steps in FACS-buffer, cells were resuspended in 300 µl FACS-buffer and measured in BD FACSCanto™ II (Software: BD FACSDiva™) (FIG. 3).

FACS Binding Assay

Analysis of the specific binding to the native antigen of the chimeric 8A6 or humanized variants were conducted via cell binding on Raji and K-562 cells.

Cells were pelletized by centrifugation (400 g, 5 min) and washed in FACS-buffer (Hanks balanced salt solution, 1% FCS, 0.01% NaN3). After an additional centrifugation step, cells were resuspended in FACS-buffer to obtain a final cell concentration of 2×106 cells/ml and 50 µl of the cell suspension was aliquoted in a 96-well U-bottom plate. Serial dilutions of the humanized variants and ch8A6 were prepared in FACS-buffer.

Figure 4:
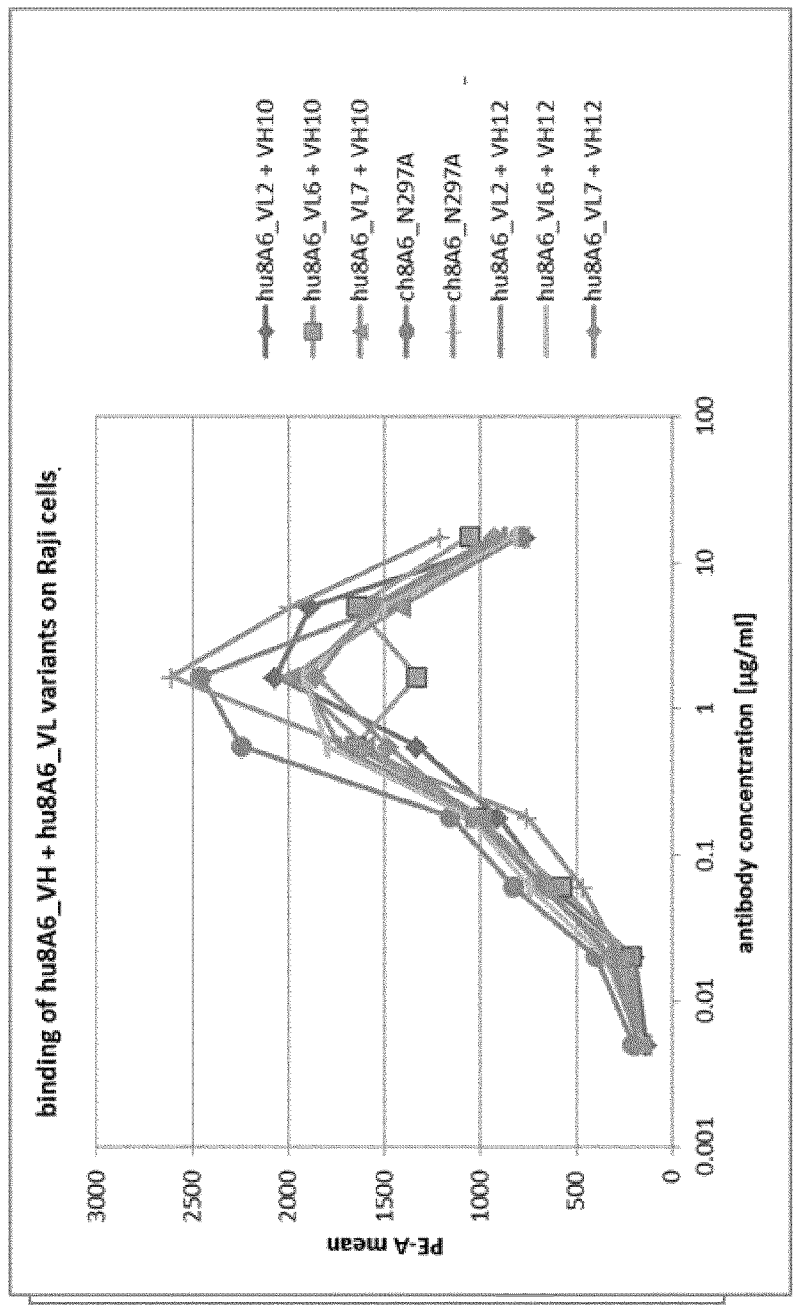
FIG. 4: Binding from 15 μg/ml to 0.005 μg/ml of Protein A purified antibody (hu8A6_VL+hu8A6_VH and ch8A6_N297A) to native FcγRIIB expressed on Raji cells. Humanized 8A6 variants bind with high avidity to FcγRIIB expressed on Raji cells.
Figure 5:
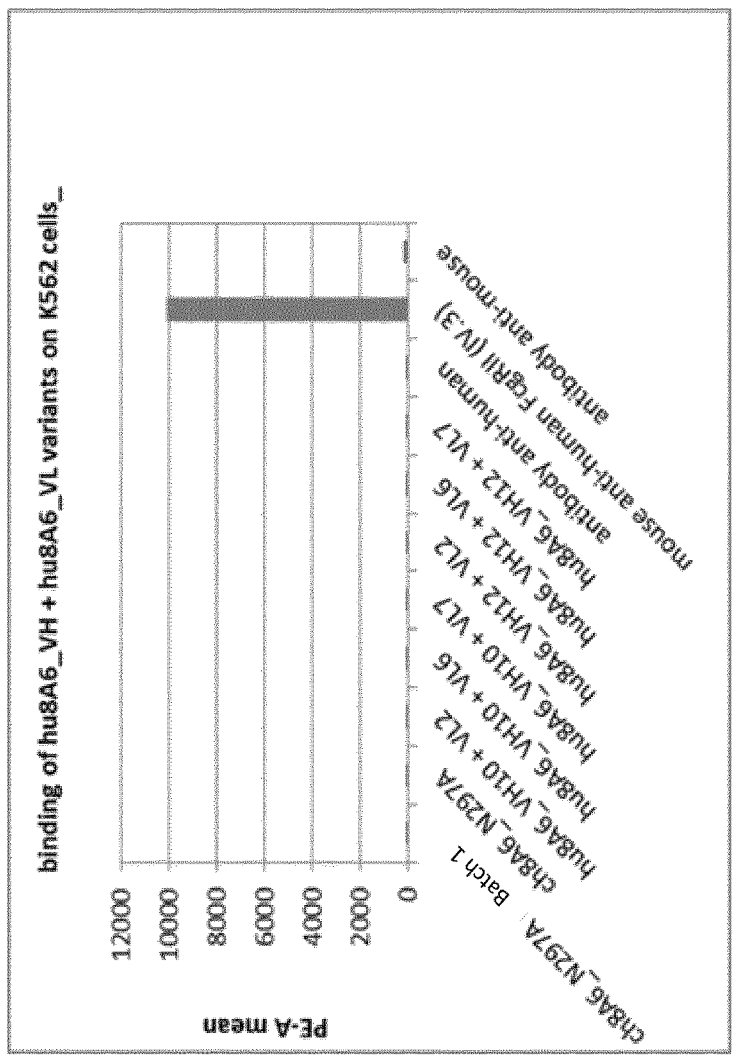
FIG. 5: Binding of 15 μg/ml antibody (hu8A6_VH+hu8A6_VL and ch8A6_N297A) to native FcγRIIA expressed on K562 cells. The antibodies do not bind to FcγRIIA on K-562.

Raji and K562 cells were incubated with increasing concentrations of humanized antibodies and the chimeric antibody as control. Raji cells were used to test binding on FcγRIIB (FIG. 4), K562 cells to analyze unspecific binding to FcγRIIA (FIG. 5). Cell bound antibodies were detected with PE-conjugated secondary antibody. All humanized variants bind to FcγRIIB with a comparable affinity as ch8A6_N297A and all humanized variants still bind FcγRIIB with greater avidity than FcγRIIA.

Antibody binding to sFcγRIIB and sFcγRIIA was analysed by surface plasmon resonance using a Biacore T200 biosensor (GE Healthcare/Biacore). Experiments were conducted at LMU, Department of Biology and Microbiology, Service Unit Bioanalytic. Analysed antibodies were captured on a Series S Sensor Chip CM5 sensor chip using the Human Antibody Capture Kit according to the manufacturer's protocol. Hu8A6 variants or ch8A6 were captured at a concentration of 10 nM for 1 min. The analyte sFcγRIIB was injected in various concentrations for 3 min. Measurements were performed at 25° C. and continuous flow (10 μl/min). Data was evaluated using the Biacore T200 Evaluation Software (version 1.0) assuming 1:1 binding.

Example 3. Chimerization of 8A6 Rat Antibody

The anti-FcγRIIB chimeric monoclonal antibody 8A6 was constructed by fusing the rat 8A6 VH region to a signal peptide and a human IgG1 constant region. Additionally a deglycosylated variant of the heavy chain was generated using an IgG1 constant domain containing a N297A mutation. To construct the 8A6 light chain gene, the rat 8A6 VL region was likewise fused to a signal sequence and the sequence for a human kappa constant region followed by sub-cloning into a mammalian expression vector.

In Vitro Assays
Cells, Reagents and Antibodies

The human Burkitt lymphoma cell lines Daudi and Ramos were purchased from DSMZ (ACC 78 and ACC 603) and maintained in RPMI 1640 (Gibco/Invitrogen) supplemented with 10% FBS (Gibco/Invitrogen), MEM NEAA (Gibco/Invitrogen), 1 mM sodium pyruvate (Gibco/Invitrogen) and 2 mM L-Glutamine (Gibco/Invitrogen) at 37° C. and 5% $CO_2$. Primary human B cells were purified from heparinized blood of healthy donors using Ficoll density gradients (Leucosep, Greiner Bio-One, Biocoll Separating Solution, Biochrom) and negative magnetic isolation (Dynabeads Untouched Human B Cells, Invitrogen). Purity of the enriched B cells was studied by FACS analysis by staining with anti-hCD19-APC (BD Pharmingen #555415), anti-hCD3-PerCP-Cγ5.5 (BD Biosciences #332771) and anti-hCD56-PE (BD Pharmingen #555515). Primary B cells were directly used for the experiments without further culturing. Blocking anti-FcγRIIB antibody 2B6 according to EP1534335.

Stimulation Protocol Using Soluble Antibody Stimulation Mix

For simultaneous stimulation of BCR and FcγRIIB an antibody system was set up using an antibody mix of 2 μg/ml monoclonal mouse anti-hIgM (Southern Biotech #9022-01, clone UHB) and 20 μg/ml monoclonal rabbit anti-mIgG(1,2a,3) (Epitomics #3020-1, clone M111-2) of which the Fc part cross-reacts with the human FcγRIIB receptor. Controls were conducted with 20 μg/ml polyclonal rabbit anti-hIgM (antibodies online # ABIN117299) or a mix containing 2 μg/ml anti-hIgM and isotype control mIgG2b (clone MPC-11, BD Pharmingen #557351). $3 \times 10^5$ cells of the lymphoma cell lines Daudi or Ramos and primary B cells were harvested by centrifugation and incubated with the different stimulation mixes in Assay medium (RPMI 1640+1% FBS) for 20 min at 37° C.

Subsequently 5 μg/ml anti-FcγRIIB antibodies ch8A6 (0.8 μl of a 1:10 dilution), 2B6 (1.5 μl of a 1:10 dilution) or chGB3_N297A (1.1 μl of a 1:10 dilution) were added to the samples and cells were further incubated for 25-30 min. Lysis was performed as described separately.

Western Blot Analysis of Phosphorylation Patterns
Cell Lysis

Cells were pelleted at 4° C., washed with ice-cold PBS and incubated in 10 μL lysis buffer (RIPA buffer (Cell Signaling) supplemented with phosphatase inhibitors (PhosStop, Roche), protease inhibitors (Complete Ultra Mini, EDTA-free, Roche) and 1 mM PMSF (Fluka Biochemica) for 30-45 min on ice.

SDS-PAGE

After centrifugation, supernatants were loaded with sample buffer (NuPAGE LDS Sample Buffer, NuPAGE Sample Reducing Agent, Invitrogen) applied to SDS PAGE (NuPAGE Novex Bis-Tris Mini Gels, MES SDS Running Buffer (Invitrogen)). For SDS-PAGE, LDS sample buffer and Reducing Agent were added and samples were heated at 95° C. for 5 min. Samples were stored at -20° C. or directly analyzed by SDS-PAGE and Western Blot.

Protein Transfer to PVDF Membranes and Detection

Subsequently, proteins were transferred to PVDF membranes (Roti-PVDF, Roth, Transfer buffer 10 mM Tris, 100 mM Glycin, 10% Methanol, transfer conditions 240 mA const., 90 min at 4° C.). Membranes were blocked with 5% BSA in TBS-T (10 mM Tris, 150 mM NaCl, 0.1% Tween20) and stained with anti-FcγRIIB/CD32 Phospho (pY292) (Cell Epitomics #2308-1, 1:50000, 4° C. overnight) or anti-phosphoSHIP (1:1000, Cell Signaling #3941) and anti-rabbit-HRP (Jackson ImmunoResearch #111-036-045, 1:50,000 in TBS-T, 1 h RT). Chemiluminescence (developed with WesternLightning Plus, Perkin Elmer) was detected on X-ray films.

Stripping

For subsequent analyses with antibodies directed against other phosphorylated-proteins, membranes were stripped (Re-Blot Plus, Millipore) for 10 min, washed and blocked before staining with anti-R-Actin antibody (Sigma-Aldrich # A1978, 1:50,000 and anti-mouse IgG-HRP, Sigma-Aldrich # A9044) or antibodies for other signalling proteins.

FcγRIIB-ITIM Phosphorylation in PBMC from Healthy Donor Markedly Increased by the Disclosed Antibodies PBMC from a healthy donor were isolated and either left untreated or incubated for 25 minutes with the stimulation mix (monoclonal mouse anti-hIgM and monoclonal rabbit anti-mIgG). Subsequently, cells were treated either with ch8A6 or buffer as control. Cell lysates were subjected to Western Blot analysis using appropriate detection antibodies as outlined above. A markedly increase in the phosphorylation of the FcγRIIB-ITIM motif of cells (PBMC, B cells) was detected (FIG. 6a). Control experiments with stimulation of cells with stimulation mix alone, or only monoclonal mouse anti-hIgM, monoclonal rabbit anti-mIgG in combination with ch8A6 did not show an increased FcγRIIB-ITIM-phosphorylation (FIG. 6b). The disclosed antibodies thus show a markedly effect on the ITIM-phosphorylation of human cells with crosslinked BCR (B cell receptor) and membrane-bound (endogenously expressed) FcγRIIB and not on unstimulated cells, i.e. cells without crosslinked BCR and membrane-bound FcγRIIB. During an auto-immune disease, BCR and membrane-bound FcγRIIB will be crosslinked by auto-antigens or immune complexes (ICs). The antibodies are able to inhibit pathogenic autoreactive B cells in an auto-immune disease by increasing FcγRIIB-ITIM-phosphorylation. However, the antibodies are also able to increase ITIM-phosphorylation without crosslinked BCR (FIG. 6c).

Comparison of the Effects of ch8A6 with Antibody chGB3_N297A

Comparison of the effect of clone ch8A6_N297A and clone chGB3_N297A on ITIM phosphorylation. Human Daudi cells were treated with an antibody mix and, subsequently, ch8A6_N297A, chGB3_N297A or 2B6 as described above. The antibody chGB3_N297A, like ch8A6_N297A, is a non-blocking anti-FcγRIIB antibody and recognizes a similar epitope. Addition of ch8A6_N297A to the antibody-mix treated cells showed an increase of FcγRIIB-ITIM phosphorylation already at concentrations of 0.05 μg/ml. Though increasing concentrations of the chGB3_N297A showed a dose-dependent stimulation of phosphorylation of the inhibitory motif, surprisingly this antibody clone was not able to reach phosphorylation levels comparable to 8A6. Densitometric quantitation of the X-ray film with the software "ImageJ" calculated values of a maximum of 2.8-fold phospho-signals, whereas hu8A6_N297A lead to a 9.8-fold increase compared to untreated cells (FIG. 7). Thus the inventive antibodies clearly and surprisingly show an increased FcγRIIB-ITIM-phosphorylation in comparison to the antibody chGB3_N297A.

Figure 8:
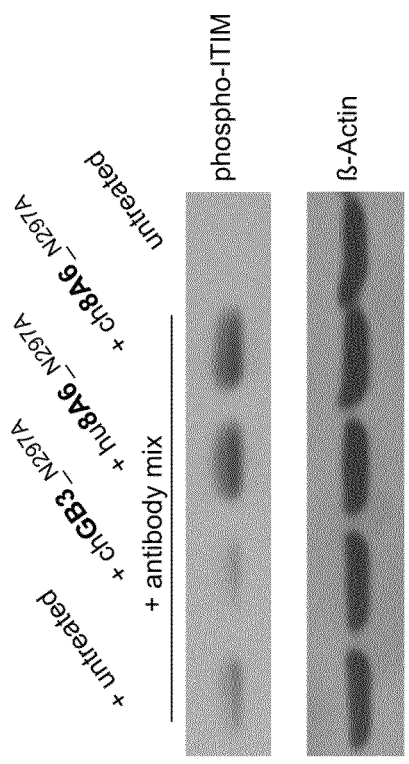
FIG. 8: Comparison of the effect of the humanized variant hu8A6_N297A and ch8A6_N297A and chGB3_N297A on ITIM phosphorylation in primary PBMCs. After crosslinking of BCR and FcγRIIB by the antibody mix, the different antibodies were added at 5 μg/ml and Western Blot analysis for ITIM phosphorylation was conducted. β-Actin=loading control.

Comparison of the Effect of the Humanized Variant hu8A6, Chimeric 8A6_N297A and chGB3_N297A on ITIM Phosphorylation in Primary PBMC Antibody chGB3_N297A, ch8A6_N297A and humanized 8A6 were compared in their influence on FcγRIIB-ITIM phosphorylation of primary human PBMC. After crosslinking of BCR and FcγRIIB by the antibody mix, the different antibodies were added at 5 μg/ml and Western Blot analysis for ITIM phosphorylation was conducted. Again the antibodies surprisingly have a markedly increased effect on FcγRIIB-ITIM-phosphorylation compared to the antibody in the state of the art (FIG. 8).

Co-Immunoprecipitation of the Phosphorylated FcγRIIB-ITIM Motif and SHIP-1

Subsequent to the crosslinking of receptors, the phosphatase SHIP is recruited to the membrane via binding of its SH2 domain to the phospho-tyrosine in the FcγRIIB-ITIM motif, followed by tyrosine phosphorylation at the NPXY motif in the C-terminal domain of SHIP-1. The relocalization in the membrane and subsequent phosphorylation of the NPXY motif is essential for the regulatory function of SHIP-1. Its effect on calcium flux, cell survival, growth, cell cycle arrest and apoptosis is mediated through the PI3K and Akt pathways. Tyr1021 is located in one of the NPXY motifs in SHIP-1, and its phosphorylation is important for SHIP-1 function (Nimmerjahn, Ravetch, 2008).

Human Daudi cells were stimulated with the antibody mix as defined in section [00103] above and after lysis in a mild lysis buffer (CoIP lysis buffer), the samples were incubated with 2B6 for capturing FcγRIIB. Complexes were bound to ProteinG-coupled ferromagnetic beads and isolated with a magnetic rack.

Lysates of 1×10$^7$ cells/sample were prepared in 500 μl CoIP lysis buffer, incubating the cells for 30 min on ice and vortexing every 10 min. Cell debris was spun down at 13,000 rpm for 10 min at 4° C. and the supernatants were transferred to new tubes. 500 μl of the lysates were incubated with 10 μg 2B6 for 2-3 h at 4° C. end-over-end. Magnetic Protein G-coupled beads were washed twice with 500 μl lysis buffer and 50 μl beads (1.5 mg) were added to the lysate-antibody-complexes overnight at 4° C. (rotating wheel). Complexes were eluted from the beads by washing twice with 200 μl lysis buffer and heating the beads for 5 min in 25 μl 1×LDS sample buffer containing reducing agent.

After centrifugation at 4000×g for 30 sec, 10 μl of the supernatant were applied to SDS-PAGE for Western Blot analysis.

Western Blot analyses of the lysates show significantly elevated levels of phospho-SHIP-1 in the samples of cells treated with antibody mix and ch8A6_N297A. As the precipitation was performed with the FcγRIIB-specific antibody 2B6, only isolated SHIP-1 was co-precipitated that had bound to FcγRIIB. Membranes after stripping and restaining showed enhanced phosphorylation of the FcγRIIB-ITIM motif in samples treated with ch8A6_N297A, correlating with the phospho-SHIP1 signals. A second restaining with α-hFcγRIIB a, b, c (human FcγRII/CD32 Ab, polyclonal, goat IgG, R&D Systems, AF1330) showed equal amounts of the precipitated receptor FcγRIIB in all samples, serving as a loading control for SDS-PAGE (FIG. 9).

Example 4. Humanization of ch8A6 in IgG Format ch8A6 was humanized by grafting the complementarity-determining region sequences from the rat antibody onto human frameworks. To select human frameworks the $V_H$ and $V_L$ sequences were compared with those of human Ig variable and joining region germline segments, obtained from publicly available databases (IMGT; V-BASE). VH_3_30 plus IGHJ4 human germline sequences and the VK3_15 plus IGKJ2 human germ-line sequences were chosen for the heavy and light chains, respectively.

Several variants for humanized heavy and light chains were generated. The genes coding for the designed sequences of the humanized $V_H$ and $V_L$ followed by subcloning into a mammalian expression vector. The screening procedure of the antibody variants were performed directly from the supernatant of transfected CHO-S cells (Invitrogen). The chimeric 8A6 antibody served as a transfection control and standard during the screening of the humanized variants. Hu8A6 variants were analysed for binding on sFcγRIIB and sFcγRIIA via ELISA and on native FcγRIIB via FACS on Raji cells (see above). Additionally a kinetic characterization of the antibody variants was performed with surface plasmon resonance.

Test of Humanized 8A6 Variants

To test the phosphorylation activities of 8A6 humanization variants, Daudi cells were stimulated with the antibody mix, treated with 0.5 or 5 μg/ml of the different 8A6 variants, and Western Blot analysis for ITIM phosphorylation was conducted.

Comparison of Humanized 8A6 Variants to ch8A6_N297A

All tested humanized variants of 8A6 were able to induce phosphorylation of the receptor and phosphorylation levels were comparable to that induced by ch8A6_N297A from the same purification batch. Thus, no loss of activity was detected after the second humanization round. Although Biacore data suggested different affinities for the different combinations of heavy and light chain, those differences were not detectable by Western Blot analyses (FIG. 10).

Comparison of Humanized 8A6 Variants to ch8A6_N297A, Blocking Anti-FcγRIIB (2B6) and chGB3_N297A After the final humanized chain combination was chosen, the variant, combining heavy chain $V_H10$ with light chain $V_L6$, was compared to the antibodies ch8A6_N297A, 2B6 and chGB3_N297A (FIG. 11).

In Vivo Assays
SLE-PBL-Model

Rag2/gamma-dFcγ−/− mice were irradiated at a dosage of 6 Gy and injected intraperitoneally with varying amounts of human peripheral blood leucocytes in 500 µl PBS.

Figure 12:
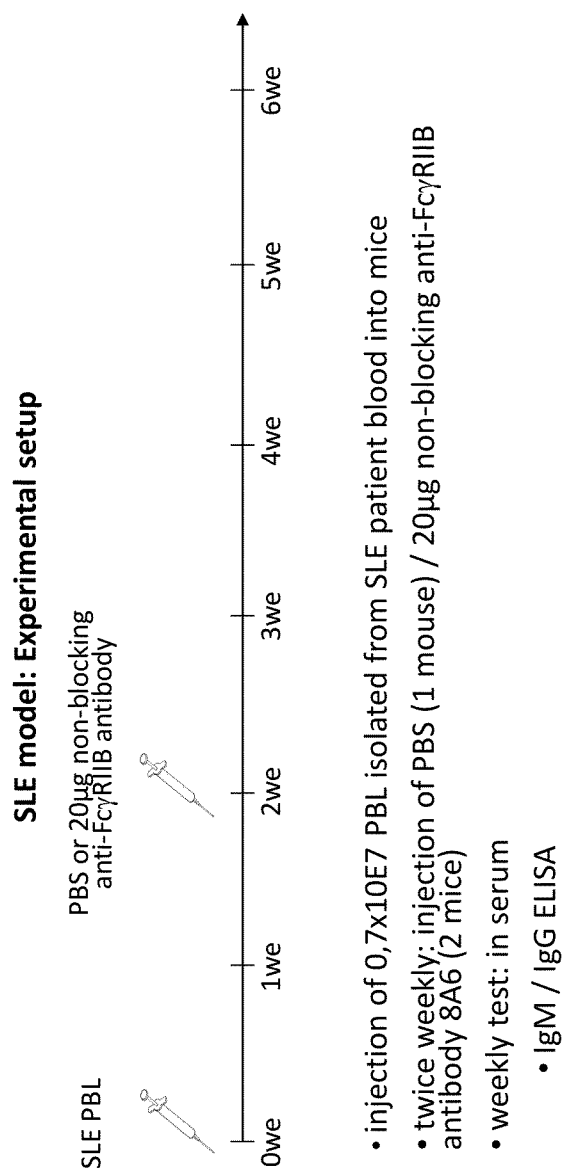
FIG. 12: Experimental setup for SLE-PBL mouse model. PBL from human SLE patients are transferred into immuno-compromised mice. PBL cells are engrafted and mice are subsequently treated with control (PBS) or anti-FcγRIIB ch8A6_N297A antibody according to the invention.

Treatment of mice was started 2 weeks following injection of cells after grafting of human SLE-patient PBL in mice was verified by the presence of hIgM or hIgG. Mice were treated with 200 µl buffer (PBS) or 20 µg antibody (ch8A6_N297A) in 200 µl PBS intraperitoneally twice weekly for 4 weeks. Mice were weighed and bled to obtain serum once weekly. Serum samples were frozen at −80° C. until further use (FIG. 12).

ELISA

Serum samples were analyzed by ELISA for the presence of total human IgG, IgM and anti-DNA IgM and IgG.

For quantification of total serum IgM and IgG in serum samples, the Bethyl Human IgM ELISA Quantitation Kit and the Human IgG ELISA Quantitation Kit (Biomol) were used according to the manufacturer's instructions. OD was measured with VersaMax tuneable microplate reader (Molecular Devices) at 450 and 650 nm.

For the detection of anti-DNA antibodies, ELISA plates were coated with 10 µg/mL methylated BSA (Sigma) in PBS for 2 h at room temperature. After washing, the plates were coated with 50 µg/mL calf thymus DNA (Sigma) in PBS at 4° C. overnight. Blocking of unspecific binding was performed with PBS/0.1% gelatin/3% BSA/1 mM EDTA for 2 h at room temperature. Sera were diluted 1:100 in the blocking solution and incubated for 1 h at room temperature. As a detection antibody, the HRP-conjugated antibody of the human IgM Quantitation Kit (Bethyl) was used and diluted 1:10,000 in blocking solution followed by incubation for 1 h at room temperature. PBS was used for all washing steps. For detection, TMB Solution was added and the reaction was stopped with 6% orthophosphoric acid.

SLE PBL Model, Total Human Serum Immunoglobulin

Figure 13:
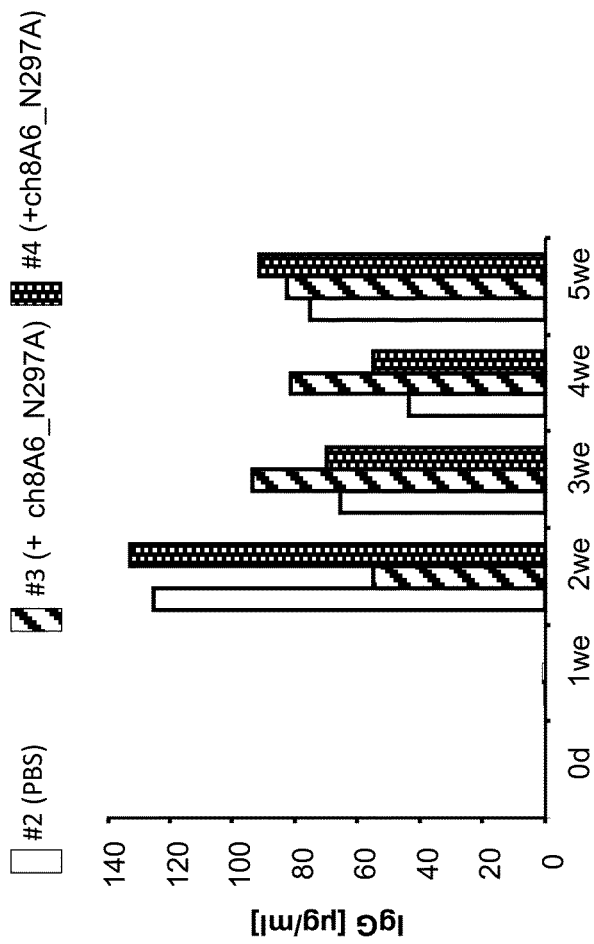
FIG. 13: Total human IgG level [μg/mL] in mice grafted with PBL from human donors suffering from SLE. Depicted are mice treated with control (#2, PBS) or ch8A6_N297A (#3 and #4).

Total human IgG levels [µg/mL] were analyzed in mice grafted with PBL from human donors suffering from SLE. No significant difference in total human IgG between PBS or anti-FcγRIIB was detected. The antibody according to the invention does not significantly influence total human IgG (FIG. 13).

SLE PBL Model, Influence on Anti-DNA Antibodies (Disease Specific IgG)

Figure 14:
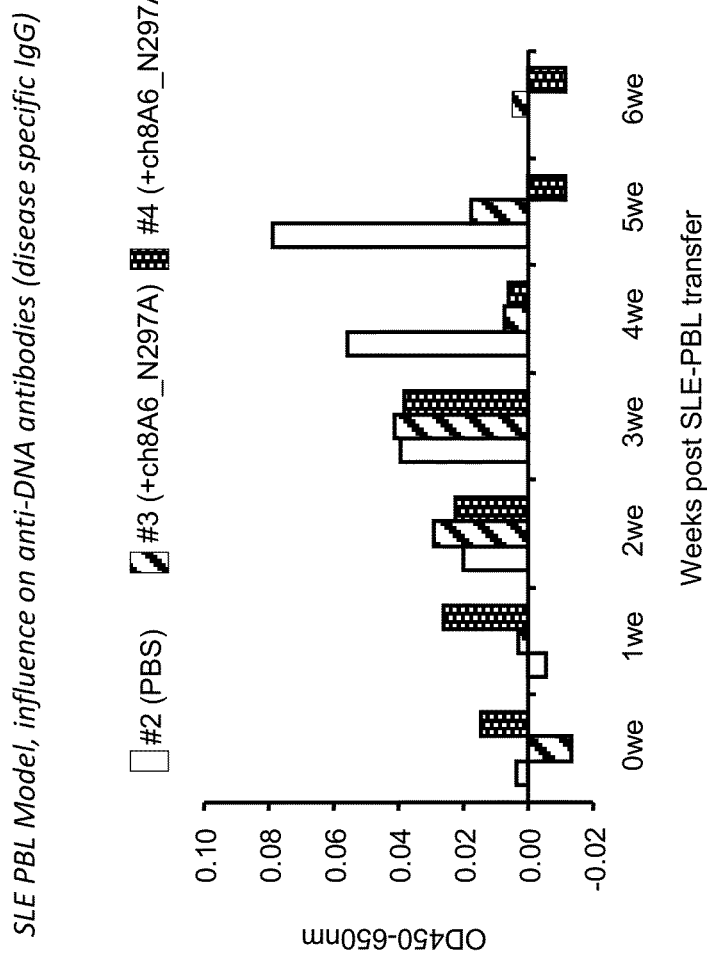
FIG. 14: Reduction in disease specific human anti-DNA IgG in ch8A6_N297A treated mice starting in week 4 post SLE-PBL transfer/grafting using PBL from human donors suffering from SLE. Depicted are anti-DNA IgG titers in two different mice, #3 and #4 (treated with ch8A6_N297A), #2 shows PBS control.

A markedly reduction in disease specific human anti-DNA IgG in anti-FcγRIIB mice starting in week 4 post SLE-PBL transfer/grafting was observed. The disclosed antibodies specifically reduce the amount of disease relevant anti-DNA antibodies (FIG. 14).

Example 5—Generation of Bispecific Antibody Binding to Fc Gamma IIb Receptor and Fc Epsilon Receptor Definition of the Nomenclature of 8A6-IgG and the 8A6-IgE Construct:

| chimeric: | |
|---|---|
| 8A6-IgG | ch8A6_N297A |
| 8A6_cε2-4 | ch8A6_cε2-4 |
| 8A6_cε2-4-deglycosylated | ch8A6_cε2-4-degly |
| 8A6_cε3-4 | ch8A6_cε3-4 |
| 8A6_cε3-4-deglycosylated | ch8A6_cε3-4-degly |
| 8A6_cε2-4 deglycosylated produced at Trenzyme | ch8A6_cε2-4-degly_T |
| 8A6_cε3-4-deglycosylated produced at Trenzyme | ch8A6_cε3-4-degly_T |
| humanized: | |
| 8A6_cε2-4 | hu8A6_cε2-4 |
| 8A6_cε2-4-deglycosylated | hu8A6_cε2-4- degly |
| 8A6_cε3-4 | hu8A6_cε3-4 |
| 8A6_cε3-4-deglycosylated | hu8A6_cε3-4-degly |

Description of the generation, expression and purification of different FcγRIIB IgE-antibodies.

Construct Design

Figure 15:
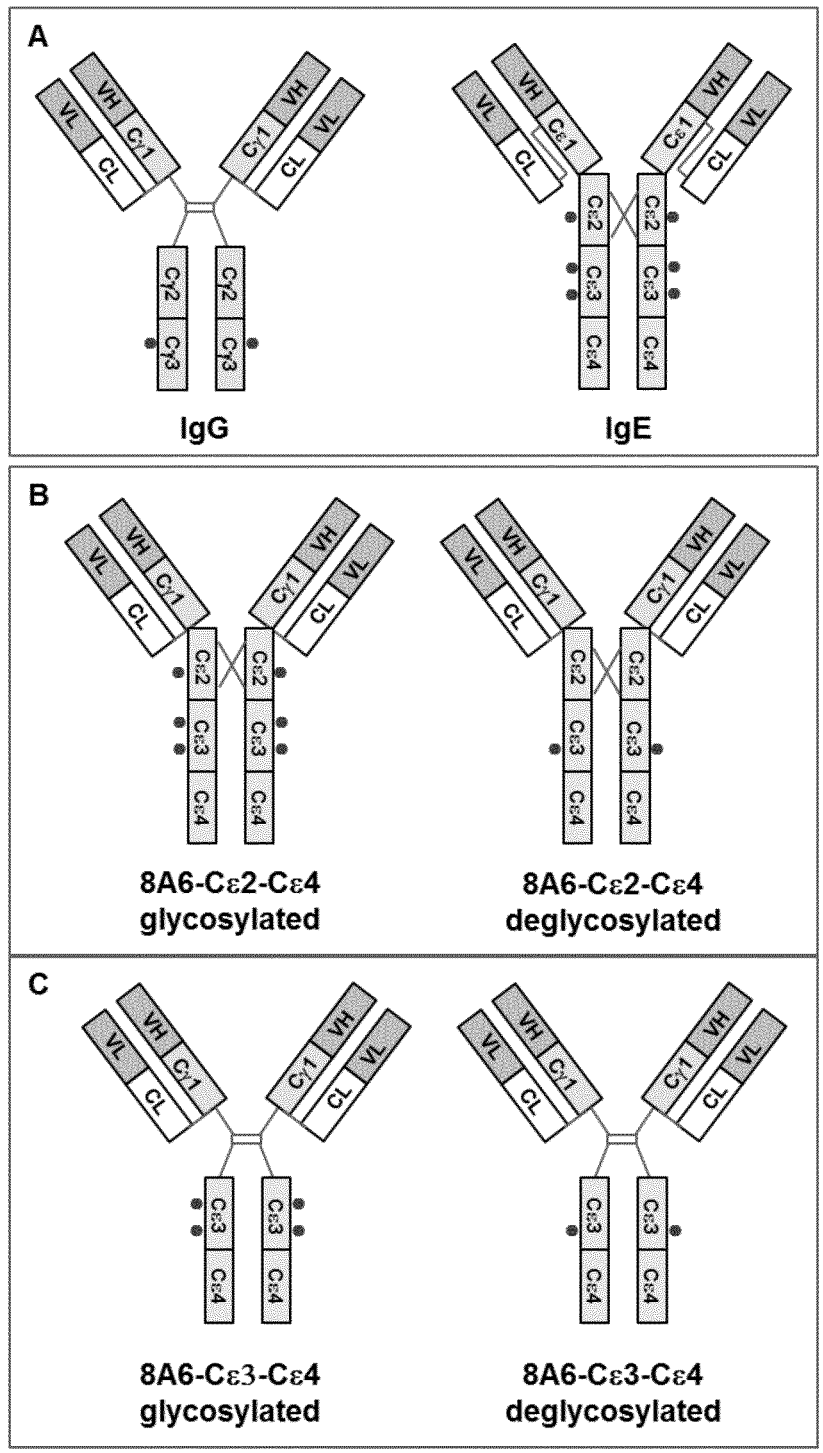
FIG. 15: Constructs composed of the Fab-domain of the chimeric FcγRIIB-specific IgG-antibody and the Fcε-domain of an IgE-antibody. The constructs differ with regard to the changeover from IgG-based Fab and the Fcε-domain (B. with Cε2 domain, C. without Cε2 but with IgG hinge region) and the quantity of N-glycosylation sites. For comparison a schematic of a complete IgG and a complete IgE molecule is shown (A).

As depicted in FIG. 15 all constructs have in common that the Fab-domain of the hybrid antibody is equivalent to an IgG molecule (variable domain and CL-/CH1-domain). Moreover all constructs have the IgE-constant domain Cε3 and Cε4. These domains are homologous with IgG-Cg2 and Cg3. In an IgG antibody the hinge-region is responsible for the required flexibility of the molecule and forming the dimer via disulfide bridges. This hinge-region does not exist in the IgE antibody. Instead of the hinge region, the extra domain Cε2 adopts this function. The 8A6-IgE antibody shows a high flexibility of the Fab-domain along with an optimal changeover from the Cg1-domain into the Cε-domain. Therefore variants either holding the hinge region of IgG (see FIG. 15) or the complete Fcε-domain (Cε2, Cε3, Cε4) of IgE (see FIG. 15) were designed. Another variation regards the different amount of N-glycosylation-sites in the Fcε-domain. The glycosylation of the IgE-Fc-domain has no influence on the affinity to FcεRI, but on expression and stability of the antibody. These constructs were cloned into plasmid vectors following standard laboratory procedures.

Cell Lines and Culture Conditions

CHO-S cells were cultured according to the supplier's recommendations. Briefly, cells were cultured in Freestyle CHO-S medium, supplemented with 2 mM Glutamax and passaged every 2-3 day. Cells were cultured at 37° C., 5% $CO_2$, 100 rpm. One day prior to transfection cells were split in density $0.5 \times 10^6$/ml and viability was checked (>96%). The human Burkitt lymphoma cell lines Raji and Daudi were cultured in RPMI 1640 supplemented with 10% FBS, MEM NEAA, 1 mM sodium pyruvate and 2 mM L-Glutamine at 37° C. and 5% $CO_2$. Cells were passaged every 2-3 days in a density of $0.2$-$1.0 \times 10^6$ cells/ml.

Transfection of CHO-S with FcγRIIB_IgE Constructs

On the day of transfection cell density was $1.0$-$2.0 \times 10^6$/ml. $8.0 \times 10^8$ cells were diluted in 20 ml CHO Freestyle Medium ($40 \times 10^6$/ml). 1000 µg Plasmid-DNA (500 µg of each, heavy and light chain) were added (50 µg DNA/ml transfection volume), followed by addition of 2000 µg PEI (00 µg PEI/ml transfection volume). Cells were incubated for 3 h at 37° C., 5% $CO_2$, 100 rpm. After this, the cell suspension was diluted 1:10 in CHO Freestyle medium, 0.5 mM valproic acid added, and incubated at 31° C., 5% $CO_2$, 100 rpm for 10 days. Supernatants were harvested by centrifugation 2×10 min at 4000×g.

Titer Determination, Purification and Size Exclusion Chromatography

Antibody Titer Determination Via Protein A-HPLC

The Protein A-HPLC analysis was conducted with an Agilent 1200 Series HPLC system. Data were analyzed with the software "Chemstation" version Rev. B.04.02. The following solvents were used, solvent A: 0.05M Tris/HCl, 0.1M Glycine, 0.15M NaCl, pH 8.0; solvent B: 0.05M Tris/HCl, 0.1M Glycine, 0.15M NaCl, pH 3.0. For analysis, an Upchurch 2×20 mm analytical guard column (# C-130B) was packed with 120 μl of Applied Biosystems Poros® 20A perfusion chromatography media (Life Technologies, #4374732). Bound antibody was eluted with 100% solvent B. In case purified antibody was collected, fractions were neutralized with 56 mM Tris pH 8.0.

Purification of 8A6-IgE

After six days of cultivation, cells were harvested and the antibody-containing supernatants gained by centrifugation, 2×10 min at 4000×g. Antibodies were purified with a 5 ml High trap Protein A FF column (GE Healthcare) via fast protein liquid chromatography (Äkta Explorer). Binding of the antibody to Protein A is mediated through its VH3 framework. The running buffer contained 10 mM Tris-HCl pH 8.0, 150 mM NaCl, the elution buffer was composed of 100 mM Glycine pH 2.7, 150 mM NaCl. Eluted antibodies were neutralized with 60 mM Tris-HCl, pH 8.0, concentrated (Sartorius Vivaspin4) to approx. 1.0 mg/ml, sterile filtered with a 0.2 μm filter and stored at −80° C.

Example 6: Characterization of Chimeric 8A6-IgE Constructs

Size Exclusion-HPLC

In order to determine the oligomeric state and homogeneity of purified 8A6-IgE variants, samples were applied to SE-HPLC. The SE-HPLC was conducted with an Agilent 1200 Series HPLC system. Data were analyzed with the software "Chemstation" version Rev. B.04.02. The analysis was carried out with a Superdex 200 10/300 GL column (GE Healthcare). The following solvent was used, 5 mM His, 150 mM NaC, pH 6.5. 25 μg of protein were applied in a concentration of 0.5 μg/μl.

This revealed that the glycosylated 8A6-IgE variants may have the tendency to form more dimers compared to standard ch8A6_N297A, while degylcosylated 8A6-IgE seemed to be more degraded and have a higher percentage of fragments compared to standard ch8A6_N297A.

Binding Assays

Several binding assays were performed to analyse the binding affinity and specificity of the antibodies. For these binding assays, soluble FcεRIα was generated according to the protocol below:

Generation of Soluble FcεRIα

Transfection of CHO-S with sFcεRIα

On the day of transfection cell density was ~$1.0 \times 10^6$/ml. 500 ml of the cell suspension was transferred to two 1 liter flasks. The Freestyle Max reagent was gently inverted and 312.5 μl diluted in 5 ml Optipro SFM (RT). 312.5 μg of plasmid DNA (pAC91, sFcεRIa-H6) (SEQ ID NO: 37) was diluted in 5 ml OptiPro SFM and gently mixed. The diluted FreestyleMax reagent was added to the DNA/Optipro SFM mixture and incubated for 15 min at RT. The DNA-lipid mixture was slowly added to the cells whilst slowly swirling the flask. Transfected cells were incubated at 37° C., 5% $CO_2$, 100 rpm for 6 days. Supernatants were harvested by centrifugation 2×10 min at 4000×g.

Purification of sFcεRIα

For the production of recombinant soluble FcεRIα, CHO-S cells were transfected with the His-tagged extracellular domain of human FcεRIα (pAC91), as described. Purification of sFcεRIα from cell supernatant was conducted via NiNTA-purification (Qiagen, #1018244) with an Äkta Explorer. The following buffers were used: binding buffer containing 50 mM NaH2PO4, 300 mM NaCl, 10 mM Imidazole, pH8.0; elution buffer containing 50 mM NaH2PO4, 300 mM NaCl, 400 mM Imidazole, pH 8.0.

Bound sFcεRIα was eluted with a linear gradient from 0% to 100% B. After concentration of sFcεRIα fractions, buffer exchange with 10 mM His, pH 6.5 was carried out. This was followed by purification of sFcεRIα with weak anion exchange chromatography with DEAE Sepharose FF (GE Healthcare, #17-0709-10) with an Äkta Explorer. Solvent A was composed of 10 mM His, pH 6.5; solvent B contained 10 mM His, 0.5 mM NaCl, pH 6.5. Bound sFcεRIα was eluted with a linear gradient from 2% to 100% B. Concentrated protein was stored in 10 mM His, 150 mM NaCl, pH6.5, −80° C.

SDS-PAGE

For SDS-PAGE analysis, 1 μg of purified antibody or Trenzyme material was applied to a NuPAGE Bis-Tris (4-12%) Gel. Antibodies were applied either in NuPAGE LDS sample buffer or under reducing conditions in addition of sample reducing reagent and pre-heating to 75° C. for 10 min, according to the manufacturer's recommendations. SDS-PAGE was performed with a constant power of 200V for 30 min. Afterwards gels were washed twice in $H_2O$ and stained with simply blue staining solution (Life Technologies). Removal of excessive dye occurred in $H_2O$ and visualization of gels was conducted with using a Transilluminator (UV, white light).

ELISA Binding Assay

Binding of 8A6-IgE to sFcγRIIB or sFcεRIα

Figure 16:
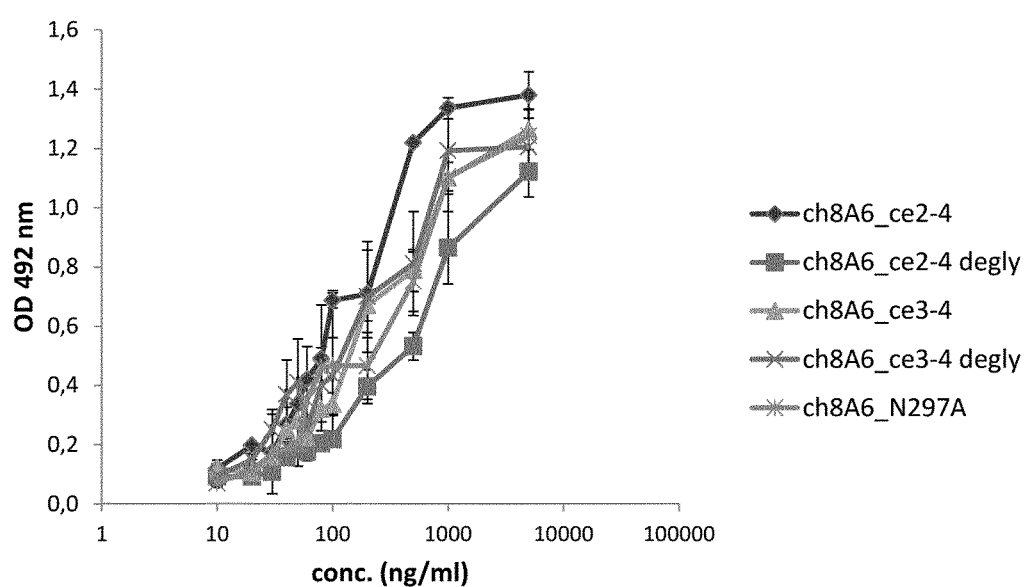
FIG. 16: Binding of 8A6-IgEs to SM101 (sFcγRIIB) tested by ELISA. The figure depicts a representative ELISA. The ch8A6-IgE variants have the same affinity to antigen SM101 (soluble FcγRIIB) as the chimeric anti-Fc gamma RIIB antibody.
Figure 17:
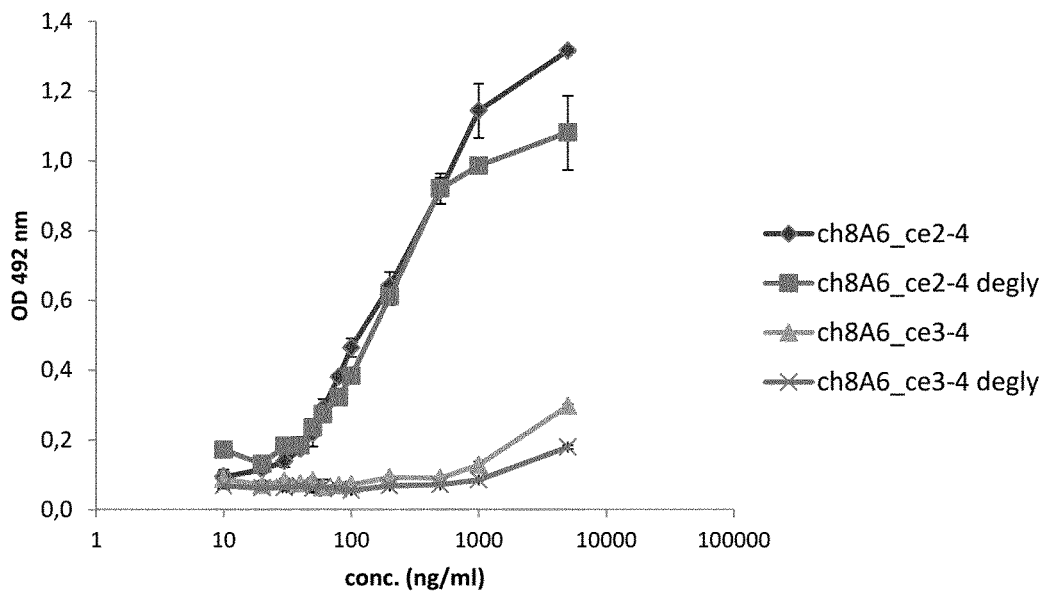
FIG. 17: Binding of 8A6_IgE variants to sFcεRIα determined by ELISA. The figure depicts a representative ELISA. The humanized anti-Fc gamma RIIB-IgE variants bind to sFcεRIα with the same affinity as the respective chimeric anti-Fc gamma RIIB-IgE version.

To test the binding efficacy of 8A6_cε2-4/8A6_cε3-4 antibodies in glycosylated and non-glycosylated format to both sFcγRIIB and sFcεRIα, an ELISA assay was established. For this, 96-well plates were coated with SM101 or sFcεRIα, 1 μg/ml in PBS (volume 100 μl), for 1 h at RT. Plates were 2× washed in PBS, 0.01% Tween®-20, and blocked in PBS, 2% BSA, 250 μl/well for 2 h, RT. After a wash step, the antibody samples were added in appropriate dilution series in PBS, 2% BSA to the coated wells for 1 h at RT. Plates were washed 3× in PBS, 0.01% Tween®-20 and secondary detection antibody directed to human kappa light chain-HRP conjugated was added 1:8000 in PBS, 2% BSA, for 1 h at RT. After three wash steps, bound HRP-conjugated antibody was detected with OPD, 0.03% $H_2O_2$ 100 μl/well. The reaction was stopped with 50 μl 4 M $H_2SO_4$ and absorption measured at 492 nm with an ELISA reader (Tecan, Spectra FluorPlus). Direct binding to sFcγRIIB revealed that all four 8A6_IgE constructs have the same affinity to sFcγRIIB as the ch8A6_N297A antibody (FIG. 16) due to the shared Fab domain. However, binding of the 8A6-IgE constructs to sFcεRIα demonstrated differences between the constructs with the full length IgE Fc part (cε2-4) and the shorter versions (cε3-4) (FIG. 17).

Binding of 8A6-IgE to sFcγRIIB and sFcεRIα—Sandwich ELISA

A sandwich ELISA was performed that displayed binding to both antigens at the same time. The binding efficacy of the generated 8A6_cε2-4/8A6_cε3-4 variants towards both targets sFcγRIIB as well as sFcεRIα was tested in this sandwich ELISA assay. For this, 96-well plates were coated with a soluble FcγRIIB (SM101), 1 μg/ml in PBS (volume 100 μl), for 1 h RT. Plates were washed 2× in PBS, 0.01% Tween®-20, and blocked in PBS, 2% BSA, 250 μl/well for 2 h, RT. After a wash step, the antibody samples were added in appropriate dilution series in PBS, 2% BSA to the coated wells for 1 h at RT. Plates were washed 3× in PBS, 0.01% Tween®-20 and incubated with sFcεRIα, 0.005 μg/ml in PBS, 2% BSA for 1 h at RT. Plates were washed 3× in PBS, 0.01% Tween®-20 and secondary biotinylated detection antibody directed to human FcεRIα CRA1 was added, 0.5 μg/ml diluted in PBS, 2% BSA for 1 h at RT. Plates were washed 3× in PBS, 0.01% Tween®-20 and HRP-conjugated streptavidin was added 1:200 in PBS for 20 min at RT. After three wash steps, bound HRP-conjugated Streptavidin was detected with OPD, 0.03% $H_2O_2$ 100 µl/well. The reaction was stopped with 50 µl 4 M $H_2SO_4$ and absorption measured at 492 nm with an ELISA reader.

The sandwich ELISA confirmed the results from the ELISA. Again, the low affinity of the 8A6_cɛ3-4 constructs to FcɛRIα was shown with simultaneous binding to FcγRIIB with the antibody's Fab fragment.

FACS Binding Analysis

Binding of antibodies to cell surface expressed native FcγRIIB was determined by FACS analysis. Raji cells were used, as this B-lymphocyte cell line deriving from Burkitt lymphoma expresses high levels of FcγRIIB. Raji cells were pelleted and $1.0 \times 10^5$ cells/well seeded in 96 well round bottom cell culture plates in 50 µl FACS-Buffer (HBSS, 5% FBS, 0.01% $NaN_3$). The antibodies to be tested were applied to the Raji cells in an appropriate dilution series in 50 µl of FACS buffer and incubated for 1 h at 4° C. After two wash steps with 200 µl FACS buffer, cells were incubated with FITC-conjugated secondary antibody directed to human kappa light chain $(Fab)_2$, diluted 1:200 in FACS buffer for 30 min at 4° C. After two wash steps, cell pellets were resuspended in 150 µl FACS buffer and analyzed by flow cytometry with a FACS Canto II (BD Biosciences).

Figure 18:
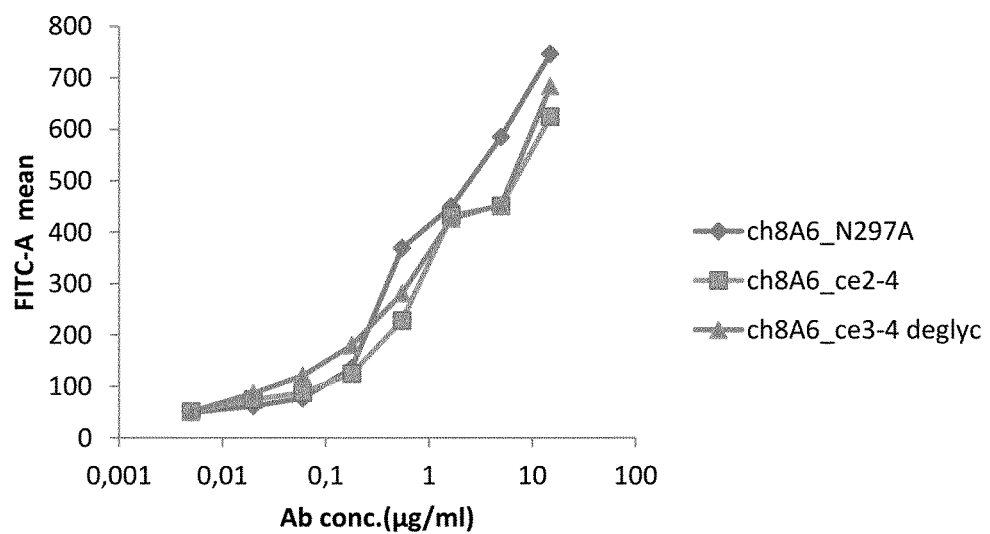
FIG. 18: Cell binding of anti-FcγRIIB-IgE antibody to FcγRIIB expressed on Raji. The figure depicts a representative FACS experiment, carried out with variants 8A6_cε2-4degly and 8A6_cε3-4degly, compared to ch8A6_N297A. Both 8A6-IgE variants as well as ch8A6_N297A have the same affinity to the native antigen FcγRIIB.

The assay showed for all 8A6 variants that the binding capacity of the Fab fragments to FcγRIIB remains compared to ch8A6_N297A, irrespective of changes introduced in the Fc part of the antibody (FIG. 18).

Biacore

Affinity of antibody constructs towards FcγRIIB and FcɛRIα was further analyzed by surface plasmon resonance (SPR) using the Biacore™ T200 system.

sFcγRIIB was covalently immobilized to a Series S Sensor Chip CM5 (Biacore, BR-1005-30) using the standard amine-coupling protocol (BIAsensor surface Handbook, Biacore). Antibody variants were captured at a concentration of 50 nM for 1 min. The analyte sFcɛRIα was injected in various concentrations 0.1-25 nM for 3 min, followed by a dissociation step for 7 min. The CM5 chip was regenerated with a buffer containing 3M $MgCl_2$ by dissolving the interaction of the ligand and SM101, thus preparing it for a new analysis cycle. Measurements were conducted at 25° C. and continuous flow (10 µl/min). Data evaluation was conducted using the Biacore T200 Evaluation Software (version 1.0), assuming 1:1 binding.

Summary of the Binding Experiments:

It was found that the binding affinity of all constructs to FcγRIIB was equal to that of the original IgG antibody. With respect to binding to FcɛRIα, the results of the binding characterization to both antigens of 8A6-IgE suggest that the shortened variants 8A6_cɛ3-4/degly may not exert the same high affinity to FcɛRI as the full length IgE constructs.

Example 7: Production and Characterisation of Humanized 8A6-IgE Antibodies

Humanization of 8A6-IgE

For humanization of ch8A6-IgE, the variable heavy chain of the antibody was exchanged with the humanized variable heavy chain 10 (VH10) of SEQ ID NO. 3. The variable light chain 6 (VL6; SEQ NO.4) was used together with the humanized heavy chains for expression of the humanized 8A6-IgE constructs.

Exchange of the variable heavy chain was conducted via standard cloning procedure. Exchange of the variable heavy chain occurred via standard cloning procedure. Correct insertion of inserts was verified by DNA sequencing.

Moreover, the C-terminal lysine of the heavy chain sequence was removed and exchanged into a Stop-codon (AAA→TAA). This significantly reduces the amount of charge variants. It was accomplished by mutagenesis PCR and successful mutation was verified by sequencing.

Characterisation of Antigen Binding of Humanized 8A6-IgEs by ELISA

Figure 19:
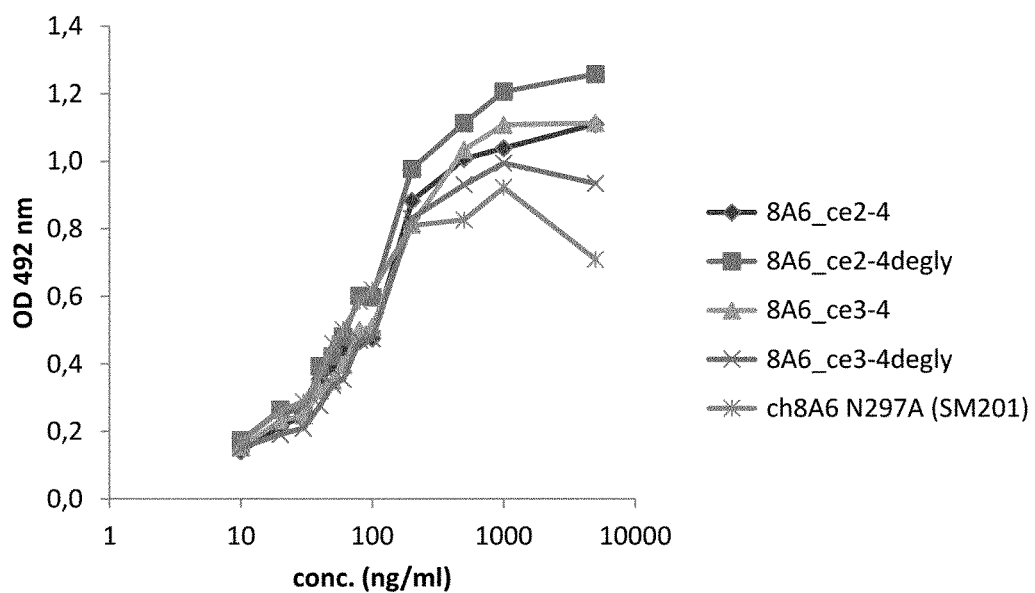
FIG. 19: Binding of 8A6-IgE to SM101, tested by ELISA. The figure depicts a representative ELISA. The humanized 8A6-IgE variants have the same affinity to antigen SM101 (soluble FcγRIIB) as the chimeric anti-Fc gamma IIB receptor antibody.
Figure 20:
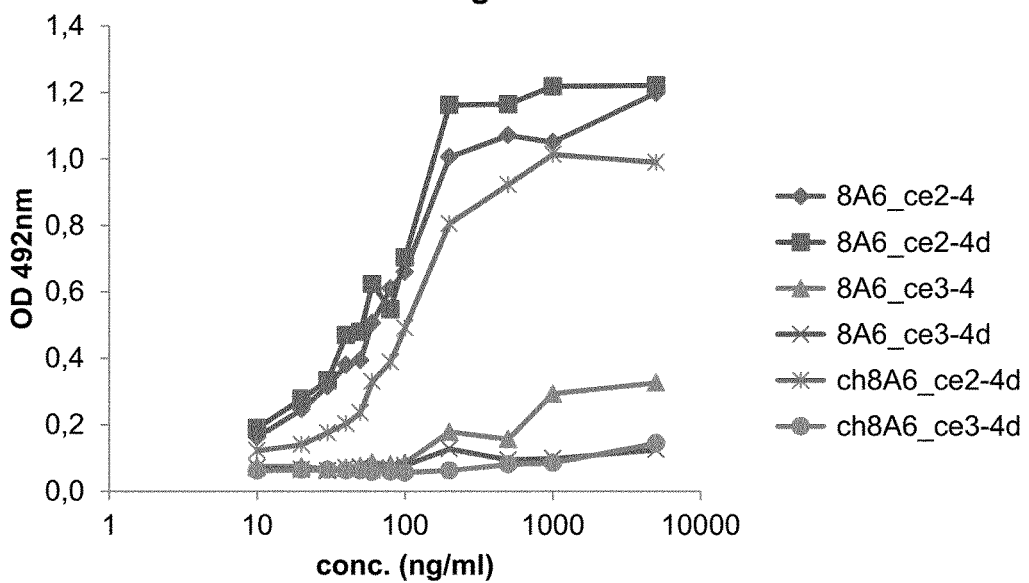
FIG. 20: Binding of 8A6-IgE variants to sFcεRIα determined by ELISA. The figure depicts a representative ELISA. The humanized anti-Fc gamma RIIB-IgE variants bind to sFcεRIα with the same affinity as the respective chimeric anti-Fc gamma RIIB-IgE version.

ELISA was performed using the same protocol as in Example 2. Binding of the hu8A6-IgE variants was tested compared to ch8A6_N297A. Here, no differences in binding affinity towards soluble FcγRIIB were detected (FIG. 19). Binding of humanized and chimeric 8A6-IgE variants to sFcɛRIα with its Fc part was tested. Both 8A6-IgE variants with the shortened Fc part (cɛ3-4) chimeric and humanized showed a lower affinity towards FcɛRIα compared to 8A6-IgE variants with complete Fc part (cɛ2-4). However, no differences in chimeric and humanized antibodies were detected (FIG. 20).

Example 8: 8A6-IgE Labeling and Binding Kinetics on Peripheral Blood Monocytes (PBMC)

The binding studies for FcɛRI were conducted with the full length ch8A6_cɛ2-4 construct in its deglycosylated version.

Methods:

8A6 (IgE) and (IgG) were labeled with the fluorescent dye NHS-Fluo488.

500 µg of each antibody was desalted into PBS via a PD-10 column according to the manufacturer's instructions. Absorbance of the elution fractions was measured with a photometer at 280 nm (reference: 320 nm) and fractions containing the highest antibody amount were pooled. After concentration via Vivaspin4 columns, approximately 400 µg of the antibodies could be regained.

The fluorescent dye Fluo488 was reconstituted in DMSO and its concentration was calculated by measuring the fluorescence at its emission maximum at 517 nm.

Antibody and dye were mixed in a molar ratio of 1:10, the dye being slowly added to the antibody solution under vortexing the sample. The exact calculations for antibody and dye amount can be found in the appendix. The solution was incubated for 1 h at 25° C. under constant shaking at 300 rpm (Eppendorf Thermomixer). Free dye molecules were separated by purification via a PD-10 column. Fractions with highest labeled protein amounts, measured at 280 nm (antibody) and 510 nm (dye) were pooled, concentrated again via Vivaspin4 columns, and the final concentration and the degree of labeling (D.O.L.) was calculated.

The final labeled antibodies were calculated:
ch8A6-cɛ2-4-degly-T: 1.35 µg/µl. D.O.L.: 2.2
ch8A6_cɛ3-4-degly-T: 1 µg/µl, D.O.L.: 2.86

Calculation of Fluorescent Dye and Antibody Amounts:
Molecular weight of 8A6 (IgE): approx. 176,000 Da=176,000 g/mol
350 µg antibody=2 nmol
Molecular weight of Fluo488: approx. 981 mol/l
Resuspension of an indefinite amount in DMSO
Dilution 1:5,000 in water and measurement of $OD_{517}$ (emission maximum of the dye)
Concentration [µg/µl]=dilution factor×OD517×918/80,000=8.6 nmol/µl Calculation of dye to antibody ratio:
Desired molar ratio of dye:antibody=10:1
antibody 2 nmol→dye 20 nmol
2.3 µl dye Calculation of Degree of Labeling (0.01):
Definitions for calculation of protein concentration and D.O.L
$A_{max}$=absorbance at emission maximum of the dye, 517 nm for Fluo488
$A_{280}$=absorbance at 280 nm (protein)
CF=correction factor; defined by Interchim specifically for every dye bound to protein; $A_{280}$ (free dye)/$A_{max}$ (free dye)
MW: molecular weight of the protein
ε: extinction coefficient
c[protein]=1,4×($A_{280}$−$A_{max}$×CF)
D.O.L.=($A_{max}$×MW)/(c[protein]×$ε_{dye}$)

Preparation of PBMCs by Ficoll Density Gradient Centrifugation

Buffy coats from healthy donors were diluted 1:1 with HBSS and 30 ml layered on 15 ml Biocoll Separating Solution in a 50 ml Falcon tube. After centrifugation at 1000×g for 20 min without the break, the leukocyte fraction was collected with a plastic pipette. Cells were washed twice with complete growth medium and counted in a Neubauer counting chamber.

Binding Kinetics of ch8A6 cε2-4-Degly-T and ch8A6 N297A on PBMCs 0.5×10$^6$ PBMCs in 100 μl complete growth medium were incubated in a 96-well-plate (flat bottom) in the incubator at 37° C. with the following antibody dilutions: 2 μg/ml ch8A6_cε2-4-degly-T cFluo488, 2 μg/ml ch8A6_N297A-Fluo488, 2 μg/ml 8A6 cε2-4-degly-T. An extra well was prepared for every time point. As a control, binding to FcγRIIB on PBMCs was blocked by preincubating ch8A6_cε2-4-degly-T-Fluo488 with a 5-fold molar excess of SM101 for 30 min at RT. Blockade of the FcγRIIB binding site was tested by FACS analysis after incubation on Raji cells.

After 10, 30, 60, 120 and 240 min, as well as after an overnight incubation, the cells were spun down at 400×g for 5 min and resuspended in 100 μl FACS buffer containing 2.5 μl α-hCD19-PeCy7, 5 μl α-hCD63-PerCP and 2.5 μl α-hCD193-APC in a round-bottom 96-well plate for 30 min on ice. After two washing steps with FACS buffer, samples were analyzed with a FACS Canto II.

Binding of Fluo488-Labeled 8A6-IgG and 8A6-IgE to Raji Cells

Figure 21:
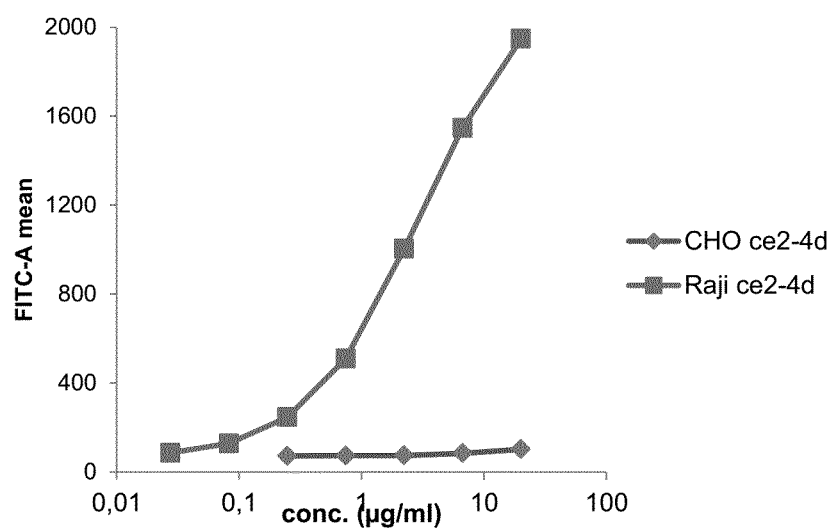
FIG. 21: Binding test of labeled 8A6-IgE-Fluo488 on Raji cells. Binding of the fluorescent labeled construct to FcγRIIB on Raji cells was tested and CHO cells (FcγRIIB neg.) served as control. Fluorescence in the FITC channel was assessed.

Raji cells were incubated with different concentrations of the labeled antibody and mean fluorescence values were plotted against the antibody concentrations. The antibody 8A6_cε2-4-degly showed high affinity binding to its receptor FcγRIIB at the surface of Raji cells. (see FIG. 21) The specificity of this binding was confirmed by the analysis of CHO cells, incubated with the same construct, where no surface signals for the labeled antibody was detected as it was expected due to CHO cells lacking the FcεRI receptor. These data confirmed that binding of the antibody was not altered throughout the labeling process or via the bound fluorochrome NHS-Fluo488.

Control of SM101 Masking of the FcγRIIB Binding Site of 8A6 cε2-4-Degly

To enable detection of binding of the Fc-part of 8A6-IgE to cells, the F(ab)2 domain, the FcγRIIB binding site, respectively, was blocked by preincubation of the antibody with SM101. The binding capacity of the constructs was analyzed with FACS. FACS analysis clearly showed a blockade of 8A6_cε2-4-degly to its receptor, FcγRIIB, after preincubation with a 5-fold molar excess of soluble receptor (SM101). The mean fluorescence value after preincubation with SM101 was reduced to 11.8%, compared to the untreated antibody. Thus, the masked 8A6_cε2-4-degly antibody could be used as a control for PBMC incubation.

Binding Kinetic on PBMCs

Binding of the antibody 8A6-IgE, labeled with Fluo488, on isolated PBMCs was assessed by FACS analysis. Therefore, cells were stained with α-hCD193-APC and α-hCD19-PeCy7 to distinguish B cells (CD19) and basophils (CD193, low SSC). CD63 was stained to analyze activation of the basophils.

CD63 expression on basophils was unchanged during the measurement (not shown).

Figure 22:
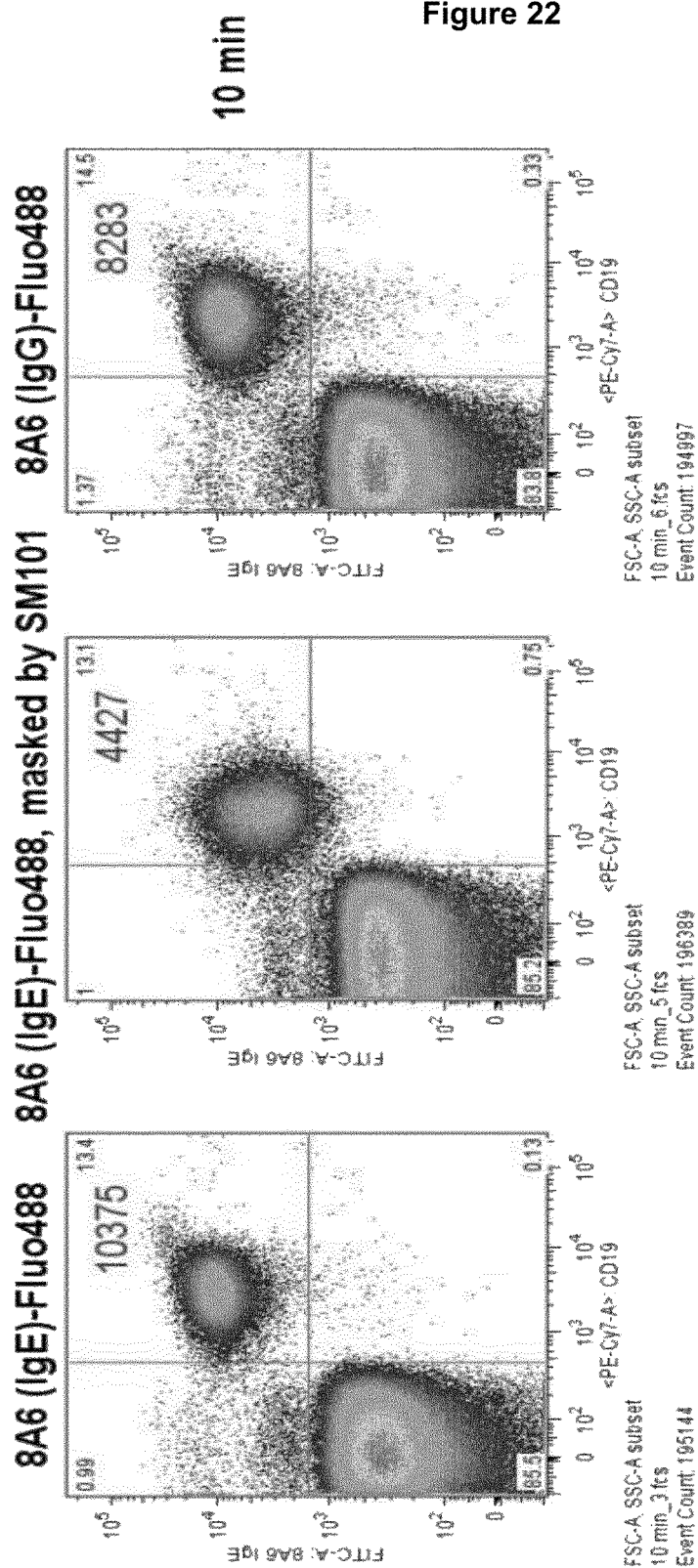
FIG. 22: Binding of ch8A6_ce2-4-degly and ch8A6_N297A to B cells within PBMC. FACS Analysis of 8A6-IgE (left row), 8A6-IgE masked with SM101 (middle row) and 8A6-IgG (right row) binding to B cells. At time points indicated at the right side, B cells were analyzed after staining with α-hCD19-PeCy7 for 8A6-IgE binding by FACS analysis. Numbers in the right upper quadrant show mean fluorescence intensity in the indicated quadrant.
Figure 22:
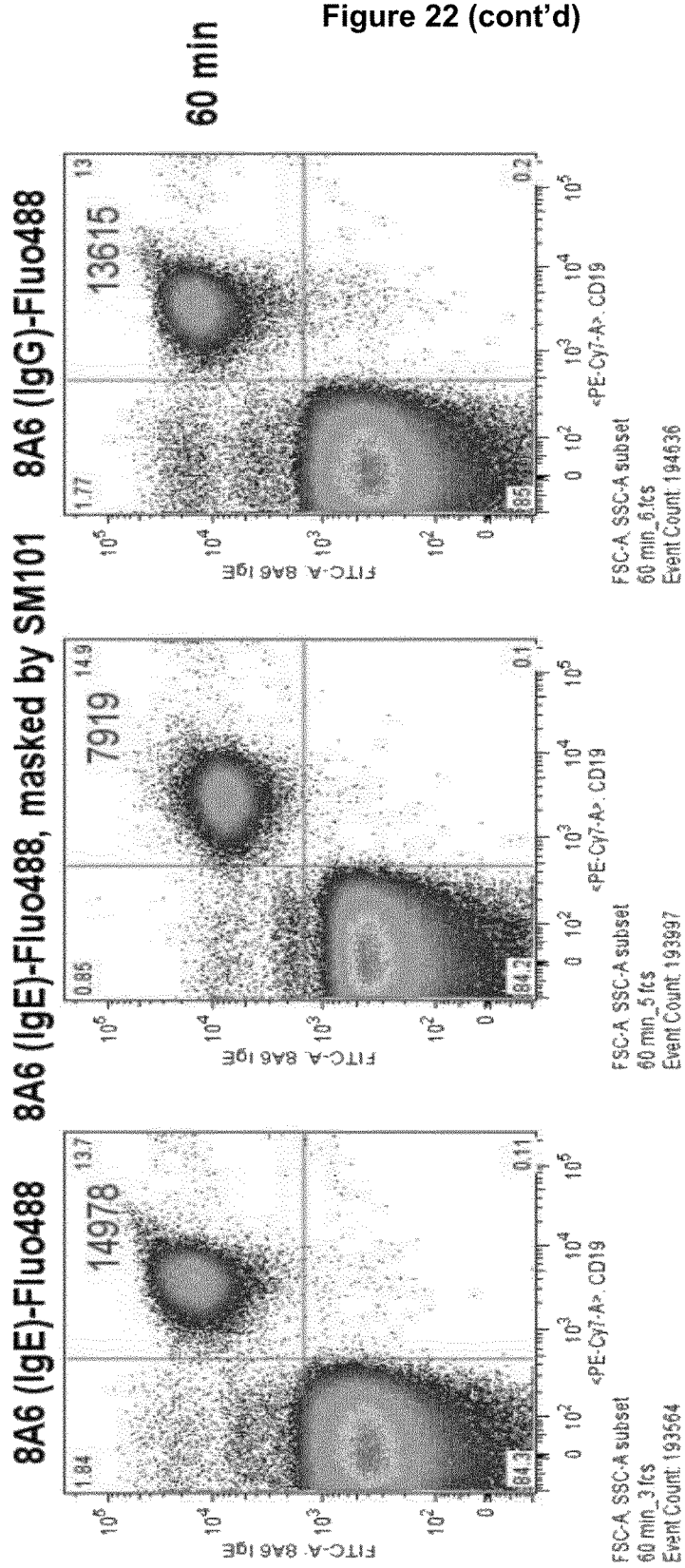
Figure 22:
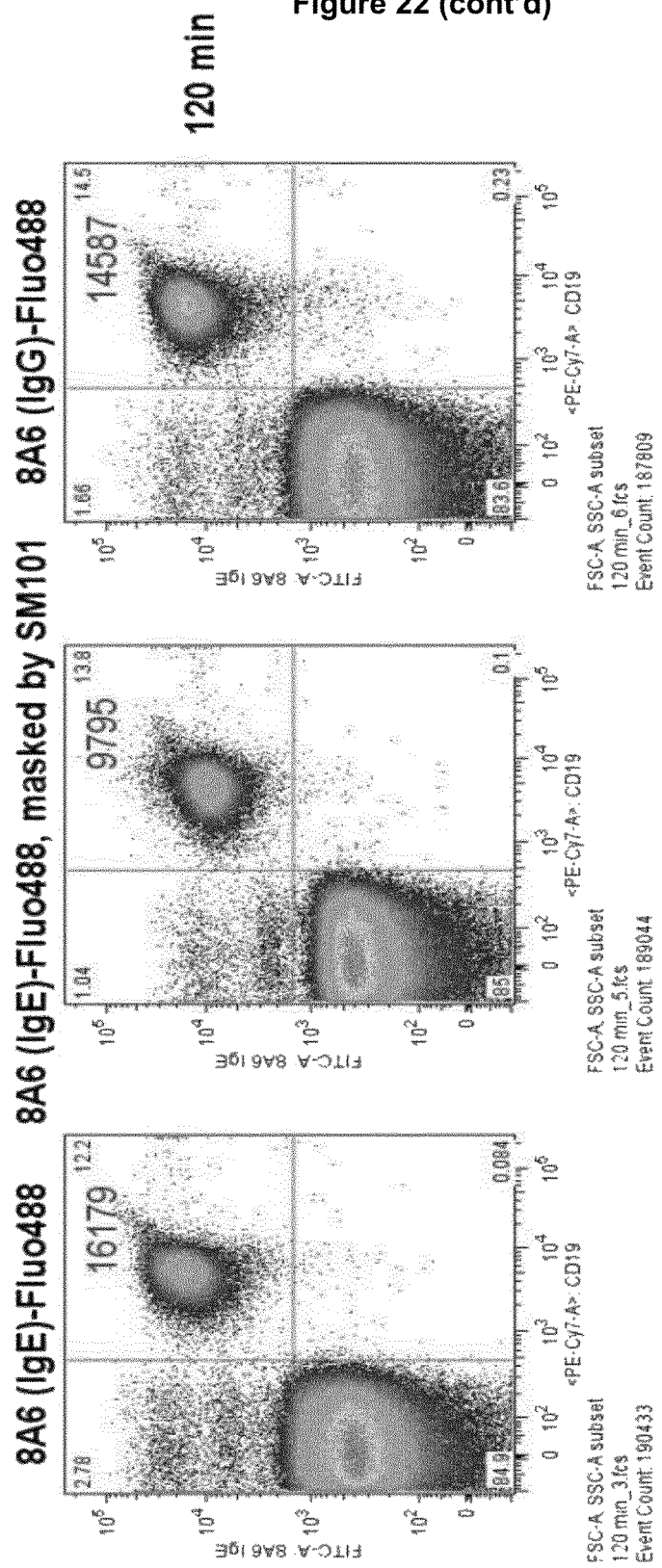
Figure 22:
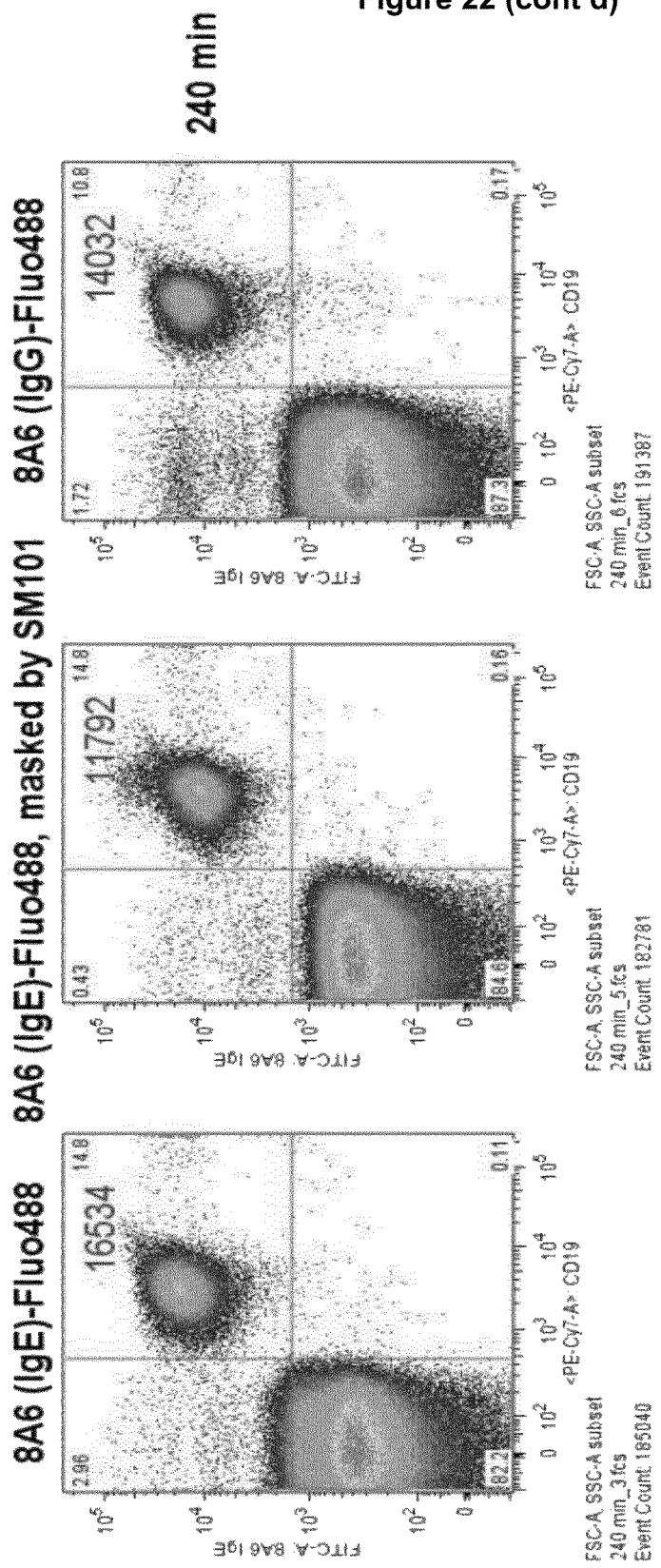
Figure 22:
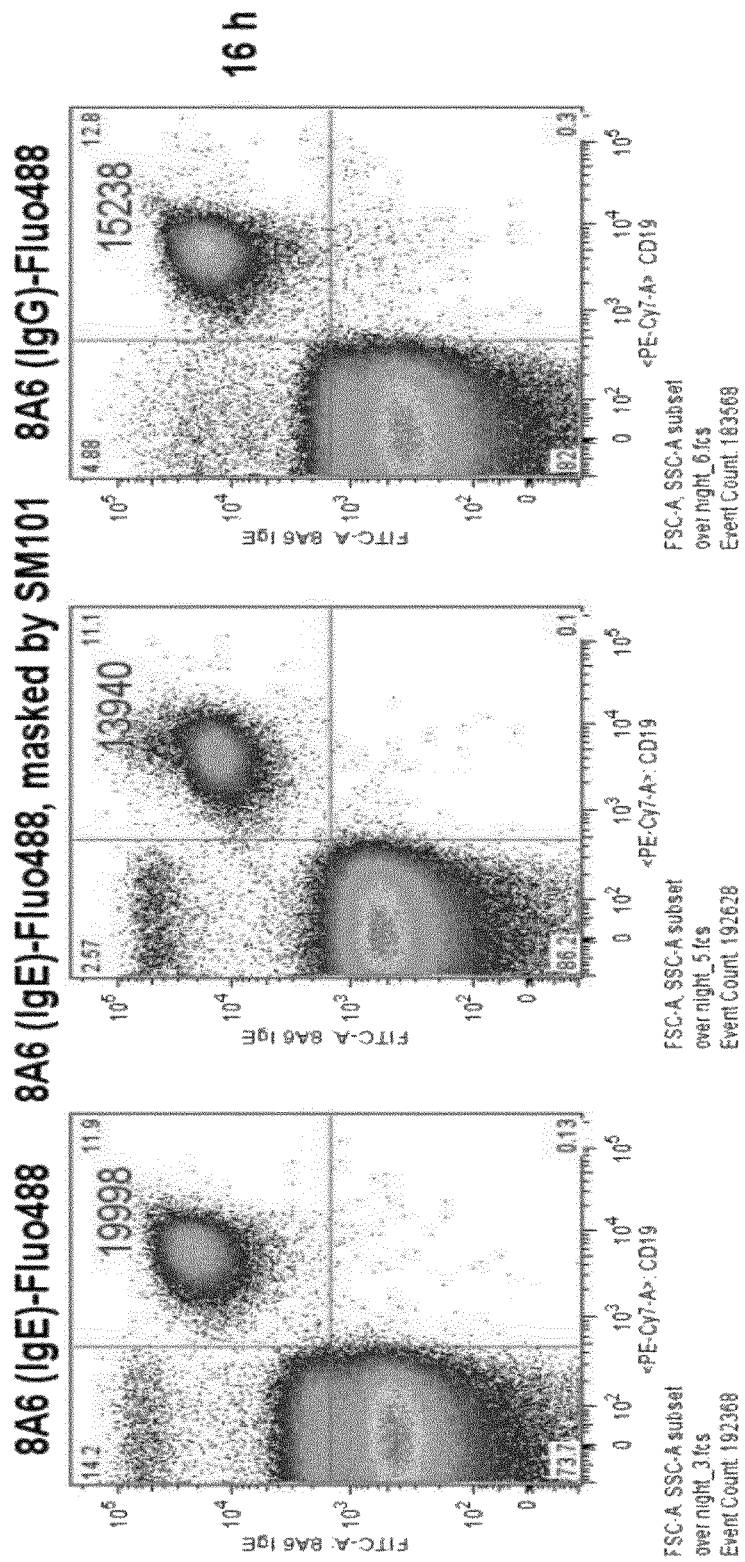

FIG. 22 shows the fluorescence signals on B cells, detected by an α-hCD19-PeCy7 antibody. Green numbers reflect the measured mean fluorescent values of CD19-positive cells for Fluo488-labeled antibodies.

Example 9: Basophil Activation Test (BAT)

The assay is based on the method first described by Sainte-Laudy et al. 1994 (Sainte-Laudy, J, et al., Analysis of membrane expression of the CD63 human basophil activation marker. Applications to allergologic diagnosis. Allerg. Immunol. (Paris) 26, 211-4) and 1996 (Sabbah, A and Sainte-Laudy, J., Flow Cytometry applied to the analysis of Lymphocyte and Basophil activation. ACI International 8, 116-9) where basophil activation by allergens or controls is detected by flow cytometry measuring the increase of CD63 (gp53) on the cellular surface. Allergens and positive controls are added to heparinized whole blood and CD63 surface expression is measured by a specific antibody staining containing anti-hCD193 to identify basophils and anti-hCD63 to measure activation. Histamin release can be measured in parallel as a second parameter for basophil activation and degranulation.

By crosslinking FcγRIIB and FcεRI with 8A6-IgE at the surface of basophils, the cellular response to an allergen via the FcεRI is downregulated.

50 μl heparinized whole blood from donors with a known pollen allergy (or other defined allergy with available allergen for testing) was obtained.

In these experiments the ch8A6_cε2-4-degly antibody was used in comparison to the: ch8A6_N297A chimeric 8A6 (IgG), N297A mutant For positive and negative controls, an incubation time of 15 min with allergen or controls was sufficient for appropriate activation of basophils, as described in the manual of the kit.

50 μl heparinized whole blood was incubated with 50 μl stimulus (allergen, fMLP or anti-FcεRI control antibody) and 100 μl stimulation buffer. α-FcεRI and fMLP were dissolved as described in the manual of the kit and used undiluted. Allergens were diluted 1:5 in stimulation buffer. Buffer and stimulus were prepared in Falcon tubes and 50 μl blood sample were added directly to this solution without contacting the tube walls. 20 μl Staining Reagent or commercially available antibodies (α-hCD63-PE and α-hCD193-Alexa647), dissolved in stimulation buffer, were added. Samples were gently vortexed and incubated in a water bath, prewarmed to 37° C., for 15 min. For lysis, 2 ml Lysing Reagent were applied to each tube, samples were then vortexed and incubated at RT for 10 min in the dark. After centrifugation at 500×g for 5 min, supernatants were removed and pellets resuspended in 300 μl wash buffer of the kit. FACS analysis was performed on a FACS Canto II using the following settings:

| FSC | linear | voltage: 269 |
| SSC | linear | voltage: 401 |
| FITC | log | voltage: 447 |
| PE | log | voltage: 379 |

An α-FcεRI antibody and the peptide fMLP (Formyl-Methionyl-Leucyl-Phenylalanine, SEQ ID NO: 38) were contained in the kit and used at 50 µl per sample.

Gating Strategy

Figure 23:
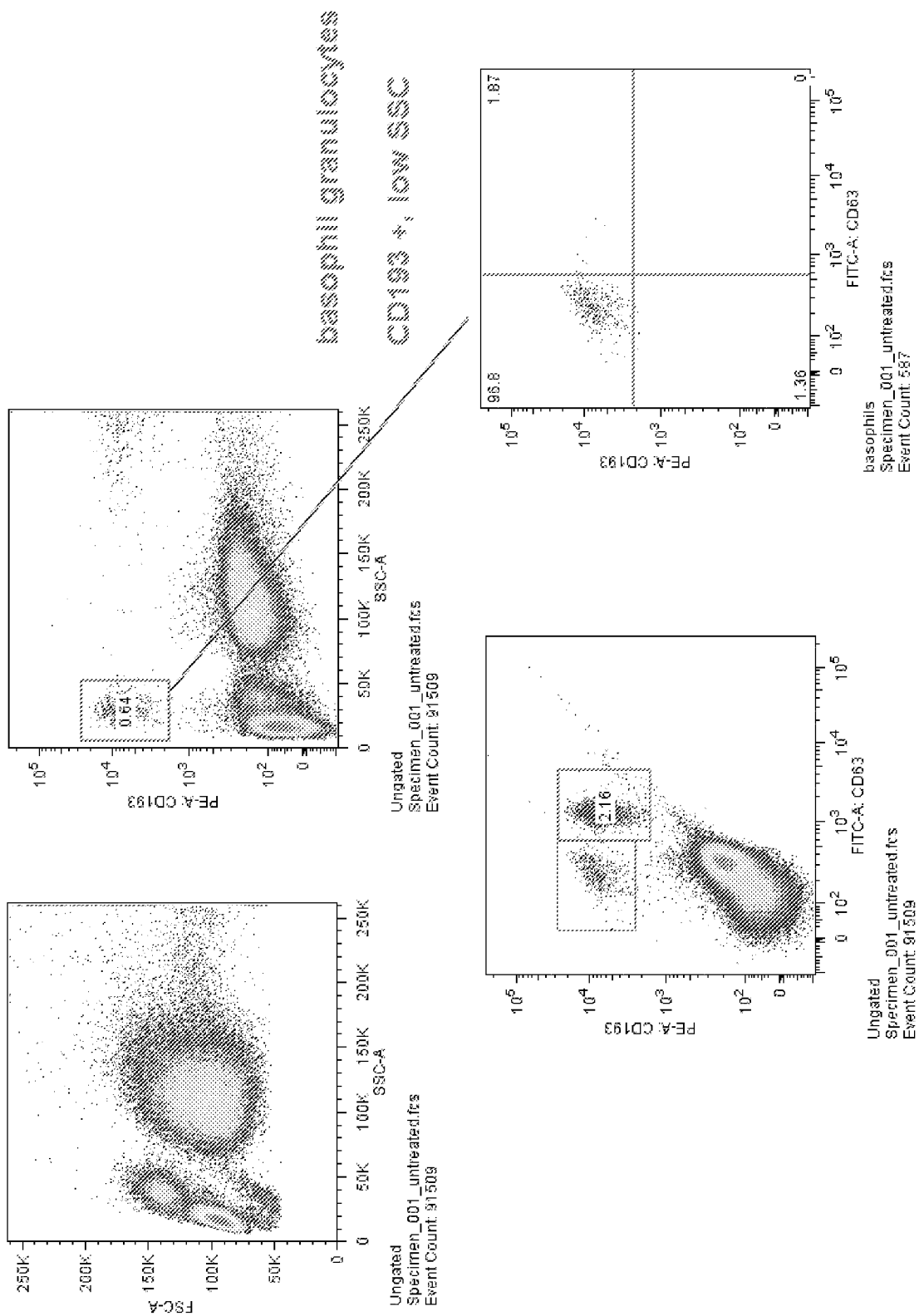
FIG. 23: Gating Strategy for detection of basophils. CD193 positive cells with low SSC were gated as basophils. A quadrant gate was applied where CD63 expression of untreated cells was set to 0.

FIG. 23 shows the gating strategy on lysed whole blood. The parameters FSC and SSC were set to linear. Three populations were visible: Lymphocytes, monocytes and granulocytes. Basophils can be detected at the same SSC level as lymphocytes. Plotting CD193 expression against SSC leads to detection of two distinct populations expressing CD193. The population with a low SSC was identified as basophilic granulocytes. A quadrant gate was applied in a plot showing CD193 (Y axis) vs. CD63 (X axis) expression, so that CD63 fluorescence in untreated samples was almost zero.

Using a backgating strategy, the cell populations were further characterized.

Gates including the CD63-low-expressing population and the CD63-high-expressing population were overlayed with the FSC-SSC-Plot of the ungated whole-blood lysate. The low-expressing population was found to be settled near the lymphocyte population, confirming this gated population to be basophils. By contrast, the high-expressing population was found at the very right limit of the SSC axis, reflecting those cells to be highly granular and being eosinophil granulocytes.

CD63 Expression of Positive and Negative Controls

CD63 expression of untreated cells was set to 0% or only very few positive cells in the lower quadrant of the quadrant gate that had been set on basophils. The α-FcεRI antibody reproducibly activated basophils to levels of 90% CD63-positive cells whereas the peptide fMLP only induced moderate CD63 expression with 25-30% of the cells being positive. To determine whether the antibodies that should be tested for their ability to reduce an allergic response could activate the basophils per se, ch8A6_N297A and ch8A6_cε2-4-degly were administered at two different concentrations without further activation of the cells.

Figure 24:
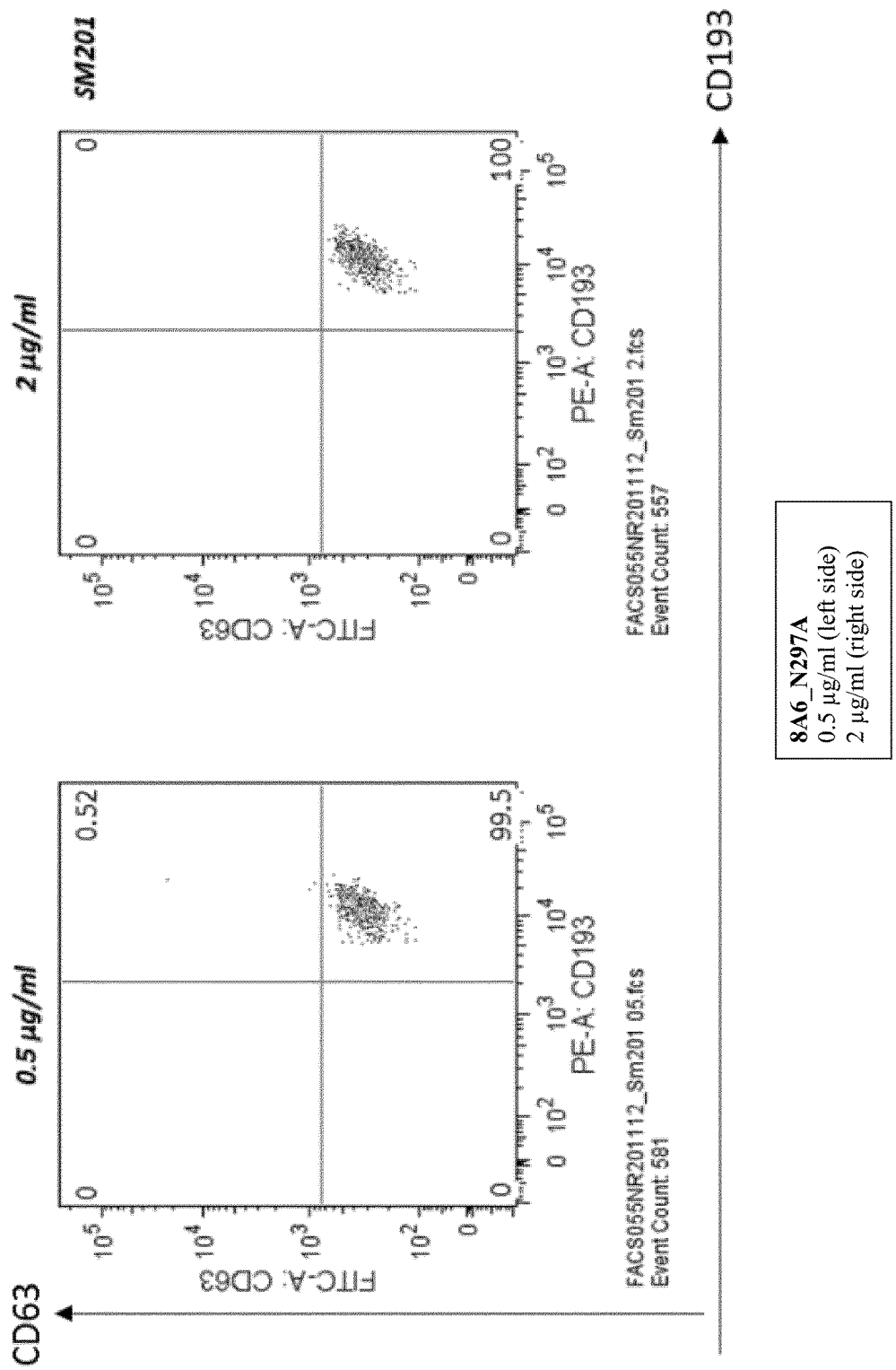
FIG. 24: CD63 expression of basophils treated with 8A6_N297A and 8A6_cε2-4-degly in different concentrations. To exclude potential activating effects of 8A6_N297A and 8A6_ce2-4-degly per se, samples incubated with 8A6_N297A and 8A6_ce2-4-degly over night were analyzed for their CD63 expression without further activation by antigen.
Figure 24:
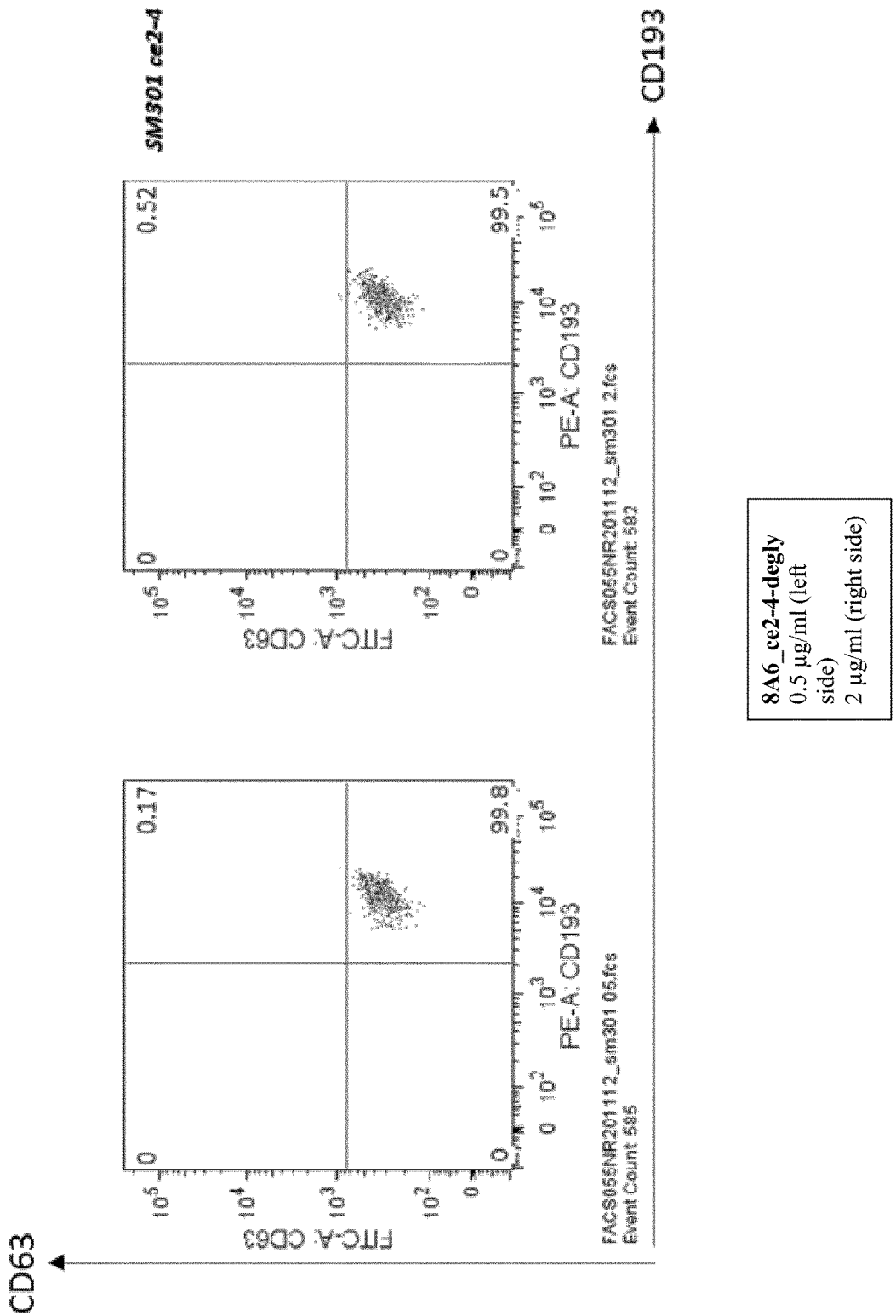

FIG. 24 shows the obtained data for these samples.

Figure 25:
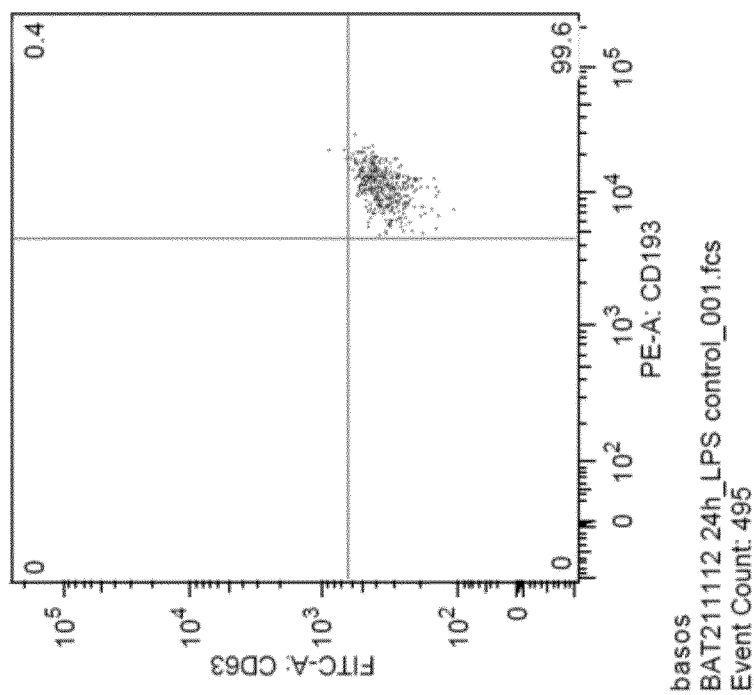
FIG. 25: LPS control for 8A6_ce2-4-degly incubation. Whole blood was incubated with 50 EU/ml LPS for 24 h and CD63 expression was analyzed.

Incubation of whole blood samples with 0.5 or 2 µg/ml of 8A6-IgG or 8A6-IgE did not activate the basophils per se as shown in the upper figure. Surface expression of CD63 did not change and less than 1% positive cells were detected in two independent experiments. In a next step of the analysis, the effect of endotoxin contaminations on basophil activation was studied. As the 8A6_cε2-4-degly contains ~30 EU/ml endotoxin from the production process, a LPS control was performed to exclude effects deriving from contaminated material. Thus, a separate blood sample was incubated with 50 EU/ml LPS (diluted 1:4 in the assay) in parallel to 8A6_cε2-4-degly alone. As shown in FIG. 25, treatment of basophils with LPS in concentrations as expected in contaminated production did not lead to unspecific activation of the cells. Thus, effects measured after treatment with 8A6_cε2-4-degly can be directly correlated to the activity of the antibody.

Preventive Treatment of Basophils with 8A6 cε2-4-Degly

Whole blood samples were incubated with controls, 8A6_N297A and 8A6_cε2-4-degly in varying concentrations. Samples were taken at different time points and the potential of basophils to be activated by pollen was measured.

A) Time-Point 0 h

Directly after addition of the respective antibodies to whole blood aliquots, first samples for time point 0 were taken and their potential to be activated was analyzed by pollen stimulation. This time point was measured in two independent experiments. No effect of 8A6_N297A or 8A6_cε2-4-degly was visible at this time point, representing about 5 min of incubation with the antibodies (time from pipetting to sample incubation). The basophils in all samples could be activated by pollen to about 90% CD63-expressing cells.

B) Time-Point 2 h

After 2 h of incubation, basophil activation was detected without loss of activity as seen by α-FcεRI activation (92% positive cells) and untreated cells with pollen stimulation (93.4%). Incubation with 8A6_N297A in concentrations ranging from 0.5 to 5 µg/ml did not influence basophil activation by pollen (values between 91 and 91.6% positive cells). At this time point, basophil activation seemed to be reduced in samples that had been treated with 8A6_cε2-4-degly (84.4 to 88%), although a dose-dependency was not detected.

C) Time-Point 6 h

Figure 26:
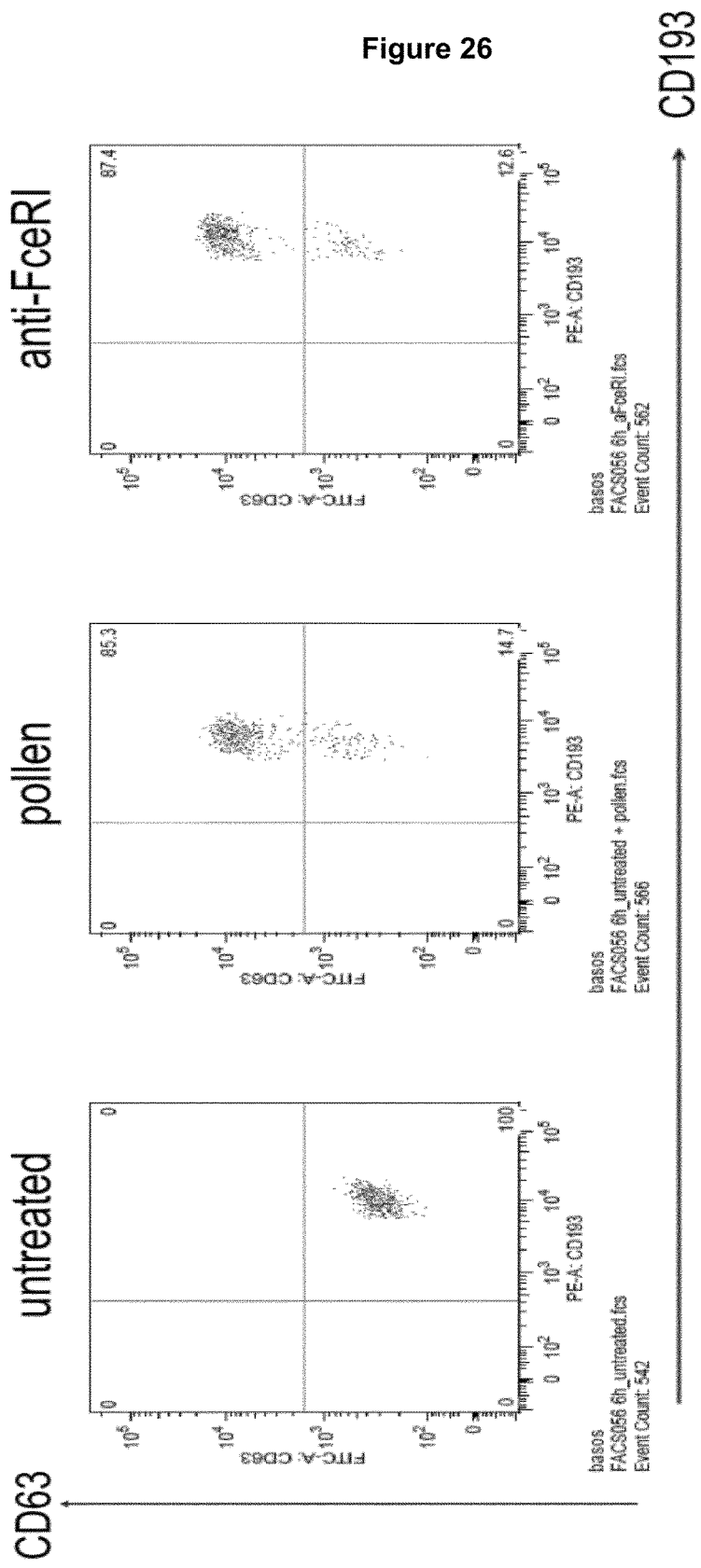
FIG. 26: Activation of controls after 6 h.

After 6 h incubation, the potential of cells to be activated by positive controls decreased to around 85% for pollen activation and 87% for the treatment with α-FcεRI (FIG. 26)

Figure 27:
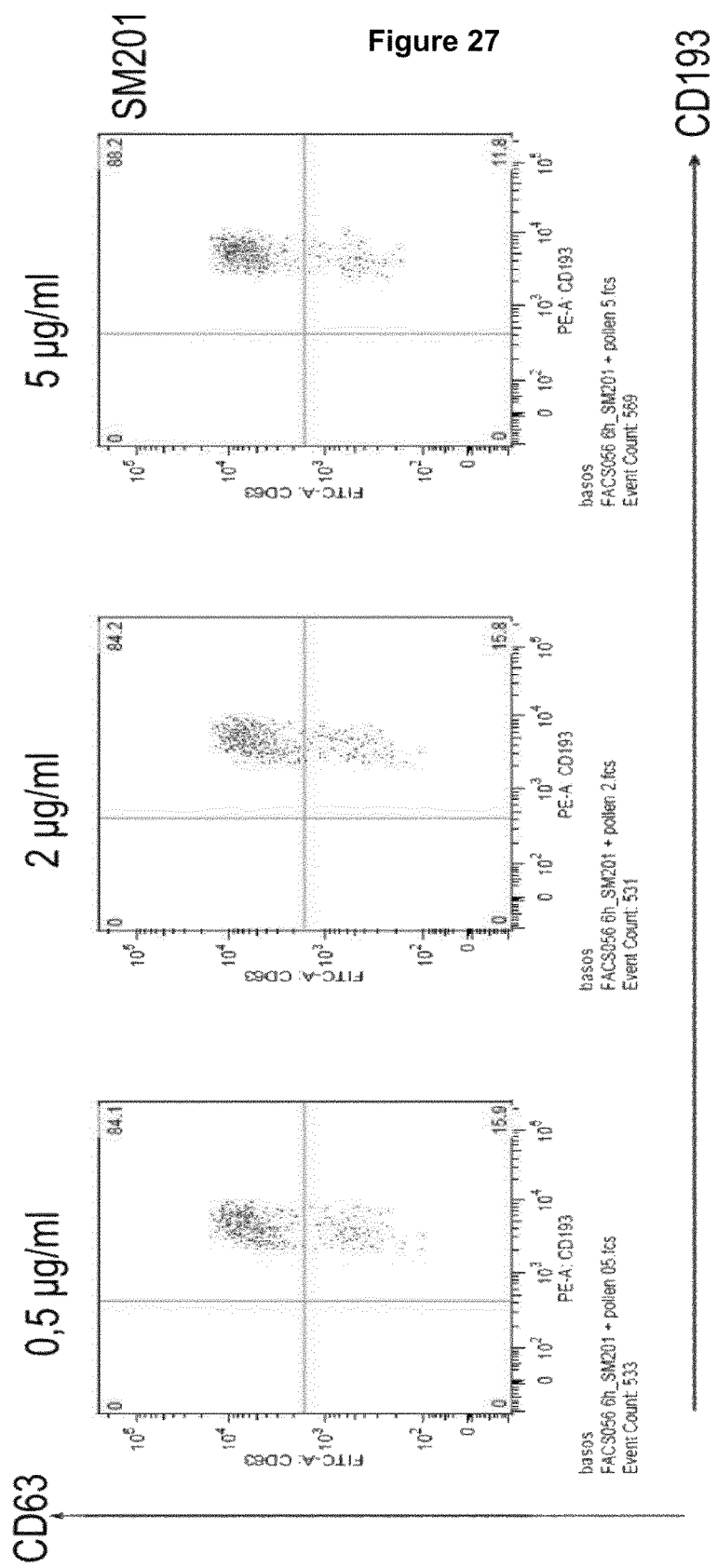
FIG. 27: Activation of 8A6-IgG or 8A6-IgE treated samples after 6 h.
Figure 27:
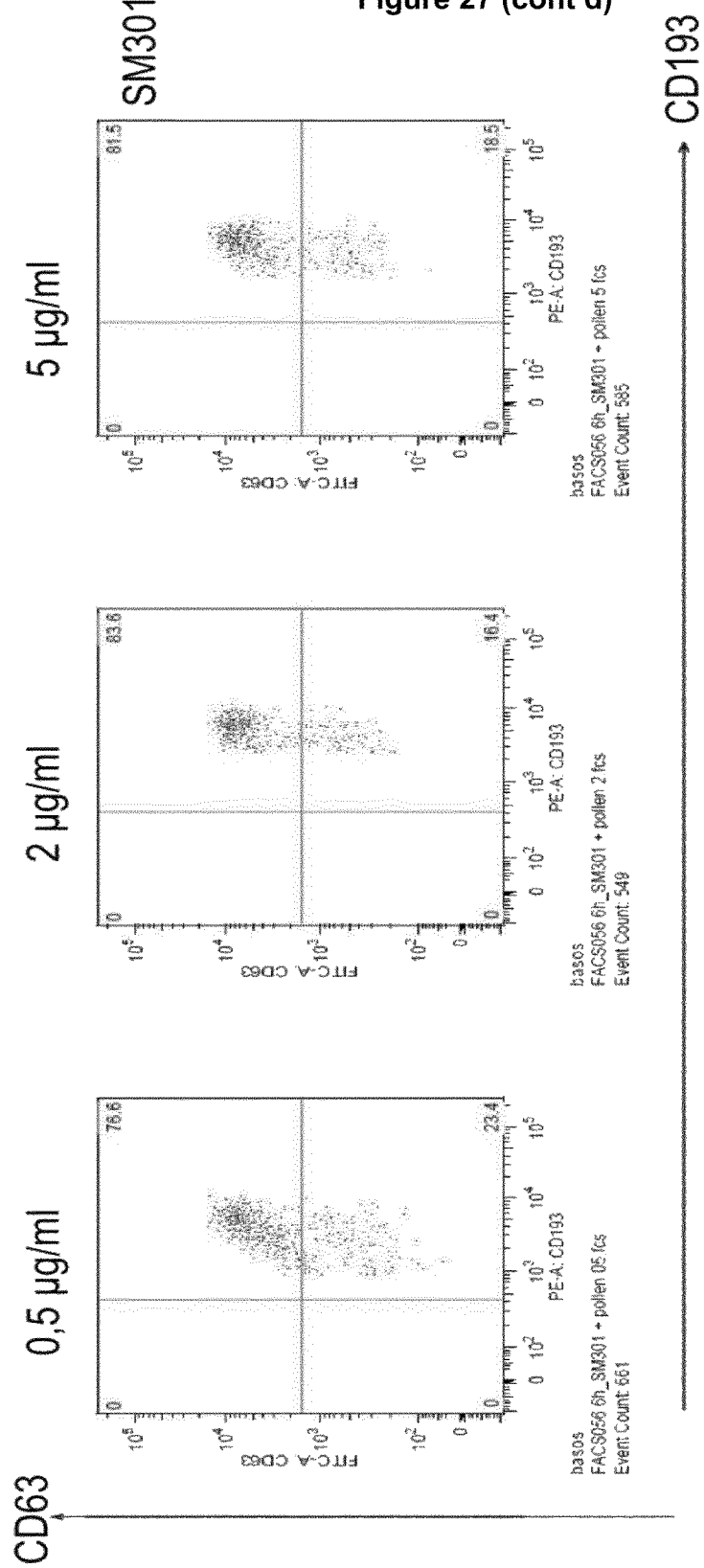

Whereas treatment with 8A6-IgG showed results comparable to the positive controls (85-88%), cells incubated with 8A6-IgE showed a decreased activation potential (76-84%) FIG. 27). After incubation with 0.5 µg/ml 8A6_cε2-4-degly, only 76.6% of the basophils could be activated by pollen. However, no dose dependency was detected and higher dosage showed slightly elevated CD63 expression compared to 0.5 µg/ml treatment.

D) Time-Point 24 h

Figure 28:
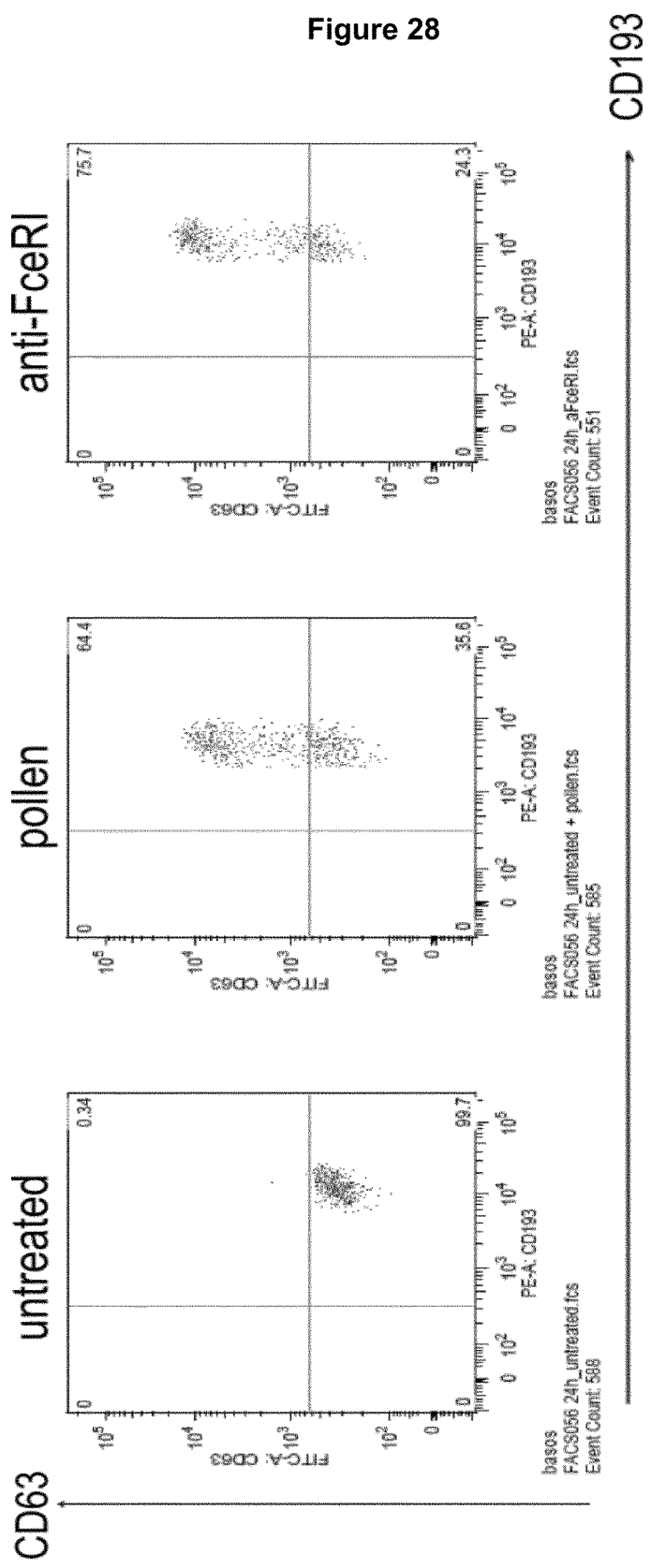
FIG. 28: Activation of controls after 24 h.
Figure 29:
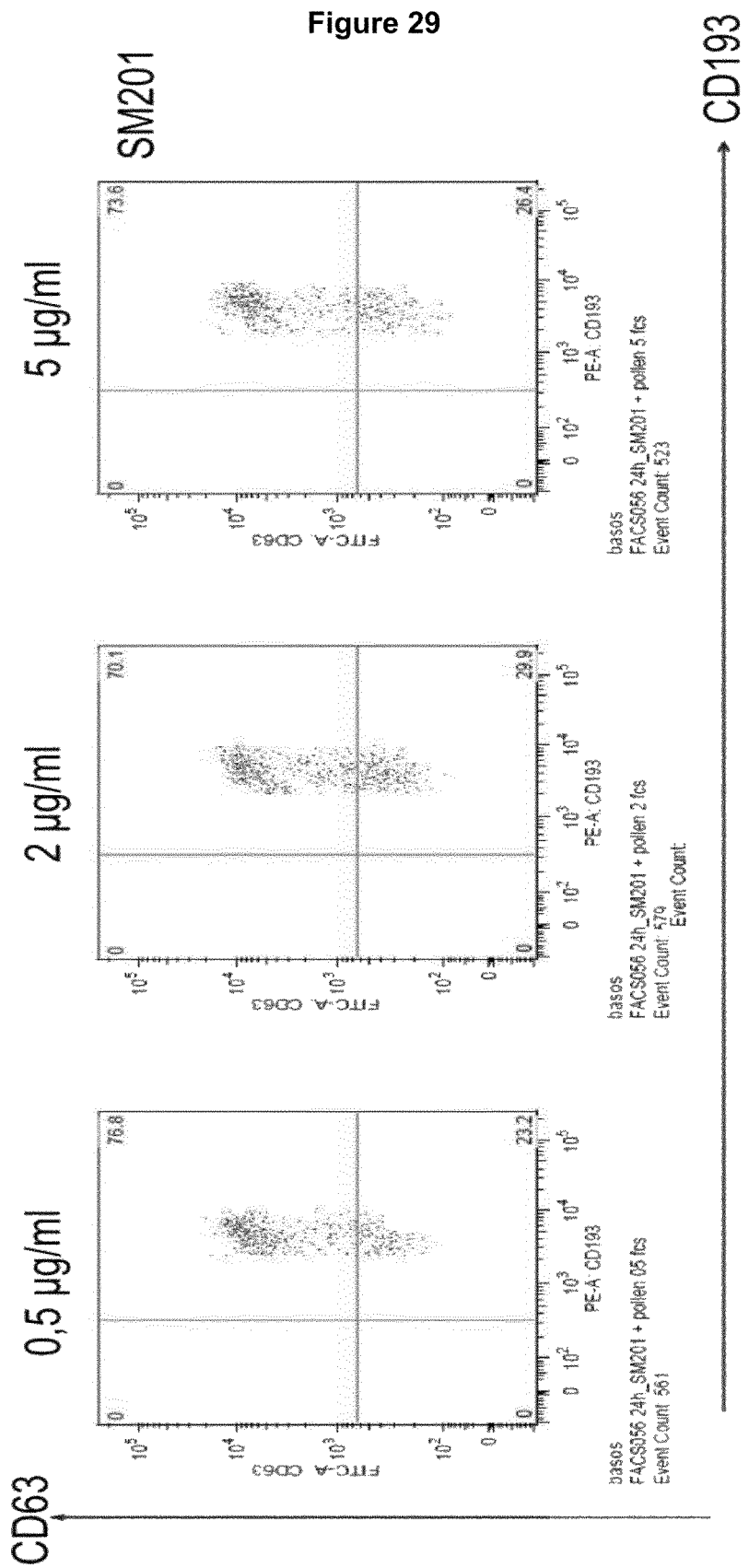
FIG. 29: Activation of 8A6-IgG or 8A6-IgE (8A6-cε2-cε4_deglycosylate) treated samples after 24 h.
Figure 29:
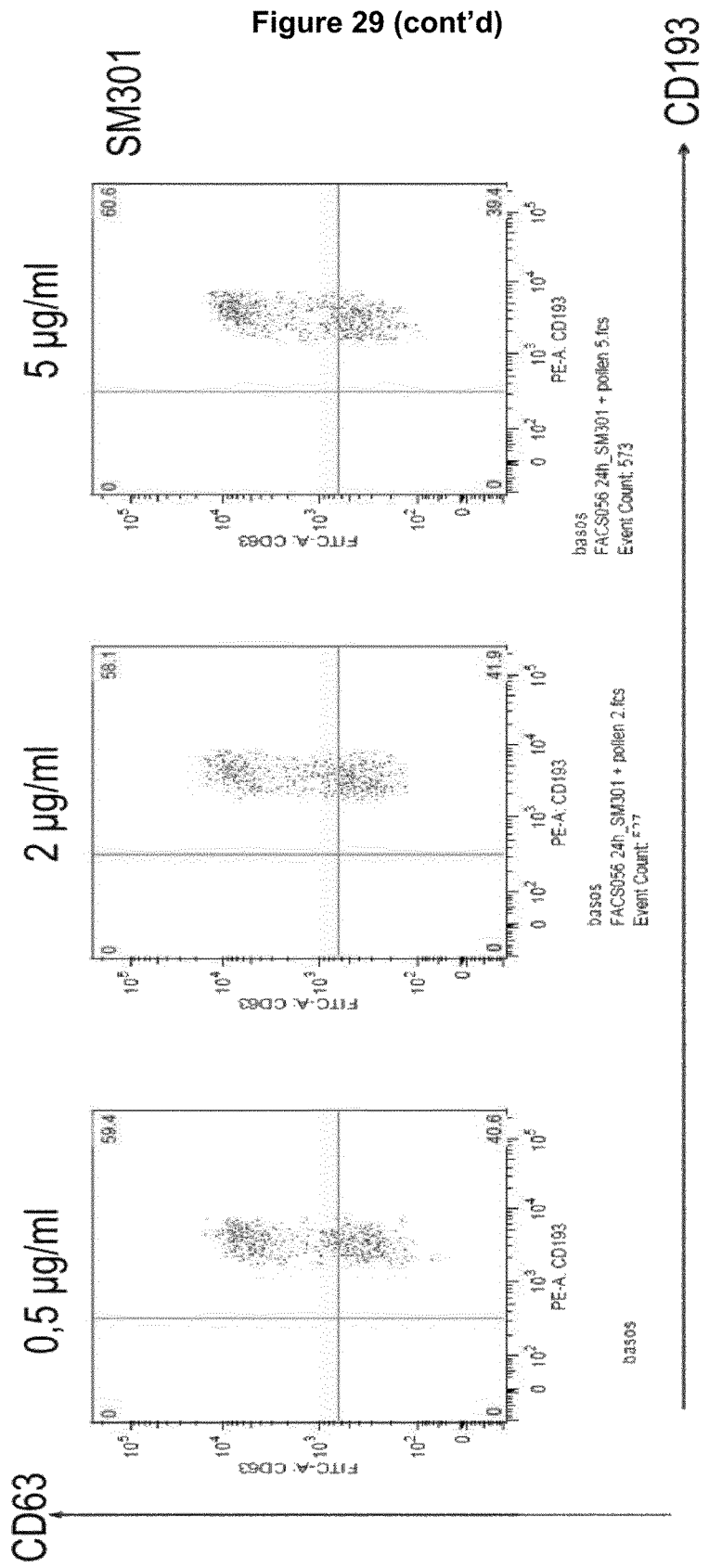
Figure 30:
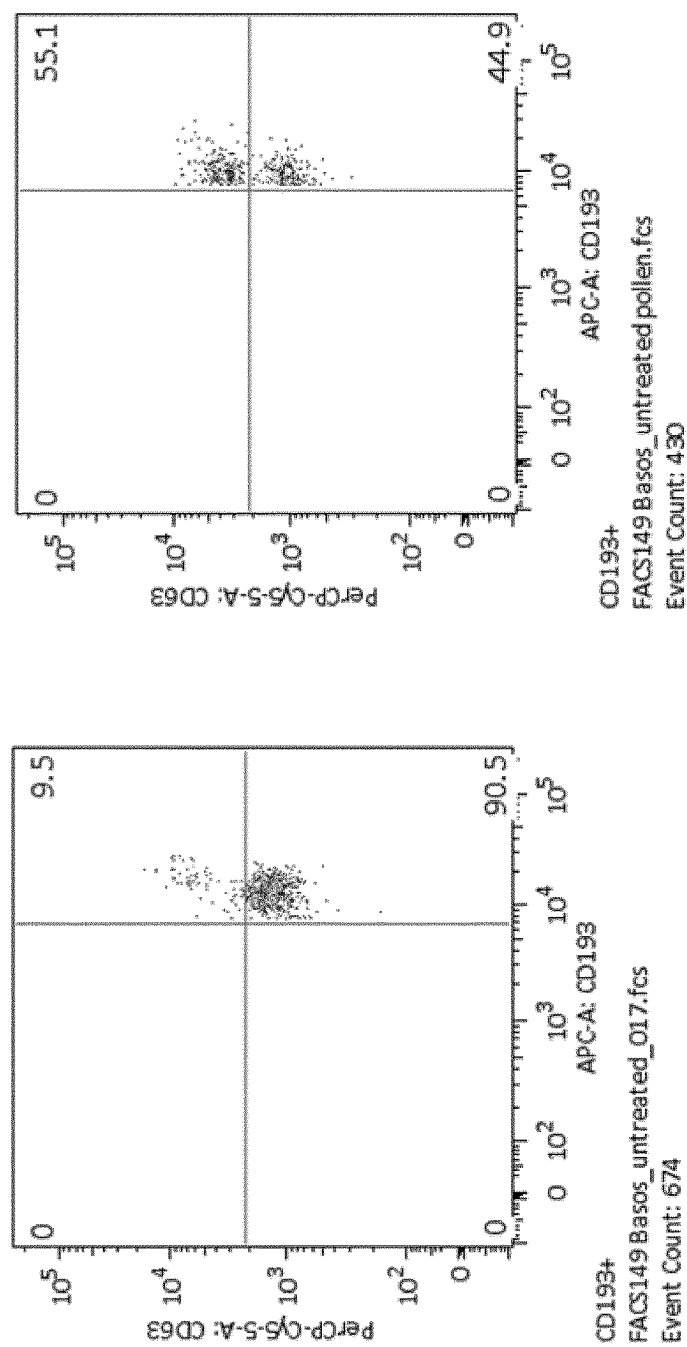
FIG. 30: Pollen activation test.
Figure 30:
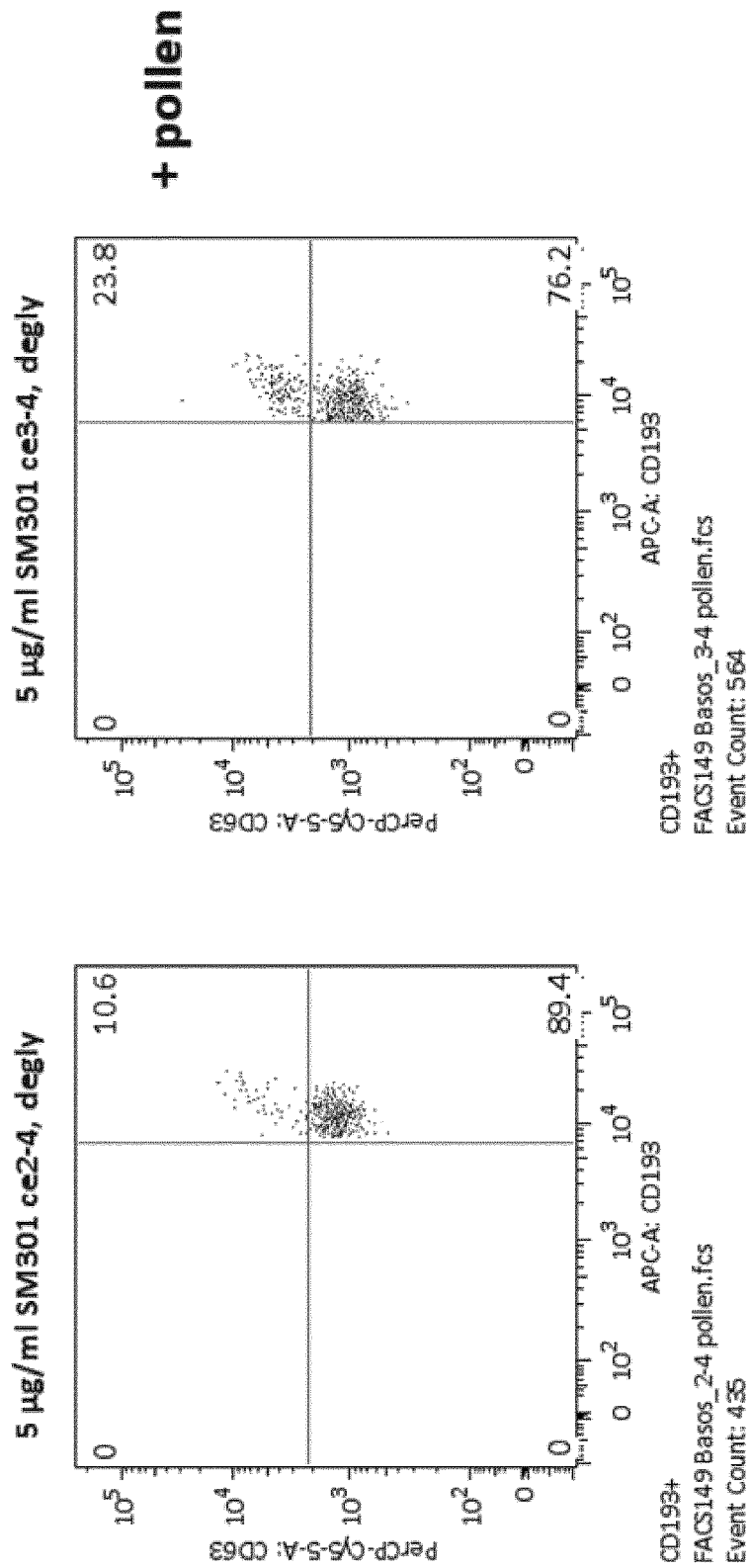
Figure 30:
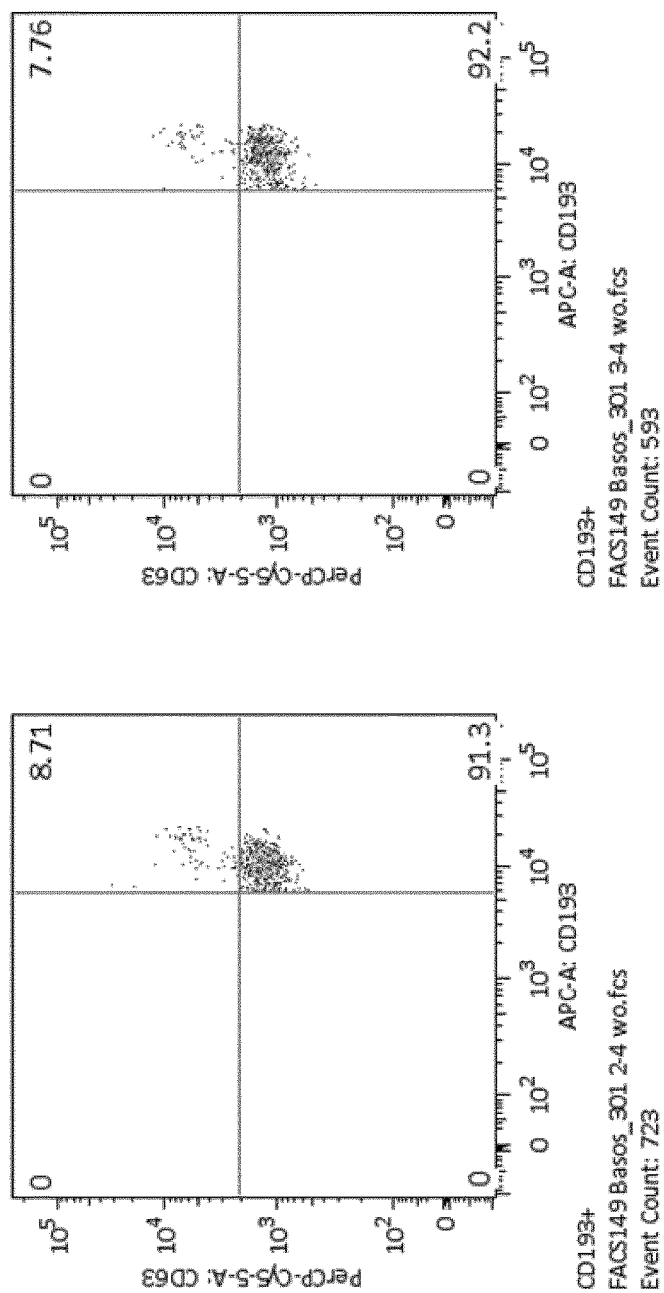

The last time point, measured in two independent experiments, showed a reduction in activation for the α-FcεRI treatment to 75% CD63 expression (FIG. 28 and FIG. 29).

Example 10: Pollen Activation Test

Heparinized whole blood from a healthy donor that was tested positive for a pollen atopy, was incubated over night with 5 µg/ml of 8A6_ce2-4 deglycosylated or 8A6_ce3-4 deglycosylated) (SM301 cε2-4 or cε3-4), respectively. For analysis, 50 µl blood sample was mixed with 50 µl pollen (1:5 prediluted in stimulation buffer), 100 µl stimulation buffer (FlowCast Kit) and 20 µl staining solution (3 µl a-hCD193-Alexa647, 3 µl a-hCD63-PerCP, 3 µl a-hCD203c-PE, 11 µl stimulation buffer). Samples were gently mixed on a vortex mixer and incubated in a water bath, prewarmed to 37° C., for 15 min. For lysis, 2 ml PharmLyse reagent (BD Biosciences) were applied to each tube, samples were then mixed again and incubated at RT for 10 min in the dark. After centrifugation at 500×g for 5 min, supernatants were removed and pellets resuspended in 300 µl FACS buffer. A gate was set on SSC high, CD193 positive but CD203c negative cells, constituting eosinophils.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A recognition molecule, wherein said recognition molecule is an antibody which binds with a first binding domain to a Fcε receptor (FcεR) and with a second binding domain to a Fc gamma receptor IIB (FcγRIIB), wherein the first binding domain comprises at least a portion of an IgE constant region, said portion comprising at least C epsilon 3 and C epsilon 4, wherein the second binding domain comprises at least a portion of a Fab domain, and wherein said recognition molecule comprises in its second binding domain the following CDR sequences of the variable heavy and light region:
   (i) an H-CDR1 sequence which is 60% or more identical to the H-CDR1 sequence shown in SEQ ID NO. 20,
   (ii) an H-CDR2 sequence which is 36% or more identical to the H-CDR2 sequence shown in SEQ ID NO. 21,
   (iii) an H-CDR3 sequence which is 50% or more identical to the H-CDR3 sequence shown in SEQ ID NO. 22,
   (iv) a L-CDR1 sequence which is 64% or more identical to the L-CDR1 sequence shown in SEQ ID NO. 23,
   (v) a L-CDR2 sequence which is 29% or more identical to the L-CDR2 sequence shown in SEQ ID NO. 24, and
   (vi) a L-CDR3 sequence which is 78% or more identical to the L-CDR3 sequence shown in SEQ ID NO. 25,
   which comprises in its heavy chain variable region H-CDR1, H-CDR2 and H-CDR3 as shown in SEQ ID NOs. 29, 30 and 31 and in its light chain variable region L-CDR1, L-CDR2 and L-CDR3 shown in SEQ ID NOs. 32, 33 and 34; and
   wherein said recognition molecule further comprises in its heavy and light chain variable region the following CDR sequences:
   (a) SEQ ID NO. 14 (CDR-H1), SEQ ID NO. 15 (CDR-H2), and SEQ ID NO. 16 (CDR-H3) in its heavy chain variable region, and SEQ ID NO. 17 (CDR-L1), SEQ ID NO. 18 (CDR-L2), and SEQ ID NO. 19 (CDR-L3) in its light chain variable region; or
   (b) SEQ ID NO. 20 (CDR-H1), SEQ ID NO. 21 (CDR-H2), and SEQ ID NO. 22 (CDR-H3) in its heavy chain variable region, and SEQ ID NO. 23 (CDR-L1), SEQ ID NO. 24 (CDR-L2), and SEQ ID NO. 25 (CDR-L3) in its light chain variable region.

2. The recognition molecule of claim 1, wherein the antibody does not bind to the Fc gamma receptor IIA (FcγRIIA).

3. The recognition molecule of claim 1, wherein the antibody is a non-blocking antibody such that its binding to the Fc receptor via its variable regions does not interfere with the binding of immune complexes, or aggregated IgG, to cells.

4. The recognition molecule of claim 3, wherein said antibody is chimeric or humanized.

5. The recognition molecule of claim 1, wherein said recognition molecule increases ITIM phosphorylation of FcγRIIB of Daudi cells about 4 to 10-fold in comparison to Daudi cells not treated with said recognition molecule.

6. The recognition molecule of claim 1, wherein the heavy chain variable region comprises the amino acid sequence shown in SEQ ID NO. 3, with at least one of the mutations selected from the group consisting of amino acid Q at position 1 being replaced by E, amino acid V at position 11 being replaced by L, amino acid G at position 42 being replaced by K, amino acid S at position 50 being replaced by V, amino acid Y at position 53 being replaced by S, amino acid K at position 58 being replaced by T, amino acid G at position 61 being replaced by A, amino acid S at position 75 being replaced by T, amino acid K at position 76 being replaced by R, amino acid N at position 77 being replaced by S, and amino acid T at position 78 being replaced by N.

7. The recognition molecule of claim 1, wherein the light chain variable region comprises the amino acid sequence shown in SEQ ID NO. 4, with at least one of the mutations selected from the group consisting of amino acid Q at position 1 being replaced by N, amino acid S at position 28 being replaced by N, amino acid S at position 31 being replaced by T, amino acid V at position 33 being replaced by L, amino acid D at position 34 being replaced by A, amino acid Y at position 49 being replaced by F, amino acid T at position 53 being replaced by N, amino acid Y at position 55 being replaced by A, amino acid L at position 89 being replaced by Q, and amino acid N at position 93 being replaced by Y.

8. The recognition molecule of claim 1, wherein the second binding domain has in its heavy chain variable region the amino acid sequence shown in SEQ ID NOs. 1 or 3 and/or in its light chain variable region the amino acid sequence shown in SEQ ID NOs. 2 or 4.

9. The recognition molecule of claim 1, wherein the IgE constant region has the amino acid sequence of SEQ ID NO: 35 or 36.

10. The recognition molecule of claim 1, wherein the antibody is glycosylated or deglycosylated.

11. The recognition molecule of claim 1, wherein the antibody binds in vitro to human FcγRIIB with an affinity having an off-rate constant of at least $4.9 \times 10^{-4} s^{-1}$.

12. The recognition molecule of claim 1, wherein the antibody binds in vitro to human FcεRI with an affinity having at least $1.2 \times 10^{-7}$ Kd (M).

13. The recognition molecule of claim 1, which specifically binds to and epitope comprising amino acids 20-40 of human FcγRIIB according to SEQ ID NO. 5.

14. A nucleic acid sequence encoding a recognition molecule of claim 1.

15. A vector comprising at least one of the nucleic acid sequences according to claim 14 inserted into said a vector.

16. A host cell transfected with a nucleic acid sequence of claim 14.

17. A pharmaceutical composition comprising as an active ingredient a recognition molecule of claim 1.

18. The pharmaceutical composition of claim 17 for the treatment or prophylaxis of diseases associated with basophils.

19. The pharmaceutical composition of claim 18 for the treatment or prophylaxis of allergies.

20. A method of treating a disease associated with basophils in a subject in need thereof, the method comprising administering to the subject an effective amount of the recognition molecule of claim 1.

21. The method of claim 20, wherein the disease associated with basophils is an allergic disease.

* * * * *